United States Patent [19]

Klein

[11] Patent Number: 5,786,338

[45] Date of Patent: Jul. 28, 1998

[54] METHOD OF TREATING HYPERCHOLESTEROLEMIA WITH A MACROLIDE ANTIBIOTIC

[76] Inventor: Ira Klein, 5 Windermere, Houston, Tex. 77063

[21] Appl. No.: 646,062

[22] Filed: May 7, 1996

Related U.S. Application Data

[60] Provisional application No. 60/000,583, Jun. 28, 1995.

[51] Int. Cl.$^6$ ................................................. A61K 31/70
[52] U.S. Cl. ............................. 514/29; 536/7.2; 536/7.4
[58] Field of Search ............................... 514/29; 536/7.2, 536/7.4

[56] References Cited

U.S. PATENT DOCUMENTS 4,482,540  11/1984  Gordon et al. .

OTHER PUBLICATIONS

Achord, J.L., Review of Alcoholic Hepatitis, and Its Treatment, *The American Journal of Gastroenterology*, 88(11):1822–1828 (1993).

Alpers, D.H., et al., Fatty Liver: Biochemical and Clinical Aspects, *Diseases of the Liver*, 4th Ed., 25:815–829, 1224–1229 (1975).

Bacon, B.R., et al. Nonalcoholic Steatohepatitis: An Expanded Clinical Entity, *Gastroenterology*, 107:1103–1109 (1994).

Cohen, et al., The SGOT/SGPT Ratio: An Indicator of Alcoholic Liver Disease, *Dig. Dis. Sci.*, 24:835–838 (1979).

Fortmann, et al., Disorders of Lipid Metabolism, *Scientific American*, 9 Metabolism:1–24 (1993).

Furuchi, T., et al., Bafilomycin A$_1$, a Specific Inhibitor of Vacuolar–type H$^+$–ATPase, Blocks Lysosomal Cholesterol Trafficking in Macrophages, *The Journal of Biological Chemistry*, 258:27345–27348 (1993).

Goldberg, et al., VA Cooperative Study on Alcoholic Hepatitis IV, *American Journal of Gastroenterology*, 81:1029–1034 (1986).

Gregory, P.G., Cirrhosis of the Liver in *Scientific American Medicine for Gastroenterology*, pp. 1–18 (1995).

Havel, R.J., et al., Management of Primary Hyperlipidemia, *The New England Journal of Medicine*, 332:1491–1498 (1995).

Holme, I., et al., Risk factors and raised atherosclerotic lesions in coronary and cerebral arteries. Statistical analysis for the Oslo Study, *Arteriosclerosis* 1:250–256 (1981).

Isselbacher, K.J. et al., Infiltrative and Metabolic Disease affecting the Liver in *Harrison's Principles of Internal Medicine*, eds. Brawnwald, E. et al., pp. 1353—54 (1988).

Kannel, W.B., et al., Epidemiology of coronary atherosclerosis: Postmortem vs clinical risk factor correlation's. The Framingham Study. In: Gotto, A.M., Jr., et al., eds. *International Symposium on Atherosciersosis*, 5th, Houston, 1079; Atherosclerosis V. New York Springer–Verlag, pp. 54–56 (1980).

Kawashima, et al., New Cholesterol Biosynthesis Inhibitors MC–031 (O–Demethylchlorothericin), –032 O–Demethyhydroxychlorothricin), –033 and –034, *Journal of Antibotics*, 45(2):207–212 (1992).

Lipids Research Clinics Program, The Lipid Research Clinics Coronary Primary Prevention trial Results. I. Reduction in incidence of coronary heart disease, *JAMA* 251:351–364 (1984).

Ludwig, et al., Nonalcoholic Steatohepatitis, Mayo Clinic Experiences With A Hitherto Unnamed Disease, *Mayo Clinic Proceedings*, 55:434–438 (1980).

McGills, H.C., et al., Relationship of Lipoprotein cholesterol concentrations to experimental atherosclerosis in baboons, *Artheriosclerosis* 1:3–12 (1981).

Metropolitan Height and Weight Tables, New York: Metropolitan Life Insurance Company (1983).

Physicians' Desk Reference®, pp. 405–407, 1789–1791 (1994).

Physicians' Desk Reference®, pp. 421–423, 449, 651, 935, 937, 1841, 2102, and 2419 (1995).

Rudel, L.L., *Plasma Liproproteins in Atherogenesis in Nonhuman Primates*, Kalter, S.S. (ed.), University of Texas Press, Austin, Texas, pp. 37–57 (1980).

Gregory, P.G.; "Cirrhosis of the Liver"; Mar. 1995; *Scientific American Medicine for Gastroenterology*.

*Primary Examiner*—Elli Peselev
*Attorney, Agent, or Firm*—Fish & Richardson, P.C.

[57] ABSTRACT

This invention is directed to a novel method for treating human patients with hypercholesterolemia with a macrolide antibiotic. More specifically, this invention is directed to the oral administration of an erythromycin compound or an erythromycin derivative for treating hypercholesterolemia. Most specifically, this invention teaches the novel oral administration of clarithromycin, troleandomycin, erythromycin, or azithromycin for treating human patients with hypercholesterolemia.

54 Claims, 77 Drawing Sheets

DATA FROM "PATIENT 1 CHOLESTEROL DATA"

DATA FROM "PT. 2 CHOLESTEROL DATA"

DATA FROM "PT. 3 CHOLESTEROL DATA"

DATA FROM "PT. 6 CHOLESTEROL DATA"

DATA FROM "PT 7 CHOLESTEROL DATA"

DATA FROM "PT 7 CHOLESTEROL DATA"

DATA FROM "PT. 9 CHOLESTEROL DATA"

DATA FROM "PT. 9 CHOLESTEROL DATA"

DATA FROM "PT. 10 CHOLESTEROL DATA"

DATA FROM "PT. 12 CHOLESTEROL DATA"

DATA FROM "PT. 14 CHOLESTEROL DATA"

DATA FROM "PT. 17 CHOLESTEROL DATA"

METHOD OF TREATING HYPERCHOLESTEROLEMIA WITH A MACROLIDE ANTIBIOTIC

CROSS REFERENCE TO RELATED APPLICATION

This application is related to the provisional application filed Jun. 28, 1995 having Ser. No. 60/000,583.

TECHNICAL FIELD OF THE INVENTION

This invention is related to co-pending United States patent application having Ser. No. 08/348,366 which was filed on Nov. 30, 1994, now U.S. Pat. No. 5,498,424, and is entitled "Method of Treating Obesity" (incorporated herein by reference).

This invention relates to methods and compositions for treating human patients diagnosed with hypercholesterolemia with a macrolide antibiotic. More specifically, this invention is directed to the oral administration of an erythromycin compound or an erythromycin derivative for treating hypercholesteremia. Most specifically, this invention teaches the novel oral administration of clarithromycin, troleandomycin, erythromycin, or azithromycin for treating human patients with hypercholesterolemia.

BACKGROUND OF THE INVENTION

One of the most prevalent disorders of lipid metabolism is hypercholesterolemia. Hypercholesterolemia has long been recognized as a significant risk factor for atherosclerotic disease. The causative factors in disorders of lipid metabolism include dietary factors, environmental factors (e.g. physical activity levels) and a variety of metabolic alterations.

BACKGROUND

Half of all deaths in the United States are caused by atherosclerosis. Atherosclerosis is a disease in which cholesterol accumulates in the wall of arteries, forms bulky plaques that inhibit the flow of blood, forms a clot eventually, obstructing an artery and eventually causes a heart attack or stroke. The cholesterol for the atherosclerotic plaque is derived from particles called low-density lipoprotein (LDL) that circulate in the bloodstream. In general, the more LDL there is in the blood, the more rapidly atherosclerosis develops.

Epidemiologic, clinical, genetic, experimental, and pathological studies have clearly established the primary role of lipoproteins in atherogenesis (i.e., the formation of atherosclerotic plaques). Lowering plasma cholesterol concentrations reduces the availability of atherogenic lipoproteins and presumably, the accumulation of cholesterol in the intima of arteries. Efforts to lower plasma cholesterol have become fundamental to the practice of preventative cardiology, and their use in both normal patients and those who already have coronary disease has materially contributed to the 50% reduction observed in mortality from coronary heart disease in the United States over the past two decades (Havel, et al, *Management of Primary Hyperlipidemia*, The New England Journal of Medicine, 332 (22):1491–1498 (1995)). The claimed invention is directed to lowering plasma cholesterol levels in patients diagnosed with hypercholesterolemia.

Lowering the plasma cholesterol concentration by a variety of means, including diet, partial ileal bypass surgery, and drug therapy, retards the progression of coronary plaques and promotes their regression. Although substantial regression is unusual and the change in average plaque size during and after treatment is small, the frequency of clinical coronary events is reduced out of proportion to the degree of anatomical change.

Epidemiologic data has revealed that more than half of the people in Western industrialized societies, including the United States, have a level of circulating low density lipoproteins ("LDL" discussed in detail below) associated with a high risk for developing atherosclerosis. These individuals are predisposed to accelerated atherosclerosis, heart attacks, and/or strokes.

The mechanism responsible for elevated LDL levels in many Americans has been identified by studies of specialized proteins called LDL receptors (See discussion below). The LDL receptors project from the surface of animal cells. The receptors bind LDL particles and extract them from the fluid that bathes the cells. The LDL is taken into the cells and cholesterol is metabolized to serve each cell's needs. In supplying cells with cholesterol and thereby removing LDL from the bloodstream, the receptors perform a second physiological function which is critical to the prevention of atherosclerosis.

The number of LDL receptors found on the surface of cells varies with the cellular demand for cholesterol. When the demand is low, excess cholesterol accumulates, cells make fewer receptors and LDL is "taken up" at a reduced rate. This mechanism protects cells against excess cholesterol accumulation. However, the reduction in the number of receptors and the consequent decrease in the rate at which LDL is removed from the blood circulation, results in elevated blood levels of LDL and an acceleration of atherosclerosis.

It has been hypothesized that the elevated plasma levels of LDL in many Americans is attributable to a combination of factors that diminish the production of LDL receptors. Recognition of the central role of the receptors has led to a treatment for a severe genetic form of atherosclerosis and has also shed light on the continuing controversy over the role of diet in atherosclerosis in the general population.

ATHEROSCLEROSIS AND ITS ASSOCIATED COMPLICATIONS

As stated above, atherosclerosis and its associated complications, particularly coronary heart and peripheral vascular diseases are a major health problems in human patients. Risk factors associated with the development of atherosclerosis and coronary heart disease include: (a) smoking; (b) diabetes mellitus; (c) hypertension; (d) a positive family history; and (e) plasma hypercholesterolemia. Among these risk factors, the level of certain plasma lipoproteins is an important factor that impacts the development of atherosclerosis. Elevated levels of LDL and reduced levels of high density lipoproteins ("HDL") are associated with more severe atherosclerosis and a greater risk of coronary heart disease in humans and experimental animals (Holme, I., Enger, S. C., Helgeland, A., Hjermann, I., Lerin, P., Lund-Larsen, P. G., Soleberg, L. A., and Strong, J. P.: *Risk factors and raised atherosclerotic lesions in coronary and cerebral arteries. Statistical analysis from the Oslo Study*. Arteriosclerosis 1:250–256, 1991; Kannel, W. B., Sorlie, P., Brand, F. Castelli, W. P., McNamara, P. M., Gherardi, G. J.: *Epidemiology of coronary atherosclerosis: Postmortem vs clinical risk factor correlation's. The Framingham Study.* In: Gotto, A. M., Jr., Smith, L. C., Allen, B., eds. International Symposium on atherosclerosis, 5th, Houston, 1079; Atherosclerosis V. New York Springer- Verlag, pp. 54–56, 1980; McGill, H. C., Jr. McMahan, C. A., Kruski, A. W., and Mott, G. E.: *Relationship of lipoprotein cholesterol concentrations to experimental atherosclerosis in baboons.* Arteriosclerosis 1:3–12, 1981; and Rudel L. L. In: The Use of Nonhuman Primates in Cardiovascular Disease. Kalter, S. S (ed.), University of Texas Press, Austin, Tex., pp. 37–57, 1980).

It is now known and widely accepted that lowering plasma LDL cholesterol levels reduces the risk of coronary heart disease in humans (Lipids Research Clinics Program. *The Lipid Research Clinics Coronary Primary Prevention Trial Results. I Reduction in incidence of coronary heart disease.* JAMA 251:351–364, 1984). The instant invention addresses this major health concern. A high fat and high cholesterol diet is a "way of eating" for far too many Americans. This invention relates to a method directed to an economical and novel way of treating hypercholesterolemia.

Most plaques are asymptomatic before infarction, reducing luminal diameter by less than fifty (50) percent. Coronary thrombosis is commonly caused by the fissuring of plaques, usually at the upstream margin. Fissure occurs mainly in areas where a thin fibrous cap overlies a poorly structured matrix that is rich in macrophage foam cells containing cholestryl esters. Lowering the cholesterol concentration reduces macrophage activity, reduces the accumulation of cholesterol, improves endothelial integrity and function, and thereby makes atherosclerotic lesions more stable and less likely to fissure.

In patients with coronary heart disease, lowering plasma cholesterol concentrations reduces mortality from coronary heart disease and from all causes. Although the evidence that the reduction of plasma cholesterol concentrations aids in the prevention of coronary heart disease is less compelling, there is little doubt that reducing cholesterol concentrations in the general population would lower both the incidence of and morality from coronary heart disease in the United States. In support of this contention the incidence of coronary heart disease and consequent mortality are substantially reduced in hypercholesterolemia patients treated with cholesterol-lowering diets and drugs. However, mortality from all causes is not significantly reduced, presumably because of limited statistical power to analyze this end point.

LOW-DENSITY LIPOPROTEIN CHOLESTEROL—BACKGROUND AND GENERAL INFORMATION

Concentrations of plasma total cholesterol and LDL cholesterol are highly positively correlated with the prevalence of coronary heart disease throughout the world. Observational studies of the incidence of disease have focused attention on the beneficial effects of lipid-lowering therapy in reducing both plasma LDL cholesterol concentrations and the frequency of clinical events. The emphasis placed on lowering plasma LDL cholesterol concentrations also reflects the increased risk of coronary heart disease in patients with heterozygous familial hypercholesterolemia. This disorder is characterized by elevated plasma LDL cholesterol concentrations and the early onset of coronary disease.

LDL cholesterol is a large spherical particle whose oily core is composed of some 1,500 molecules of the fatty alcohol cholesterol, each attached by an ester linkage to a long-chain fatty acid. This core of cholesterol esters is enclosed in a layer of phospholipid and unesterified cholesterol molecules. The phospholipids are arrayed so that their hydrophilic heads are on the outside, allowing the LDL to be dissolved in the blood or intercellular fluid. Embedded in this hydrophilic coat is one large protein molecule designated apoprotein B-100.

Apoprotein B-100 is recognized and bound by the LDL receptor, a glycoprotein (a protein to which sugar chains are attached). The receptor spans the cell's plasma membrane and carries a binding site which protrudes from the cell surface. Binding takes place when LDL is present at a concentration of less than $10^{-9}$ molar (i.e., the LDL receptor can pick out a single LDL particle from more than a billion molecules of water). The LDL receptor binds only lipoproteins carrying apoprotein B-100 and a related protein designated apoprotein E.

LDL receptors are clustered in specialized regions where the cell membrane is indented to form craters known as clarthrin-coated pits (because the inner surface of the membrane under them is coated with the protein clathrin). Within minutes of their formation, the pits pouch inward into the cell and pinch off from the surface to form membrane-bounded sacs called coated vesicles. LDL bound to a receptor is carried into the cell by this mechanism. Receptor-mediated endocytosis, the term applied to this process of uptake through coated pits and vesicles, is recognized as a mechanism for cells to envelope or take up many large molecules, each having its own highly specific receptor.

Eventually the LDL is separated from the receptor and the LDL is delivered to a lysosome which is a sac filled with digestive enzymes. The LDL receptor is recycled to the cell's surface to transport more LDL into the cell. Some of the lysosomal enzymes break down the LDL's coat, exposing the cholesterol ester core. Another enzyme clips off the fatty acid tails of the cholesterol esters, liberating unesterified cholesterol, which leaves the lysosome. All cells incorporate the cholesterol into newly synthesized surface membranes. In certain specialized cells the cholesterol extracted from LDL has other roles. For example, in the adrenal gland and ovary cholesterol is converted into the steroid hormones cortisol and estradiol, respectively. In addition, the liver transforms cholesterol into bile acids, which have a digestive function in the intestine.

PLASMA LIPOPROTEIN (a)—BACKGROUND

The plasma concentration of lipoprotein(a) or Lp(a), a complex LDL with a large glycoprotein (apoprotein(a)) is another independent risk factor for coronary heart disease. Lp(a) and other lipoprotein species that contain apoprotein B are found in atherosclerotic plaques in which they interact with proteoglycans in the arterial matrix and are subject to oxidative modification, possibly a key event in provoking inflammation and the deposition of cholesterol during atherogenesis.

PLASMA HDL CHOLESTEROL—BACKGROUND

A high plasma HDL cholesterol concentration is a powerful protective factor against coronary heart disease. HDLs, small lipoprotein particles that lack apoprotein B, are integral to the retrieval of cholesterol from cells and tissues (i.e., reverse cholesterol transport). High plasma HDL cholesterol concentrations, at least those accompanied by an increased concentration of apoprotein A-1, may reduce atherogenesis. Because HDL particles are polymorphic, measurement of HDL subpopulations could provide both improved measures of risk and more accurate assessment of the response of patients to treatment.

HYPERCHOLESTEROLEMIA

Hypercholesterolemia is one of the five major risk factors for the development of atherosclerotic disease. It has been estimated that complications of atherosclerosis account for up to 50% of all deaths in the United States. Hypercholesterolemia has been hypothesized to contribute to atherosclerosis by: (1) chemical injury to endothelial cells lining the intima of arteries; (2) stimulating adherence of monocytes and macrophages to the site of injury; and (3) providing increased lipid substrates for uptake by monocytes and arterial smooth muscle cells.

The risk of death from coronary artery disease has a continuous and graded relation to total serum cholesterol levels greater than 180 mg/dL. Moreover, the acceleration of atherosclerosis is positively correlated with elevations of LDL cholesterol. In contrast, elevation of high-density lipoprotein cholesterol HDL cholesterol has a negative correlation with atherosclerosis. Therefore, treatment regimes traditionally have been designed to reduce LDL cholesterol and/or elevate HDL cholesterol. These treatments include dietary intervention, exercise, and pharmacotherapy. Because many patients have difficulty achieving and maintaining a low-fat diet and a regular exercise program, drug therapy is wide-spread.

Drug treatment for hypercholesterolemia takes two principal forms: (1) resins which bind to bile acids and increase the utilization of endogenous cholesterol for bile acid synthesis (e.g., Cholestyramine and Cholestipol), and (2) compounds which alter the metabolism (e.g., synthesis, degradation, uptake or secretion) of various constituents within the cholesterol metabolic pathway (e.g., Lovastatin, Parvastatin, Simvastatin, Probucol, Gemfibrozil, and Niacin). Although these drugs are effective in reducing the levels of plasma cholesterol, they have a variety of undesirable side effects including: (1) elevation of plasma triglycerides; (2) increased liver aminotransferase activity; (3) abdominal discomfort, nausea, vomiting, diarrhea, and malaise; (4) QT interval prolongation; and (5) decreased high-density lipoprotein levels. (Fortmann, et al. *Disorders of Lipid Metabolism* in *Scientific American Medicine*, 9 Metabolism II: 14–15, 1993).

Endomycin, a polyenic macrolide antibiotic, has been previously used to alter lipid metabolism. U.S. Pat. No. 4,482,540 (Issued to Gordon et al on Nov. 13, 1984; incorporated herein by reference) is directed toward the oral administration of endomycin for altering lipid metabolism and reducing blood cholesterol levels. The Gordon invention is directed to a process for treating hypercholesterolemia in a mammal comprising the oral administration of an effective dose of endomycin to said mammal. The claimed invention is different from the Gordon invention in that the claimed invention utilizes an erythromycin compound or an erythromycin derivative for treating hypercholesterolemia. Additionally, one of ordinary skill in this art knows that erythromycin (or an erythromycin derivative) is structurally, and chemically different from endomycin (a polyenic macrolide antibiotic). The general class of polyenic macrolide compounds described in the Gordon invention are the hexaenes. The hexaene group of polyenic macrolides is relatively small in comparison to other groups. Representatives of this group are mediocidin, endomycin B (synonymous with Helixin B), cryptocidin and flavacid.

GENERAL TREATMENT FOR CHOLESTEROL REDUCTION

Implicit in screening is a commitment to provide appropriate advice and treatment. Causes of secondary hyperlipidemia must first be excluded. Dietary modification and increased physical activity not only reduce plasma cholesterol concentrations but also restrain the tendency of young Americans to gain weight. This tendency has been associated with plasma cholesterol concentrations that increase with age. Changes in diet and activity should be recommended most strongly to person at increased risk for cardiovascular disease because of high plasma non-HDL cholesterol value or other risk factors. A favorable response by young adults to nonpharmacologic treatment may make later drug therapy unnecessary.

The claimed invention offers a solution to the serious health problem facing most Americans eating a high fat and high cholesterol diet. The claimed invention is directed to a novel method for treating human patients diagnosed with hypercholesterolemia. The claimed invention treats hypercholesterolemia by giving an effective amount of an erythromycin compound or erythromycin derivative to a human patient diagnosed with hypercholesterolemia. The erythromycin compound or erythromycin derivative used in this invention include, but are not limited, to clarithromycin, troleandomycin, erythromycin, or azithromycin.

SUMMARY OF THE INVENTION

For this invention, dose and amount are used interchangeably. Also, hypercholesterolemia is clinically defined as a cholesterol level greater than 200 mg/dL, an HDL cholesterol level of less than 35 mg/dL, or an LDL cholesterol level of greater than 130 mg/dL. Also, "erythromycin" or an "erythromycin derivative" are used interchangeably and have the following meaning: a macrolide antibiotic which is a lipophilic molecule with a characteristic central lactone ring bearing 12 to 17 atoms, fewer than 5 and preferably no double bonds and preferably no nitrogen bonds. Several amino and/or neutral sugars are preferably fixed to the lactone ring. Examples of preferred erythromycin and erythromycin derivatives include: erythromycin, clarithromycin, azithromycin, and troleandomycin. Furthermore, in this invention, clarithromycin and Biaxin™ are used interchangeably. For example, ten (10) milligrams of Biaxin™ or ten (10) milligrams of clarithromycin per pound of body weight was administered to patients diagnosed with hypercholesterolemia at 48 hour intervals.

One aspect of this invention is a method of treating a human having hypercholesterolemia comprising administering to the human an effective dose for treating hypercholesterolemia of an erythromycin compound. In one embodiment of this method, the erythromycin compound is selected from the group consisting of clarithromycin, troleandomycin, erythromycin, and azithromycin. In a preferred embodiment, the dose is administered orally and ranges from 100 mg/day to 6,000 mg/day. In an alternative embodiment, the doses administered to the human by any known route and ranges from 1 mg/kg of body weight/day to 100 mg/kg of body weight/day.

An alternative aspect of this invention is a method of decreasing total plasma cholesterol levels in a human comprising administering to the human an effective dose for decreasing total plasma cholesterol levels of an erythromycin compound. In one embodiment of this method, the erythromycin compound is selected from the group consisting of clarithromycin, troleandomycin, erythromycin, and azithromycin. In a preferred embodiment, the dose is administered orally and ranges from 100 mg/day to 6,000 mg/day. In an alternative embodiment, the does is administered to the human by any known route and ranges from 1 mg/kg of body weight/day to 100 mg/kg of body weight/day.

An alternative aspect of this invention is a method of decreasing the ratio of plasma low-density lipoprotein cholesterol to plasma high-density lipoprotein cholesterol in a human comprising administering to the human an effective dose for decreasing the ratio of plasma low-density lipoprotein to plasma high-density lipoprotein of an erythromycin compound. In one embodiment, the erythromycin compound is selected from the group consisting of clarithromycin, troleandomycin, erythromycin, and azithromycin. In a preferred embodiment, the dose is administered orally and ranges from 100 mg/day to 6,000 mg/day. In an alternative embodiment, the dose is administered to the human by any known route and ranges from 1 mg/kg of body weight/day to 100 mg/kg of body weight/day.

An alternative aspect of this invention is a method of decreasing plasma low-density lipoprotein cholesterol levels in a human comprising administering to the human an effective dose for decreasing plasma low-density lipoprotein cholesterol levels of an erythromycin compound. In one embodiment, the erythromycin compound is selected from the group consisting of clarithromycin, troleandomycin, erythromycin, and azithromycin. In a preferred embodiment, the dose is administered orally and ranges from 100 mg/day to 6,000 mg/day In an alternative embodiment, the dose is administered to the human by any known route and ranges from 1 mg/kg of body weight/day to 100 mg/kg of body weight/day.

An alternative aspect of this invention is a method of increasing plasma high-density lipoprotein cholesterol levels in a human comprising administering to the human an effective dose for increasing plasma high-density lipoprotein cholesterol levels of an erythromycin compound. In one embodiment, the erythromycin compound is selected from the group consisting of clarithromycin, troleandomycin, erythromycin, and azithromycin. In a preferred embodiment, the dose is administered orally and ranges from 100 mg/day to 6,000 mg/day. In an alternative embodiment, the dose is administered to the human by any known route and ranges from 1 mg/kg of body weight/day to 100 mg/kg of body weight/day.

DESCRIPTION OF THE PREFERRED EMBODIMENTS

In its preferred embodiments, this invention involves novel methods to treat patients diagnosed with hypercholesterolemia.

The pharmaceutical compositions of the claimed erythromycin or erythromycin derivatives are formulated so as to be suitable for oral administration. The active ingredient (erythromycin or erythromycin derivatives) is contained in a capsule or tablet, preferably in enteric form. The quantity of effective dose supplied by each capsule or tablet is relatively unimportant since the total dosage can be reached by administration of either one or a plurality of capsules or tablets or both. The capsules employed may comprise any well known pharmaceutically acceptable material such as gelatin, cellulose derivatives, etc. The tablets may be formulated in accordance with conventional procedures well known to those skilled in the art which employ solid carriers, lubricants and the like. Examples of solid carriers are: starch, sugar, bentonite and other commonly used carriers.

DEFINITIONS

For the purpose of this invention, certain phrases and words are defined as follows:

1. "Dose" and "amount" (e.g., "effective dose") are interchangeably used;
2. Hypercholesterolemia is clinically defined as a cholesterol level greater than 200 mg/dL, or an HDL cholesterol level of less than 35 mg/dL, or an LDL cholesterol level of greater than 130 mg/dL or a total cholesterol/HDL cholesterol ratio of greater than 5.1 or an LDL/HDL ratio of greater than 3.7. Thus, any one of the above five determinants being "abnormal" is indicative of hypercholesterolemia.
3. "Erythromycin" or an "erythromycin derivative" are used interchangeably and have the following meaning: a macrolide antibiotic which is a lipophilic molecule with a characteristic central lactone ring bearing 12 to 17 atoms, fewer than 5 and preferably no double bonds and preferably no nitrogen bonds. Several amino and/or neutral sugars are preferably fixed to the lactone ring. Examples of preferred erythromycin and erythromycin derivatives include: erythromycin, clarithromycin, azithromycin, and troleandomycin.
4. Clarithromycin and Biaxin™ are used interchangeably. For example, ten (10) milligrams of Biaxin™ or ten (10) milligrams of clarithromycin per pound of body weight was administered to patients diagnosed with hypercholesterolemia at 24 or 48 hour intervals.
5. HDL=high-density lipoprotein; LDL=low-density lipoprotein; and ND=not determined.
6. 1 mg/kg/day=0.45 mg/lb/day; 100 mg/kg/day=45.0 mg/lb/day; 1.0 kg=2.222 lb; and 10 mg/lb=22.2 mg/kg.
7. "ccs" and "mls" are used interchangeably.

EXAMPLES

The following examples illustrate selected modes for carrying out the claimed invention and are not to be construed as limiting the specification and claims in any way. These examples are provided so as to enable those of ordinary skill in the art to make and use the invention. These examples are not intended to limit the scope of what the inventor regards as the invention. Efforts have been made to ensure accuracy with respect to numbers used to characterize the conditions; however, some experimental errors and deviations may be present.

EXAMPLE 1

Background Information on Erythromycin Compounds Macrolide Antibiotics and Macrolide-Like Antibiotics Macrolide antibiotics and macrolide-like antibiotics have been described by Bryskier, et al (Bryskier, A., Agouridas, C., and Chantot, J. F., *Structure and Activity in* THE NEW MACROLIDES, AZALIDES, AND STREPTOGRAMINS: PHARMACOLOGY AND CLINICAL APPLICATIONS, 3,3–11 [Neu, H. C., Young, L. S., and Zinner, S. H., eds., 1993]) and Omura (Omura, S., *Macrolide Antibiotics—Chemistry, Biology and Practice* 1984).

Macrolide antibiotics include, for example, those described by Bryskier et al, (e.g., a lipophilic molecule with a characteristic central lactone ring bearing 12 to 17 atoms, fewer than 5 and preferably no double bonds, preferably no nitrogen atoms and several amino and/or neutral sugars preferably fixed to the lactone ring). One group of somewhat atypical macrolide antibiotics are lankacidin derivatives, 17 membered-ring macrocyclic antibiotics which do not have sugars fixed to the aglycone ring. Another group of somewhat atypical macrolide antibiotics, are azalide compounds which contain an endocyclic nitrogen, namely azalide, within the aglycone ring.

Examples of macrolide antibiotics include the following synthetic, semi-synthetic or naturally occurring compounds:

methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the derivatives of these compounds. Thus, erythromycin and compounds derived from erythromycin belong to the general class of antibiotics known as "macrolides." Examples of preferred erythromycin and erythromycin-like compounds include: erythromycin, clarithromycin, azithromycin, and troleandomycin.

EXAMPLE 2

Erythromycin and Erythromycin Derivatives
Clarithromycin

In one aspect of the present invention, the erythromycin compound is clarithromycin.

Although the route of administration and dose will depend upon a variety of factors (e.g., treatment environment, patient compliance and tolerance, therapeutic goals, etc.), the preferred dose of clarithromycin taken orally ranges between 1 mg/kg of body weight/day and 100 mg/kg of body weight/day (i.e., approximately 100 mg/day to 6,000 mg/day).

Clarithromycin, also known as, 6-0-methylerythromycin, has the chemical formula, $C_{38}H_{69}NO_{13}$, and a molecular weight of 747.96 (see Physicians' Desk Reference®, 405–407, 1994). Clarithromycin is commercially available from Abbott Laboratories under the trademark "BIAXIN™", and is described, with other related erythromycin compounds in Watanabe, et al., U.S. Pat. No. 4,331,803 (which is incorporated herein by reference).

2. Azithromycin

In another aspect of the present invention, the erythromycin compound is azithromycin which is derived from erythromycin. It differs from erythromycin in that a methyl substituted nitrogen atom is incorporated into the lactone ring. Although the route of administration and dose will depend upon a variety of factors (e.g., treatment environment, patient compliance, patient tolerance, therapeutic goals, etc.), the preferred dose of azithromycin is taken orally and ranges between 1 mg/kg per body weight/day and 100 mg/kg of body weight/day (i.e., approximately 100 mg/day to 6,000 mg/day). Azithromycin, as a dihydrate, is a white crystalline powder with the chemical formula $C_{38}H_{72}N_2O_{12}2H_{2O}$ and a molecular weight of 785.0 (see Physician's Desk Reference®, 1789–91, 1994). Azithromycin is commercially available from Pfizer Laboratories Division under the trademark "ZITHROMAX™".

3. Troleandomycin

In another aspect of the present invention, the erythromycin compound is troleandomycin. Although the route of administration and dose will vary depending upon a variety of factors (e.g., treatment environment, patient compliance and tolerance, therapeutic goals, etc.), the preferred dose of troleandomycin is taken orally and ranges between 1 mg/kg of body weight/day and 100 mg/kg of body weight/day (i.e., approximately 100 mg/day to 6,000 mg/day). Troleandomycin has the chemical formula $C_{41}H_{67}NO_{15}$, and a molecular weight of 814 (see Physicians' Desk Reference®, 2102, 1995). Troleandomycin is commercially available from Pfizer Roerig Division under the trademark "TAO".

4. Erythromycin

In another aspect of the present invention, the erythromycin compound is erythromycin (i.e., including, but not limited to, erythromycin ethylsuccinate, erythromycin estolate, erythromycin stearate, erythromycin lactobionate).

Erythromycin is produced by a strain of Streptomyces erythrueus and belongs to the macrolide group of antibiotics. It is basic and readily forms salts with acids, but it is the base which is pharmacologically active. Although the route of administration and dose will depend upon a variety of factors (e.g., treatment environment, patient compliance, tolerance, therapeutic goal, etc.), the preferred dose of erythromycin is take orally and ranges between 1 mg/kg of body weight/day and 100 mg/kg of body weight/day (i.e., approximately 100 mg/day to 6,000 mg/day). Erythromycin has the chemical formula $C_{37}H_{67}NO_{13}$ and a molecular weight of 733.92 (see Physicians' Desk Reference®, 421–423, 425–427, 449, 651, 935, 937, 1841, and 2102, 1995). Erythromycin is commercially available from Abbott Laboratories, Boots Pharmaceuticals, Parke-Davis, Dista Products Company, Ross Laboratories, and Pfizer Roerig under a variety of trademark names, (e.g., "Erythromycin Delayed-Released Capsules (USP)™", E-Mycin™, ERYC™, Ilotycin™, Pediazole™, and TAO™).

EXAMPLE 3

Normal Plasma Cholesterol Levels

A preferred aspect of the present invention is a method of treating hypercholesterolemia which includes administering an effective dose or amount of an erythromycin or erythromycin derived compound to a human patient with a clinical diagnosis of hypercholesterolemia. Patients are diagnosed as being hypercholesterolemic when their plasma cholesterol levels are out of the "normal" range. Table 1 below lists the "normal" ranges for the cholesterol components or ratios that are monitored during the course of the patient's treatment with erythromycin or erythromycin derived compounds.

TABLE 1

| NORMAL PLASMA CHOLESTEROL LEVELS | |
|---|---|
| PLASMA COMPONENT OR RATIO | "NORMAL" PLASMA CONCENTRATION |
| Total Cholesterol | <200.0 mg/dL |
| HDL Cholesterol | >35.0 mg/dL |
| LDL Cholesterol | <130.0 mg/dL |
| Total Cholesterol/ HDL Cholesterol | <5.1 |
| LDL/HDL | <3.7 |

EXAMPLE 4

Therapeutic Administration of Erythromycin or Erythromycin Derived Compounds for Treating Hypercholesterolemia—in General A preferred aspect of the present invention is a method of treating hypercholesterolemia which includes administering an effective dose or amount of an erythromycin or erythromycin derived compound to a human patient with a clinical diagnosis of hypercholesterolemia.

A patient in need of treatment of hypercholesterolemia may be identified by measuring plasma cholesterol levels (e.g., total cholesterol, low-density lipoprotein cholesterol, high-density lipoprotein cholesterol, etc.) or by other standard diagnostic techniques (e.g., a family history of hypercholesterolemia, a patient history of atherosclerosis, etc.). For the purpose of this invention, hypercholesterolemia is defined as a cholesterol level greater than 200 mg/dL, an HDL cholesterol level of less than 35 mg/dL, an LDL cholesterol level of greater than 130 mg/dL, a total cholesterol: HDL cholesterol ratio of greater than 5.1 or a LDL cholesterol: HDL cholesterol ratio of greater than 3.7.

Following patient identification, a complete medical history is obtained with emphasis on potential adverse reactions to or contraindications for the use of erythromycin compounds. The desired reduction of total plasma cholesterol, the reduction of LDL cholesterol, the reduction of the LDL/HDL ratio, the reduction of the total plasma cholesterol/HDL ratio, and/or the elevation of HDL cholesterol is then determined based upon a comparison of the patient's present baseline plasma cholesterol levels with normative values and the physician's professional judgment. An effective dose or amount for treating hypercholesterolemia, the interval between doses, and the duration of treatment are then determined on a case-by-case basis. Once informed patient consent is obtained, Biaxin™ treatment is initiated. The patient is followed at appropriate intervals during treatment (usually weekly) and measurements of plasma cholesterol, updating patient histories, and dose modification, if necessary, are performed (as determined by the clinician).

EXAMPLE 5

Effect of Clarithromycin on Plasma Cholesterol

An aspect of this invention is a novel method of treating hypercholesterolemia. Yet another preferred aspect of the present invention is a method of treating a patient with hypercholesterolemia which includes the administration of an effective amount of an erythromycin compound. Many different erythromycin compounds or erythromycin derived compounds are known to those skilled in this art but the inventor prefers to use erythromycin, clarithromycin, azithromycin, or troleandomycin.

A patient in need of treatment for hypercholesterolemia may be identified by measuring plasma levels of cholesterol, HDL cholesterol, and LDL cholesterol or by other standard diagnostic techniques. For the purpose of this invention, hypercholesterolemia is defined as a total cholesterol level greater than 200 mg/dL, an HDL cholesterol level of less than 35 mg/dL, an LDL cholesterol level of greater than 130 mg/dL, a total cholesterol: HDL cholesterol ratio of less than 5.1 or an LDL cholesterol: HDL cholesterol ratio of less than 3.7. Following patient classification, a complete medical history is obtained with emphasis on potential adverse reactions to or contraindications for the use of erythromycin compounds. Five milliliters of blood are drawn from the patient and baseline plasma levels of total cholesterol, HDL cholesterol, and LDL cholesterol are determined. The desired reduction of plasma cholesterol levels is then determined based upon a comparison of the patient's present plasma levels with normative values and the physician's professional judgment. An effective dose for treating hypercholesterolemia, the interval between doses, and the duration of treatment are then determined. Once informed patient consent is obtained. Biaxin™ treatment is initiated. The patient is followed at appropriate intervals during treatment (usually weekly) and measurements of plasma levels for total cholesterol, HDL cholesterol and LDL cholesterol, patient histories, and dose modification, if necessary, are performed.

Once diagnosed as hypercholesterolemic, the patient was entered into the study. Twenty one patients, each diagnosed with hypercholesterolemia, have been treated with clarithromycin (10 mg/pound of body weight at 48 hour intervals from 8 to 45 days; see individual patient data for exact number of days on Biaxin™). For the purpose of this invention, hypercholesterolemia is defined as a cholesterol level greater than 200 mg/dL, an HDL cholesterol level of less than 35 mg/dL, an LDL cholesterol level of greater than 130 mg/dL, a total cholesterol: HDL cholesterol ratio of less than 5.1 or an LDL cholesterol: HDL cholesterol ratio of less than 3.7 Five milliliters (ccs) of blood was drawn from each patient on the days indicated and plasma levels of cholesterol, HDL cholesterol and LDL cholesterol were determined for each patient. The data was then analyzed and the percent change over time was calculated.

General Information Given to Each Patient Beginning Biaxin Treatment

As stated above, informed consent was obtained from all patients with regard to the potential benefits and risks of the experimental protocol. Patients were informed that clarithromycin had not been approved by the F.D.A. for the treatment of hypercholesterolemia. The observations with regard to cholesterol were made as part of a larger clinical trial for the treatment of obesity with clarithromycin (subject matter of co-pending United States patent application having Ser. No. 08/348,366 which was filed on Nov. 30, 1994 and is entitled "Method of Treating Obesity" [incorporated herein by reference]).

All current medications were reviewed in detail for each patient by the clinician. Patients on certain medications or with histories of certain diseases were excluded from participation in the trial.

A physical examination was performed on all patients. Hypertension is extremely common in this patient population. Patients on angiotensin conversion enzyme (ACE) inhibitors were transferred to an alpha blocker, prazosin, if they were diabetic, and to a beta blocker, atenolol, if they were not diabetic. Beta blockers should be avoided with diabetes mellitus as they may hide the symptoms of hypoglycemia. Diabetes is quite common in this population. Optimum control of diabetes was provided with either insulin, or oral hypoglycemic medication where indicated.

All patients had a complete CBC and SMA-29 work-up on the days indicated on Table 2 (usually weeks 0, 1, 2, 3, 4 or day 1, 8, 15, 22, and 29) and every 4 weeks thereafter. For the CBC work-up, 5 milliliters of blood were drawn into a Vacutainer™ with 0.05 ml of 15% EDTA (K3) solution (7.5 mg). There was no interior coating, the tube had a silicone lubricated stopper and a lavender top for identification. For the SMA-29 work-up 5 milliliters of blood were drawn into an empty Vacutainer™ with a red top for identification. The blood was centrifuged and the results were obtained by examination of the serum by an automated processor. These automated processors are readily available through routine laboratory services provided to all physicians. The automated processors are calibrated and routinely checked and re-calibrated.

In general, each patient received one dose of clarithromycin every 48 hours. The dose provided was 10 mg per pound (22.2 mg per kilogram). Because clarithromycin is available by prescription as 500 mg tablets, most patients receive a single dose of 500 mg per 50 pounds of body weight on each day of treatment. The dose may be modified (increased or decreased) by the physician as a result of the patient's response to treatment.

The inventor observed that women develop nausea more frequently with ingestion of clarithromycin than men. Thus, all women were instructed to take a 250 mg tablet of Tigan™ (See Physicians' Desk Reference, page 2419, 1995) upon awakening the day that clarithromycin was to be taken. In addition, all women were instructed to wait 30 minutes before taking the full dose of clarithromycin. The medication is taken with water only and is not to be taken with food. Men were instructed to take the medication upon awakening without food.

Patients were informed that they may have a bad taste in their mouth as a result of the medication. Although this bad taste has a beneficial effect of reinforcing a decrease of food intake, patients were also told that additional side effects (abdominal cramps, nausea, diarrhea) may occur during the first and second doses. In addition, some patients report one or two loose bowel movements within 4 hours of taking the medication. These symptoms generally decrease thereafter with continued use. Patients were also informed that if there is any suspicion of an allergic reaction (e.g., hives, skin rash, difficulty breathing) they should call their physician immediately. Any persistent diarrhea, fever or rectal bleeding should also be evaluated as soon as possible.

Since weight control is critical to maintaining normal cholesterol levels, all patients are advised regarding eating habits and food intake. Regarding dietary instructions, the patients were advised to avoid ingestion of bread, potatoes, deserts, and snacks. With most patients, simplicity of instructions is important. A weekly check-up with monitoring of weight, blood pressure, and blood tests allows the physician to reinforce the importance of diet to help improve their health. The medication was discontinued if any significant abnormalities on the blood tests arise. In particular, the physician would monitor for indications of hepatic or renal dysfunction and a decrease of the white blood cell or platelet count as these can indicate rare side effects of the medication.

During the discussion about dieting, the patient is also provided with basic information regarding the mechanism behind successful weight loss. In addition, how to maintain weight loss is explained to each patient. Individuals not able to maintain weight loss may lack the effect in the brain to turn off the desire to ingest further food when it is not needed. Recent studies with regard to the obesity gene demonstrate that a protein is produced by fat cells, the ob protein that normally attaches to a brain receptor site. The effect of this is to create a sensation of satiety and turn off the desire to eat further. Obese individuals produce a defective protein that fails to attach to the receptor site in the brain. These individuals continue to consume more food than would otherwise be warranted. It is well known to those skilled in the art that obesity raises serum cholesterol and food high in cholesterol content will increase the serum cholesterol.

Apart from decreased food consumption, clarithromycin may act independently to decrease total cholesterol, increase the HDL cholesterol, decrease the LDL cholesterol, reduce the cholesterol/HDL and LDL/HDL ratios (See Furuchi, et al, *Bafilomycin A1, A Specific Inhibitor or Vacuolar-type H+-ATPase, Blocks Lysosomal Cholesterol Trafficking in Macrophages*, Journal of Biological Chemistry, 268:27345–27348, 1993 and Kawashima, et al, *New Cholesterol Biosynthesis Inhibitors . . .* , Journal of Antibiotics, 45(1):207–212, (1992)). As described above, these effects decrease the risk for complications of atherosclerosis, coronary artery disease (heart attack), cerebrovascular disease (stroke), and peripheral vascular disease.

Once normal plasma cholesterol levels and ideal body weight have been achieved, clarithromycin may be discontinued or the patient may be continued on it as prophylactic therapy. The resetting of the hypothalamic thermostat may persist for some time after cessation of taking of the medication and the duration of maintenance of normal cholesterol levels (and maintained weight loss) without medication will be determined on a case-by-case basis. The cholesterol levels are monitored closely after cessation of medication to determine if further treatment were indicated.

The results for the 21 patients are shown in Table 2. All 21 patients received 10 milligrams of Biaxin™ per pound of body weight at 24 or 48 hour intervals. General conclusions after fifteen (15) days of Biaxin treatment for these initial 21 patients are that:

1. Total cholesterol level decreased by $\geq 10\%$ in 5 out of 19 patients (26%).
2. Total high density lipoprotein cholesterol level increased by $\geq 10\%$ in 8 out of 19 patients (42%).
3. Total low density lipoprotein cholesterol level decreased by $\geq 10\%$ in 5 out of 19 patients (26%).

The results for the 21 patients demonstrating a favorable response of 10% or greater in any one of the determining five categories as of the date of their most recent Biaxin treatment (but not final Biaxin treatment) is presented in the Table below. An "X" in the box labeled "Cholesterol" indicates that the patient demonstrated a 10% or greater reduction in total cholesterol levels as of their most recent Biaxin treatment. An "X" in the box labeled "HDL" indicates that the patient demonstrated a 10% or greater increase in HDL levels as of their most recent Biaxin treatment. An "X" in the box labeled "LDL" indicates that the patient demonstrated a 10% or greater reduction in LDL levels as of their most recent Biaxin treatment. An "X" in the box labeled "C/HDL" indicates that the patient demonstrated a 10% or greater reduction in cholesterol/HDL ratio as of their most recent Biaxin treatment. An "X" in the box labeled "LDL/HDL" indicates that the patient demonstrated a 10% or greater reduction in LDL/HDL ratio as of their most recent Biaxin treatment. Note that Patient 10 was never diagnosed as hypercholesterolemic, was treated with Biaxin for his obesity and was inadvertently added to this Table. Also, Patients 3 and 18 showed no clinical improvement while on the Biaxin treatment.

General conclusions for the 20 patients on Biaxin treatment at the time this application was filed with the United States Patent and Trademark Office are:

1. Eight out 20 (40%) demonstrated a reduction in total cholesterol levels of 10% or more.
2. Ten out of 20 (50%) demonstrated an increase in HDL level of 10% or more.
3. Eight out of 20 demonstrated a reduction in LDL levels of 10% or more.
4. Fourteen out of 20 (70%) demonstrated a reduction in cholesterol/HDL ratio of 10% or more.
5. Twelve out of 20 (60%) demonstrated a reduction in LDL/HDL ratio of 10% or more.

| | Overall Response For The 21 Patients As Of Most Recent Biaxin Treatment | | | | |
|---|---|---|---|---|---|
| Pt. # | Cholesterol | HDL | LDL | C/HDL | LDL/HDL |
| 1 | | X | | X | X |
| 2 | X | | X | | |
| 3 | — | — | — | — | — |
| 4 | X | | X | X | X |

-continued

Overall Response For The 21 Patients As Of Most Recent Biaxin Treatment

| Pt. # | Cholesterol | HDL | LDL | C/HDL | LDL/HDL |
|---|---|---|---|---|---|
| 5 | X |   | X | X | X |
| 6 | X | X | X | X | X |
| 7 |   | X |   | X |   |
| 8 |   | X | X | X | X |
| 9 | X | X |   | X |   |
| 10 | — | — | — | — | — |
| 11 |   | X | X | X | X |
| 12 |   | X |   |   |   |
| 13 |   |   |   | X | X |
| 14 | X |   | X |   | X |
| 15 | X |   |   | X | X |
| 16 | X |   |   |   |   |
| 17 |   |   |   | X |   |
| 18 | — | — | — | — | — |
| 19 |   | X | X | X | X |
| 20 |   | X |   | X | X |
| 21 |   | X |   | X | X |

EXAMPLE 6

Patient 1 Demonstrating Reduction in Plasma Cholesterol Levels During Course of Biaxin Treatment Patient 1, a 44 year old white female was diagnosed as hypercholesterolemic and began Biaxin™ treatment every other day for 24 days. This patient's data are presented in Table 2 and the data are graphed in FIGS. 1A to 1D.

This patient demonstrated a 3.2% change in total cholesterol levels, a 38.9% change in HDL cholesterol levels and a –3.6% change in LDL cholesterol levels.

EXAMPLE 7

Patient 2 Demonstrating Reduction in Plasma Cholesterol Levels During Course of Biaxin Treatment Patient 2, a 47 year old hispanic female was diagnosed as hypercholesterolemic and began Biaxin™ treatment every other day for 29 days. This patient's data are presented in Table 2 and the data are graphed in FIGS. 2A to 2D.

This patient demonstrated a –13.3% change in total cholesterol levels, a –20.5% change in HDL cholesterol levels and a –16.9% change in LDL cholesterol levels.

EXAMPLE 8

Patient 3 Demonstrated No Reduction in Plasma Cholesterol Levels During Course of Biaxin Treatment Patient 3, a 66 year old white male was diagnosed as hypercholesterolemic and began Biaxin™ treatment every other day for 8 days. This patient's data are presented in Table 2 and the data are graphed in FIGS. 3A to 3D.

This patient demonstrated a –5.7% change in total cholesterol levels, a –4.7% change in HDL cholesterol levels and a 12.2% change in LDL cholesterol levels. This patient showed no clinical improvement while on the Biaxin treatment.

EXAMPLE 9

Patient 4 Demonstrating Reduction in Plasma Cholesterol Levels During Course of Biaxin Treatment Patient 4, a 50 year old white male was diagnosed as hypercholesterolemic and began Biaxin™ treatment every other day for 22 days. Of interest, this patient has been followed since mid-1986 and has been consistently diagnosed as hypercholesterolemic. Over the last eight to nine (8–9) years, Patient 4 was placed on different cholesterol reducing medications with little or no success observed. As noted below, this patient demonstrated marked improvement after only 22 days on Biaxin treatment. This patient's data are presented in Table 2 and the data are graphed in FIGS. 4A to 4D.

This patient demonstrated a –29.1% change in total cholesterol levels, a –12.2% change in HDL cholesterol levels and a –30.3% change in LDL cholesterol levels.

EXAMPLE 10

Patient 5 Demonstrating Reduction in Plasma Cholesterol Levels During Course of Biaxin Treatment Patient 5, a 38 year old white female was diagnosed as hypercholesterolemic and began Biaxin™ treatment every other day for 33 days. This patient's data are presented in Table 2 and the data are graphed in FIGS. 5A to 5D.

This patient demonstrated a –13.3% change in total cholesterol levels, a 0.0% change in HDL cholesterol levels and a –11.0% change in LDL cholesterol levels.

EXAMPLE 11

Patient 6 Demonstrating Reduction in Plasma Cholesterol Levels During Course of Biaxin Treatment Patient 6, a 58 year old white male was diagnosed as hypercholesterolemic and began Biaxin™ treatment every other day for 29 days. This patient's data are presented in Table 2 and the data are graphed in FIGS. 6A to 6D.

This patient demonstrated a –22.6% change in total cholesterol levels, a 28.6% change in HDL cholesterol levels and a –23.0% change in LDL cholesterol levels.

EXAMPLE 12

Patient 7 Demonstrating Reduction in Plasma Cholesterol Levels During Course of Biaxin Treatment Patient 7, a 65 year old white male was diagnosed as hypercholesterolemic and began Biaxin™ treatment every other day for 42 days. Note that, due to patient error, this patient did not take Biaxin for one week (off Biaxin on day 14 and began Biaxin again on day 22). This patient's data are presented in Table 2 and the data are graphed in FIGS. 7A to 7D.

This patient demonstrated a –3.9% change in total cholesterol levels, a 18.5% change in HDL cholesterol levels and a 10.0% change in LDL cholesterol levels.

EXAMPLE 13

Patient 8 Demonstrating Reduction in Plasma Cholesterol Levels During Course of Biaxin Treatment Patient 8, a 49 year old white male was diagnosed as hypercholesterolemic and began Biaxin™ treatment every other day for 22 days. This patient's data are presented in Table 2 and the data are graphed in FIGS. 8A to 8D.

This patient demonstrated a –2.1% change in total cholesterol levels, a 26.9% change in HDL cholesterol levels and a –11.5% change in LDL cholesterol levels.

EXAMPLE 14

Patient 9 Demonstrating Reduction in Plasma Cholesterol Levels During Course of Biaxin Treatment Patient 9, a 39 year old white male was diagnosed as hypercholesterolemic and began Biaxin™ treatment every other day for 66 days. Note that this patient was off Biaxin on days 53–60 and resumed Biaxin treatment on day 61. This patient's data are presented in Table 2 and the data are graphed in FIGS. 9A to 9D.

This patient demonstrated a −13.4% change in total cholesterol levels, a 15.6% change in HDL cholesterol levels and a 30.1% change in LDL cholesterol levels.

EXAMPLE 15

Patient 10 Demonstrating No Reduction in Plasma Cholesterol Levels During Course of Biaxin Treatment Patient 10, a 47 year old white male, was not diagnosed as hypercholesterolemic, but began Biaxin™ treatment every other day for 29 days to treat his obesity. This patient's data are presented in Table 2 and the data are graphed in FIGS. 10A to 10C.

This patient demonstrated a 10.4% change in total cholesterol levels, a 5.6% change in HDL cholesterol levels and a 40.4% change in LDL cholesterol levels. This patient showed no clinical improvement because he was not hypercholesterolemic at the onset of Biaxin therapy.

EXAMPLE 16

Patient 11 Demonstrating Reduction in Plasma Cholesterol Levels During Course of Biaxin Treatment Patient 11, a 48 year old white female was diagnosed as hypercholesterolemic and began Biaxin™ treatment every other day for 43 days. This patient's data are presented in Table 2 and the data are graphed in FIGS. 11A to 11D.

This patient demonstrated a −8.8% change in total cholesterol levels, a 12.5% change in HDL cholesterol levels and a −14.0% change in LDL cholesterol levels.

EXAMPLE 17

Patient 12 Demonstrating Reduction in Plasma Cholesterol Levels During Course of Biaxin Treatment Patient 12, a 47 year old white female was diagnosed as hypercholesterolemic and began Biaxin™ treatment every other day for 22 days. This patient's data are presented in Table 2 and the data are graphed in FIGS. 12A to 12C.

This patient demonstrated a 5.9% change in total cholesterol levels, a 17.1% change in HDL cholesterol levels and a 39.0% change in LDL cholesterol levels.

EXAMPLE 18

Patient 13 Demonstrating Reduction in Plasma Cholesterol Levels During Course of Biaxin Treatment Patient 13, a 51 year old white male was diagnosed as hypercholesterolemic and began Biaxin™ treatment every other day for 22 days. This patient was off of Biaxin from days 23–57 during which time he was still monitored for plasma cholesterol levels. Note that the reduction of the total cholesterol/HDL ratio was maintained while the patient was off Biaxin. At day 22: total cholesterol was reduced by 7.18%, HDL levels increased by 9.68%, LDL levels decreased by 6.25%, cholesterol/HDL ration was reduced by 15.5% (still reduced by 13.7% at day 57 following 34 days off Biaxin), LDL/HDL ratio was reduced by 14.6% (still reduced 7.3% at day 57 following 34 days off Biaxin). This patient's data are presented in Table 2 and the data are graphed in FIGS. 13A to 13C.

This patient demonstrated a 29.3% change in total cholesterol levels, a 48.4% change in HDL cholesterol levels and a 35.9% change in LDL cholesterol levels.

EXAMPLE 19

Patient 14 Demonstrating Reduction in Plasma Cholesterol Levels During Course of Biaxin Treatment Patient 14, a 40 year old white male was diagnosed as hypercholesterolemic and began Biaxin™ treatment every other day for 15 days. This patient's data are presented in Table 2 and the data are graphed in FIGS. 14A to 14C.

This patient demonstrated a −20.9% change in total cholesterol levels, a −14.7% change in HDL cholesterol levels and a −36.9% change in LDL cholesterol levels.

EXAMPLE 20

Patient 15 Demonstrating Reduction in Plasma Cholesterol Levels During Course of Biaxin Treatment Patient 15, a 38 year old white female was diagnosed as hypercholesterolemic and began Biaxin™ treatment every other day for 29 days. This patient's data are presented in Table 2 and the data are graphed in FIGS. 15A to 15D.

This patient demonstrated a −11.0% change in total cholesterol levels, a 9.1% change in HDL cholesterol levels and a −5.7% change in LDL cholesterol levels.

EXAMPLE 21

Patient 16 Demonstrating Reduction in Plasma Cholesterol Levels During Course of Biaxin Treatment Patient 16, a 52 year old white male was diagnosed as hypercholesterolemic and began Biaxin™ treatment every other day for 15 days. This patient's data are presented in Table 2 and the data are graphed in FIGS. 16A to 16D.

This patient demonstrated a −22.4% change in total cholesterol levels, a −26.0% change in HDL cholesterol levels and a −6.8% change in LDL cholesterol levels.

EXAMPLE 22

Patient 17 Demonstrating Reduction in Plasma Cholesterol Levels During Course of Biaxin Treatment Patient 17, a 43 year old white female was diagnosed as hypercholesterolemic and began Biaxin™ treatment every other day for 22 days. This patient's data are presented in Table 2 and the data are graphed in FIGS. 17A to 17D.

This patient demonstrated a −4.2% change in total cholesterol levels, a 8.1% change in HDL cholesterol levels and a 1.2% change in LDL cholesterol levels.

EXAMPLE 23

Patient 18 Demonstrated No Reduction in Plasma Cholesterol Levels During Course of Biaxin Treatment Patient 18, a 46 year old black female was diagnosed as hypercholesterolemic and began Biaxin™ treatment every other day for 15 days. This patient's data are presented in Table 2 and the data are graphed in FIGS. 18A to 18C.

This patient demonstrated a 4.5% change in total cholesterol levels, a −3.9% change in HDL cholesterol levels and a 5.7% change in LDL cholesterol levels. This patient showed no clinical improvement on the Biaxin treatment.

EXAMPLE 24

Patient 19 Demonstrating Reduction in Plasma Cholesterol Levels During Course of Biaxin Treatment Patient 19, a 36 year old white female was diagnosed as hypercholesterolemic and began Biaxin™ treatment every other day for 15 days. This patient's data are presented in Table 2 and the data are graphed in FIGS. 19A to 19D.

This patient demonstrated a −2.8% change in total cholesterol levels, a 21.2% change in HDL cholesterol levels and a −16.2% change in LDL cholesterol levels.

EXAMPLE 25

Patient 20 Demonstrating Reduction in Plasma Cholesterol Levels During Course of Biaxin Treatment Patient 20, a 48 year old white male was diagnosed as hypercholesterolemic and began Biaxin™ treatment every other day for 22 days. This patient's data are presented in Table 2 and the data are graphed in FIGS. 20A to 20C.

This patient demonstrated a 0.4% change in total cholesterol levels, a 36.7% change in HDL cholesterol levels and a 0.0% change in LDL cholesterol levels.

EXAMPLE 26

Patient 21 Demonstrating Reduction in Plasma Cholesterol Levels During Course of Biaxin Treatment Patient 21, a 38 year old white female was diagnosed as hypercholesterolemic and began Biaxin™ treatment every other day for 15 days. This patient's data are presented in Table 2 and the data are graphed in FIGS. 21A to 21C.

This patient demonstrated a 13.8% change in total cholesterol levels, a 53.1% change in HDL cholesterol levels and a −3.3% change in LDL cholesterol levels.

EXAMPLE 27

Supplementing Livestock Feed With Erythromycin Compounds to Produce Meats Containing Reduced Cholesterol Levels Since the average American person needs to reduce their total dietary cholesterol intake, raising livestock (e.g., including, but not limited to, cows, pigs, sheep, goats, chickens, turkeys, ducks, and the like) with a reduced cholesterol level would help reduce dietary cholesterol intake. Raising livestock and therefore producing meat with a reduced cholesterol level could be accomplished by supplementing livestock feeds with Biaxin™ (for example, 10 to 1000 milligrams of Biaxin™ per pound of livestock weight). Livestock would be raised on Biaxin™ supplemented feed and during their growth stages, plasma cholesterol levels could be monitored in order to determine the amount of Biaxin™ to be used in the supplement, the duration of supplementing the cattle feed with Biaxin™ and side effects (if any). Raising livestock containing a reduced cholesterol level will address one of the average American's major health concerns which is to reduce dietary cholesterol intake.

Livestock will be fed Biaxin™ supplemented feed and their plasma cholesterol levels will be monitored during their development. Different factors that will be studied in order to determine the dose of Biaxin™ to be added to supplement the livestock feed are: (1) the amount of Biaxin™ to be used in the supplement, (2) the duration of supplementing the feed with Biaxin™ and (3) the side effects (if any).

REFERENCES

Figure 1A:
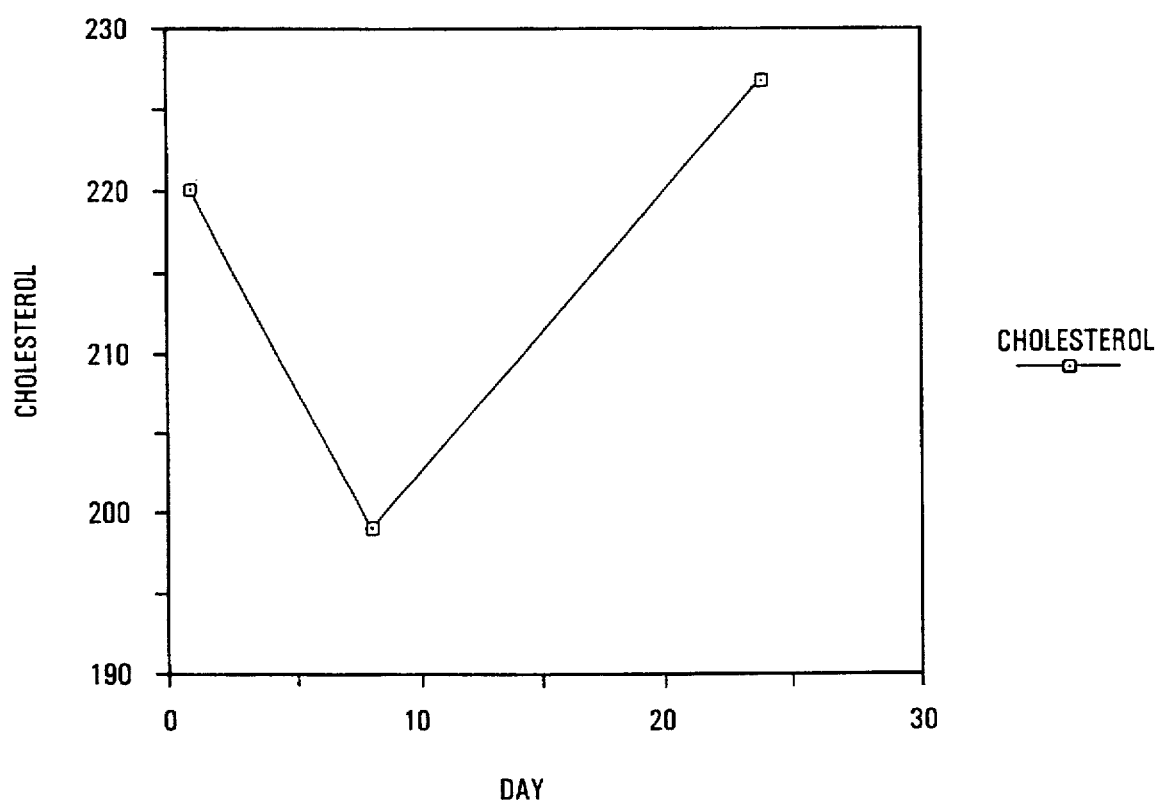
FIGS. 1–9 Panels A–D detail plasma cholesterol levels for Patients #1–#9, respectively.
Figure 1B:
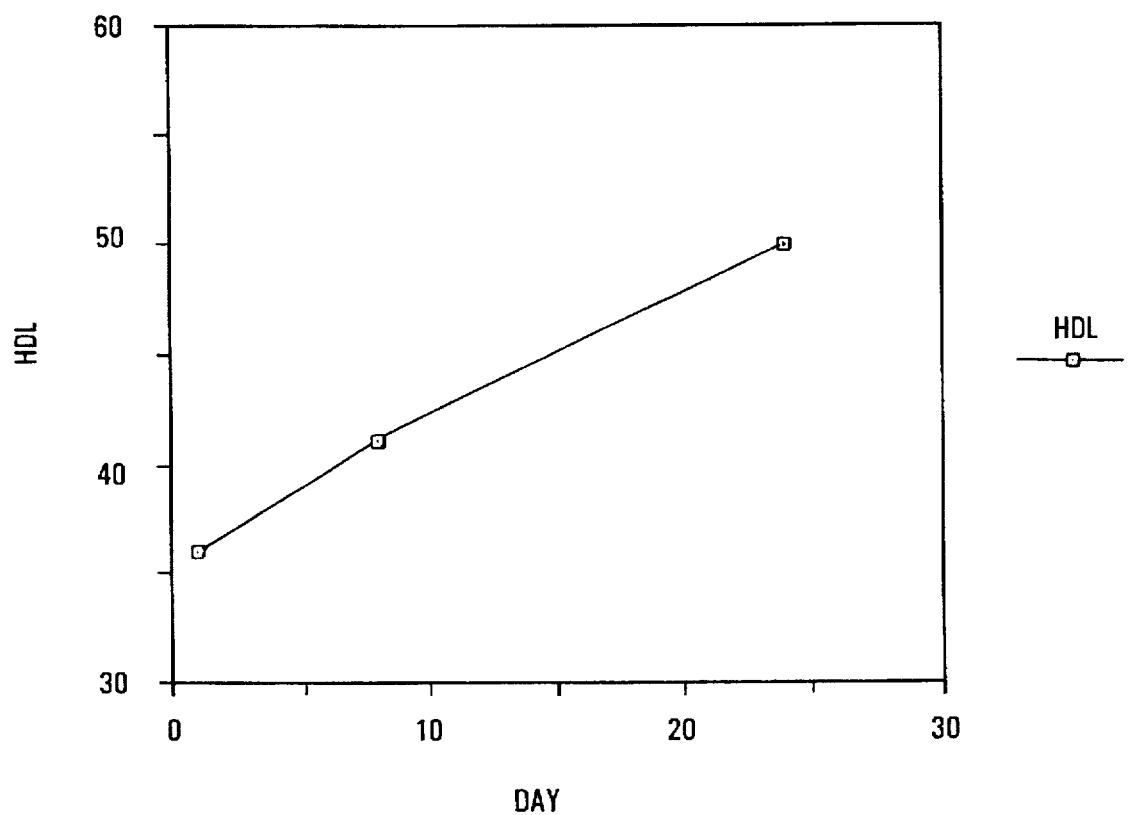
Figure 1C:
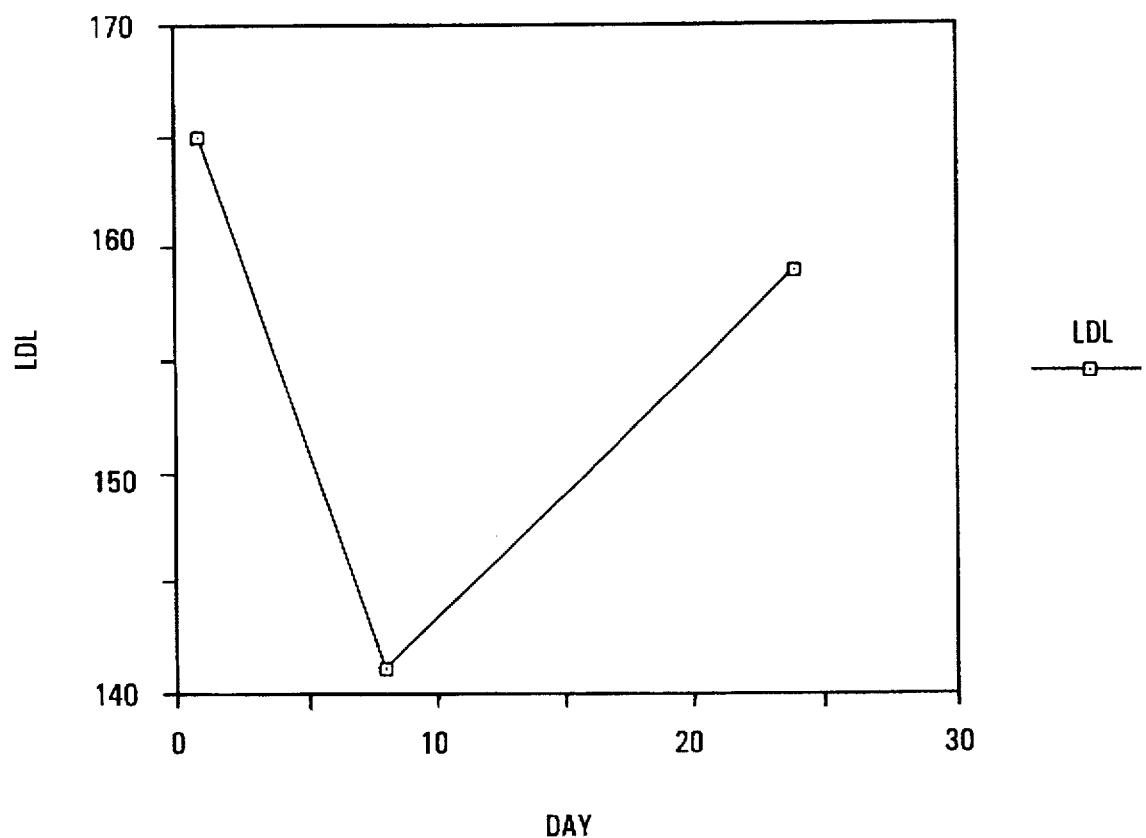
Figure 1D:
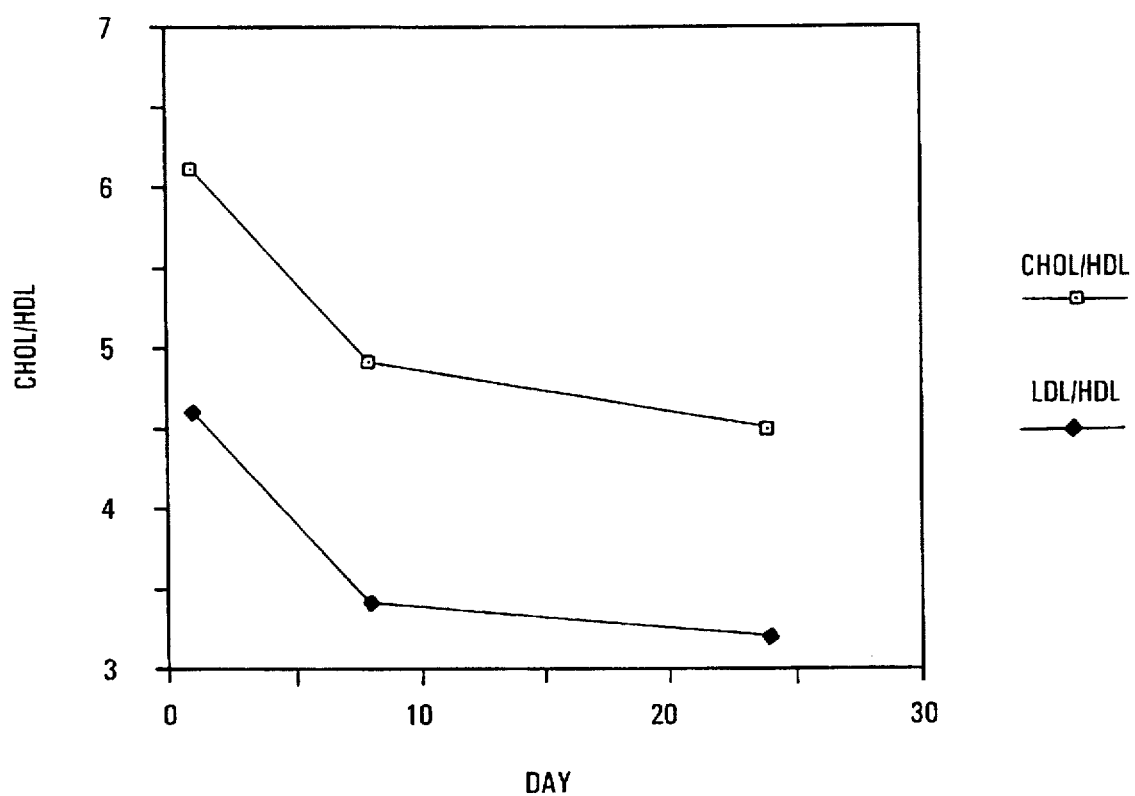
Figure 2A:
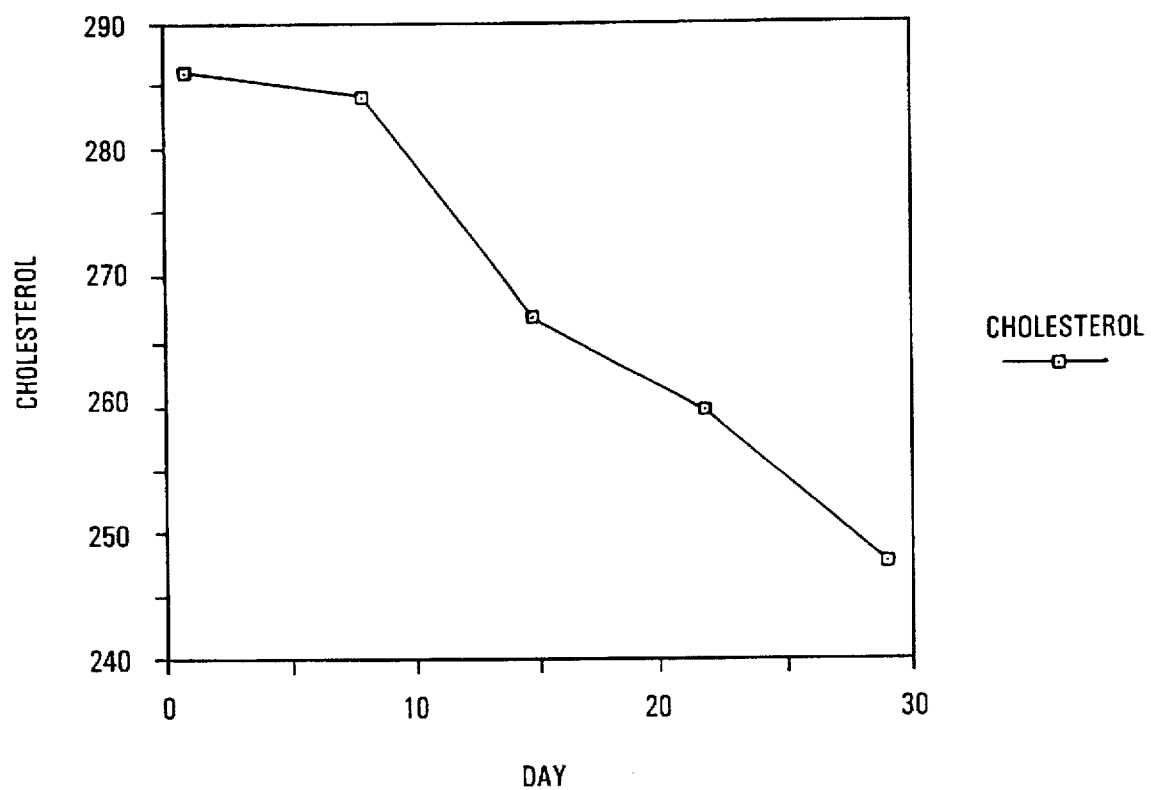
Figure 2B:
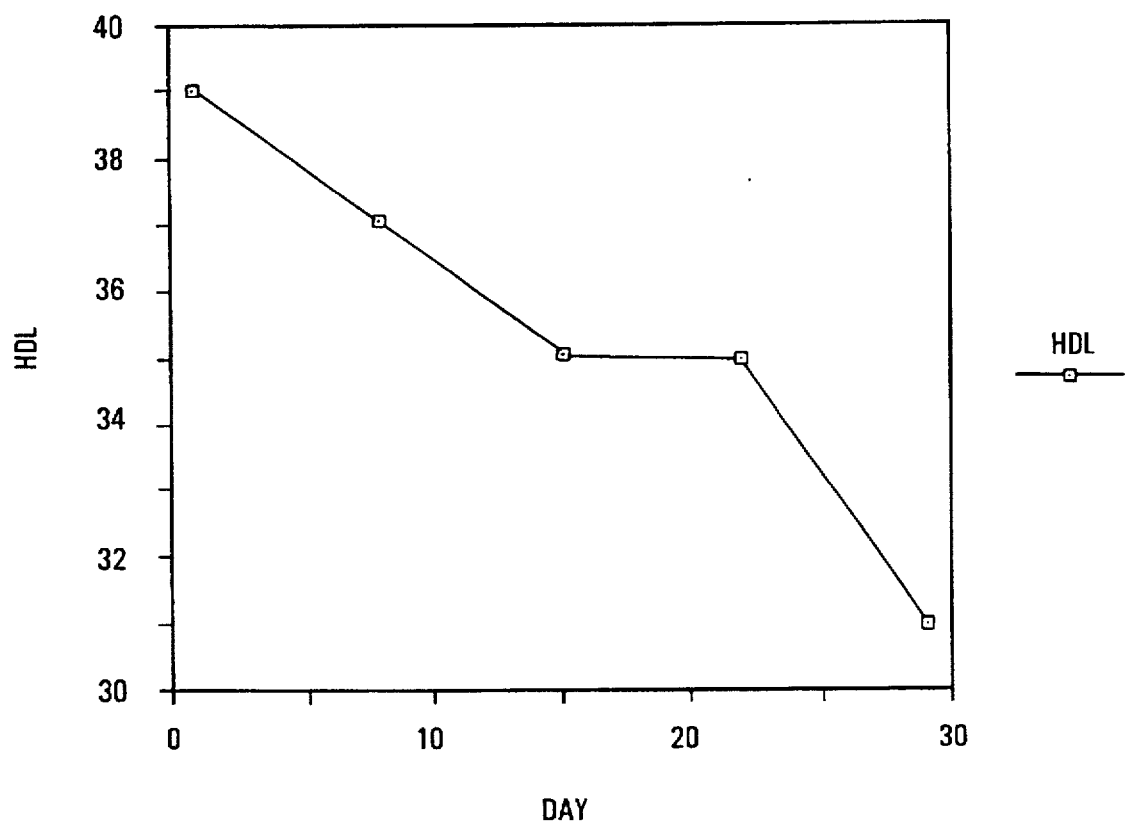
Figure 2C:
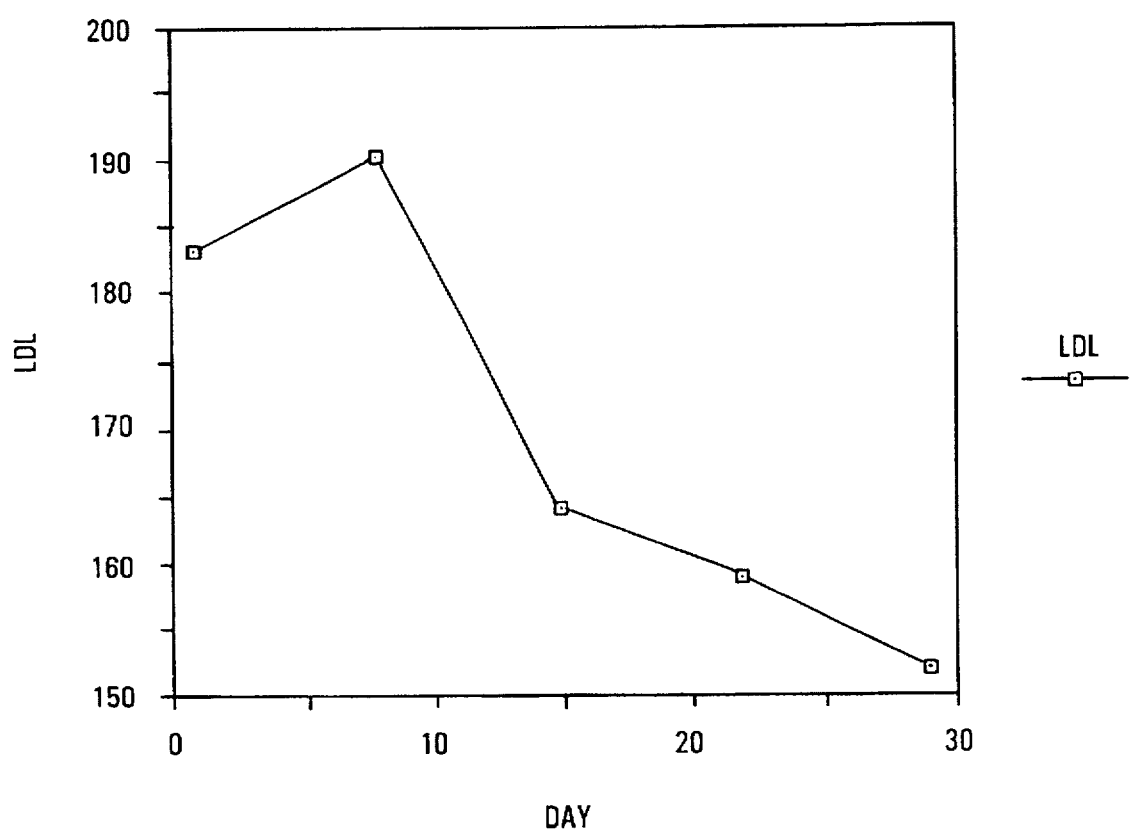
Figure 2D:
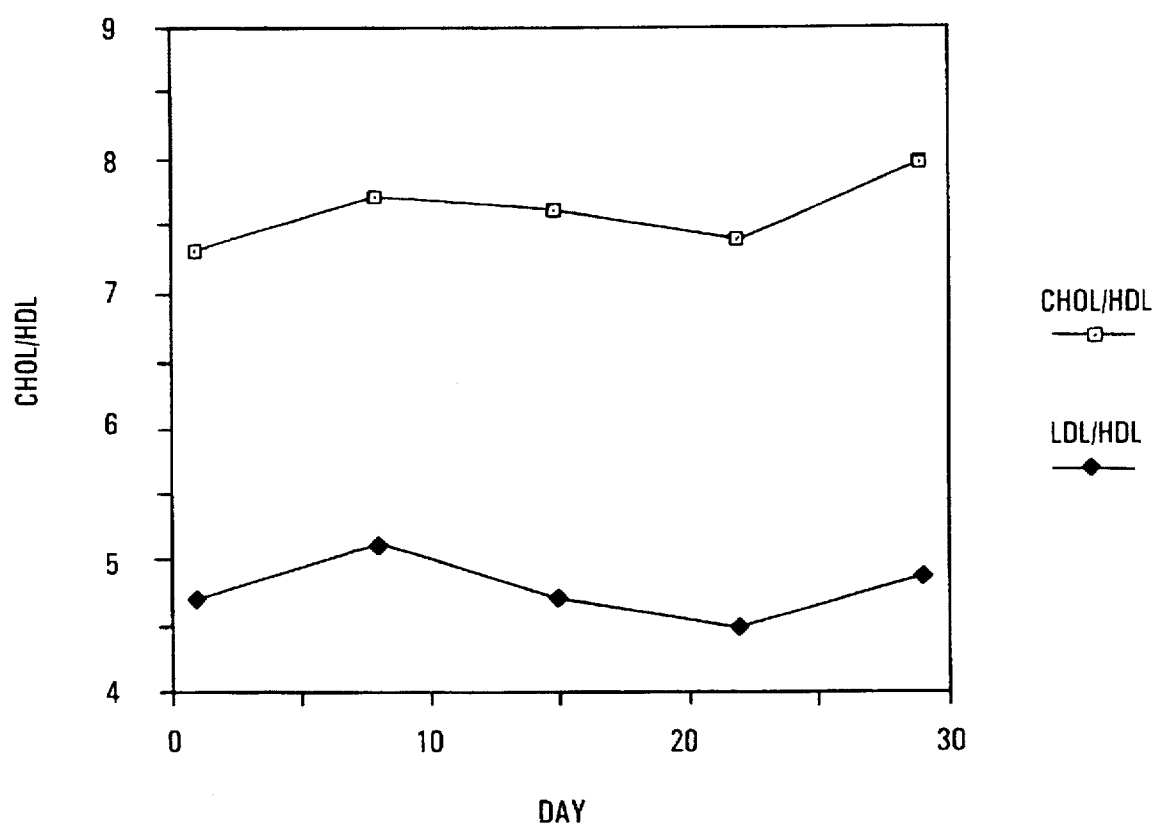
Figure 3A:
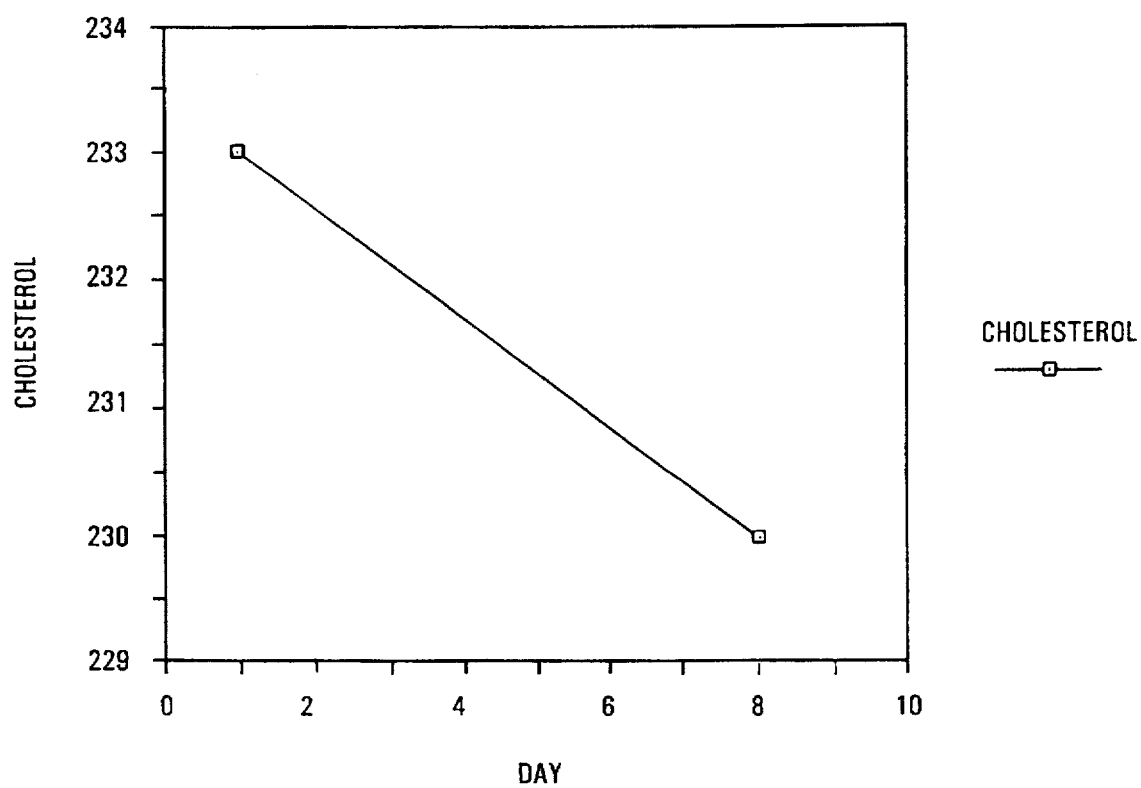
Figure 3B:
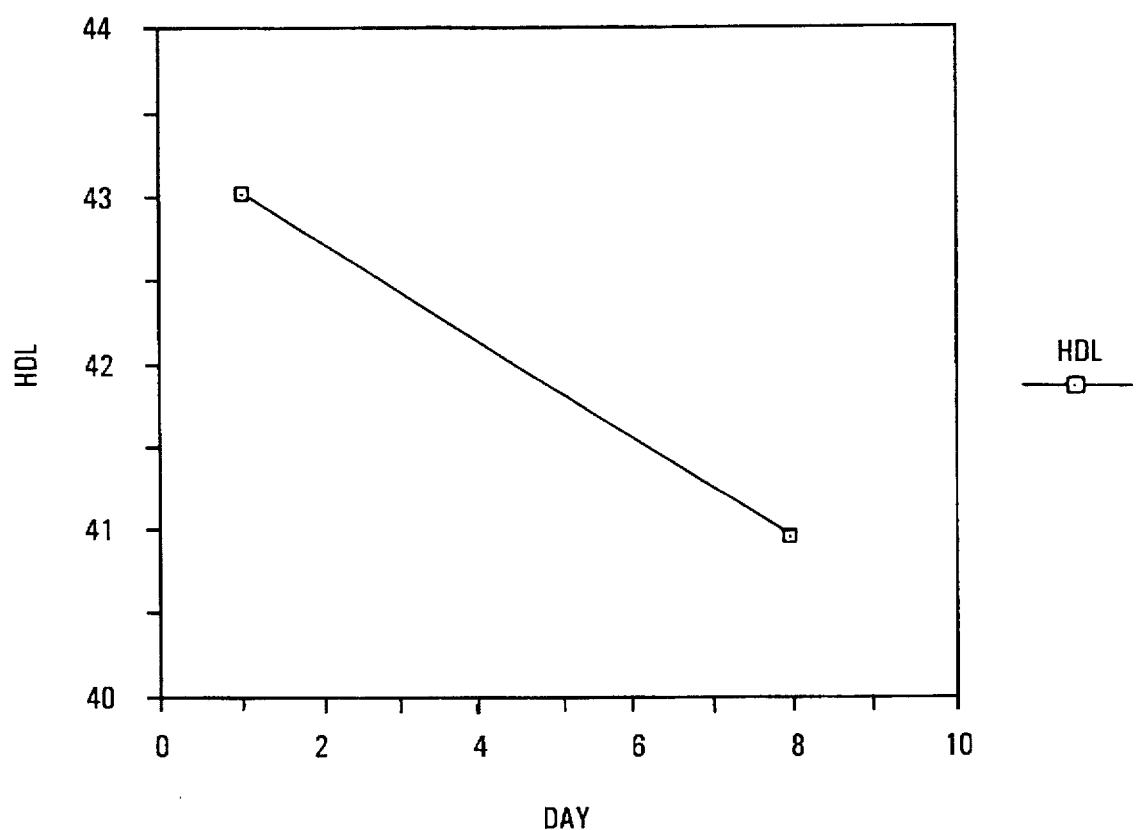
Figure 3C:
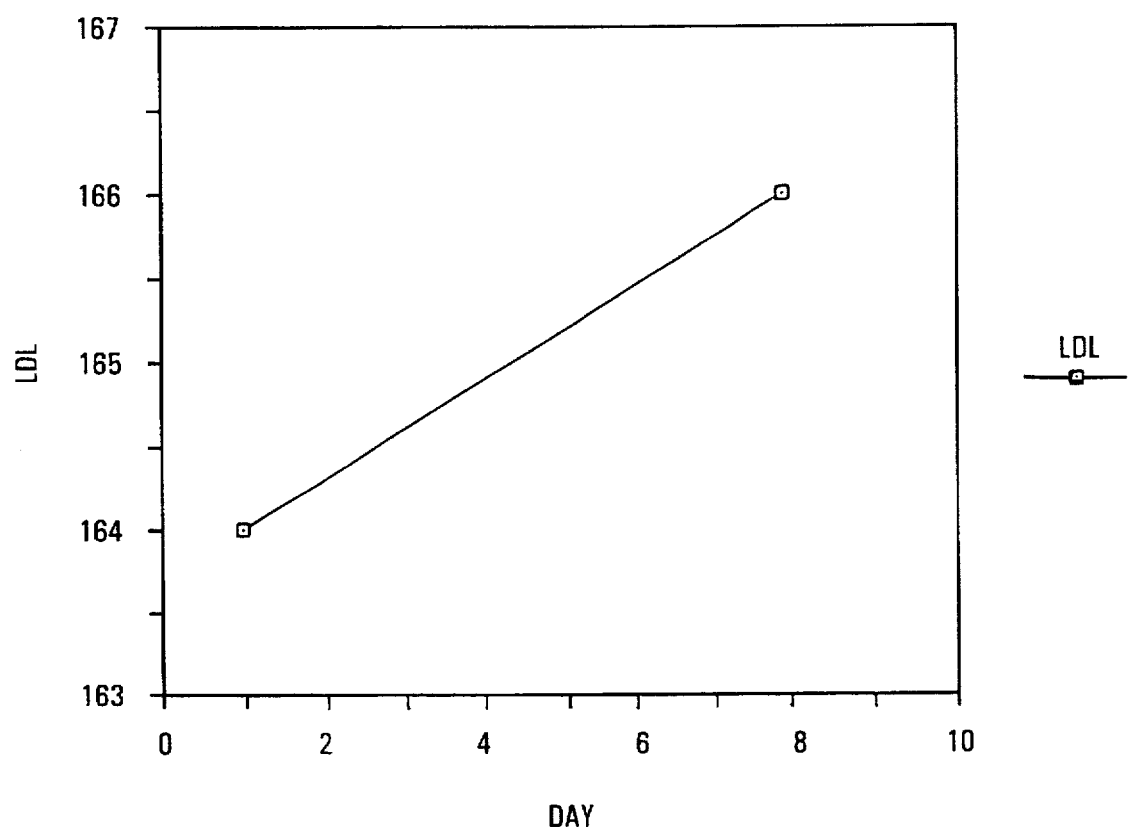
Figure 3D:
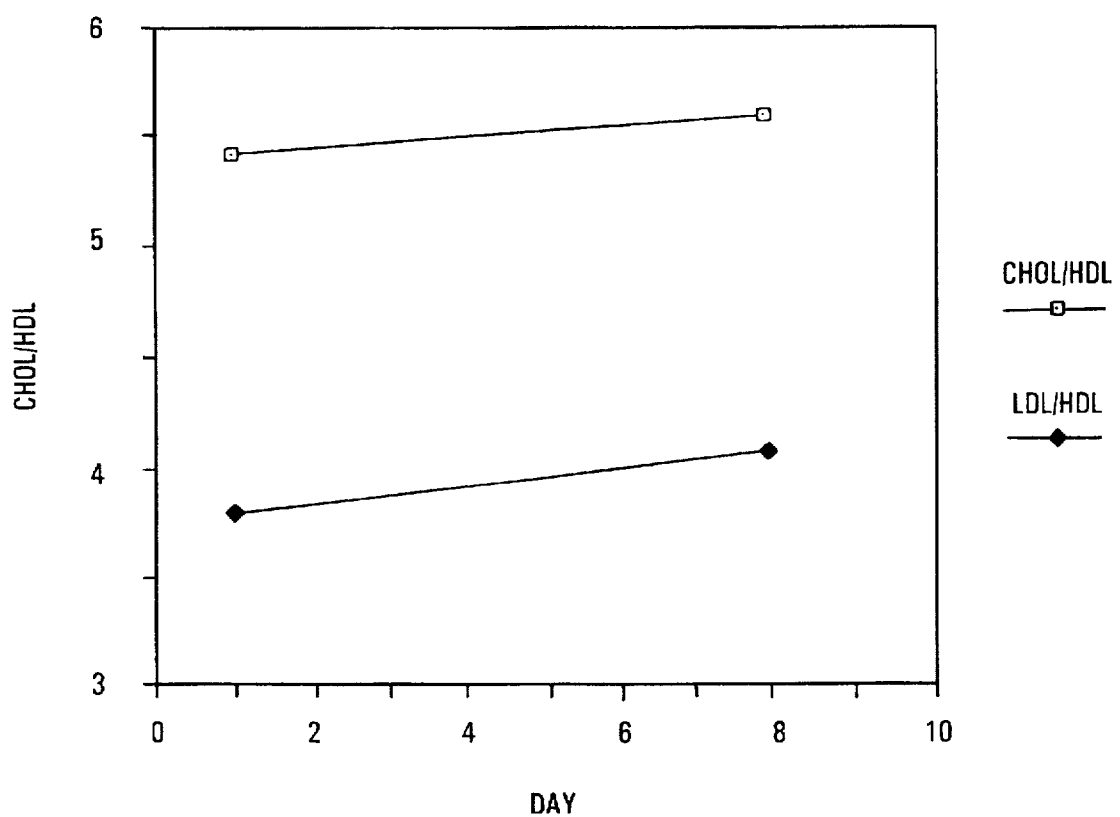
Figure 4A:
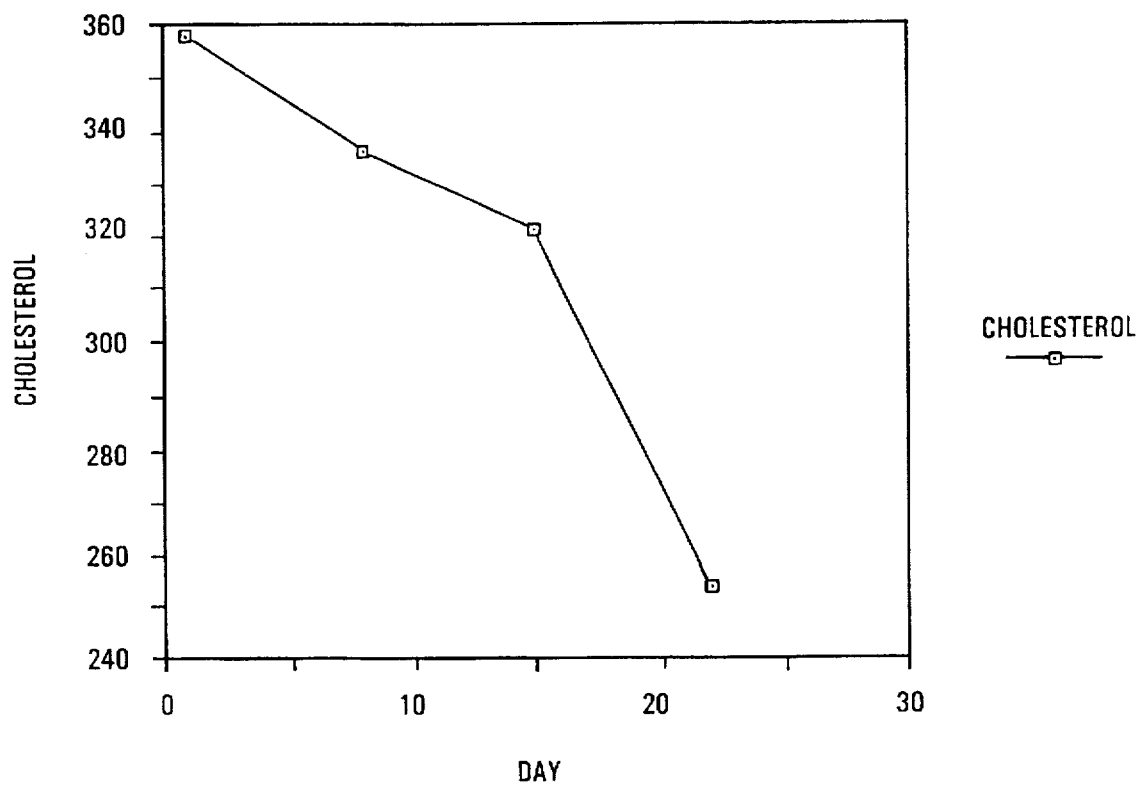
Figure 4B:
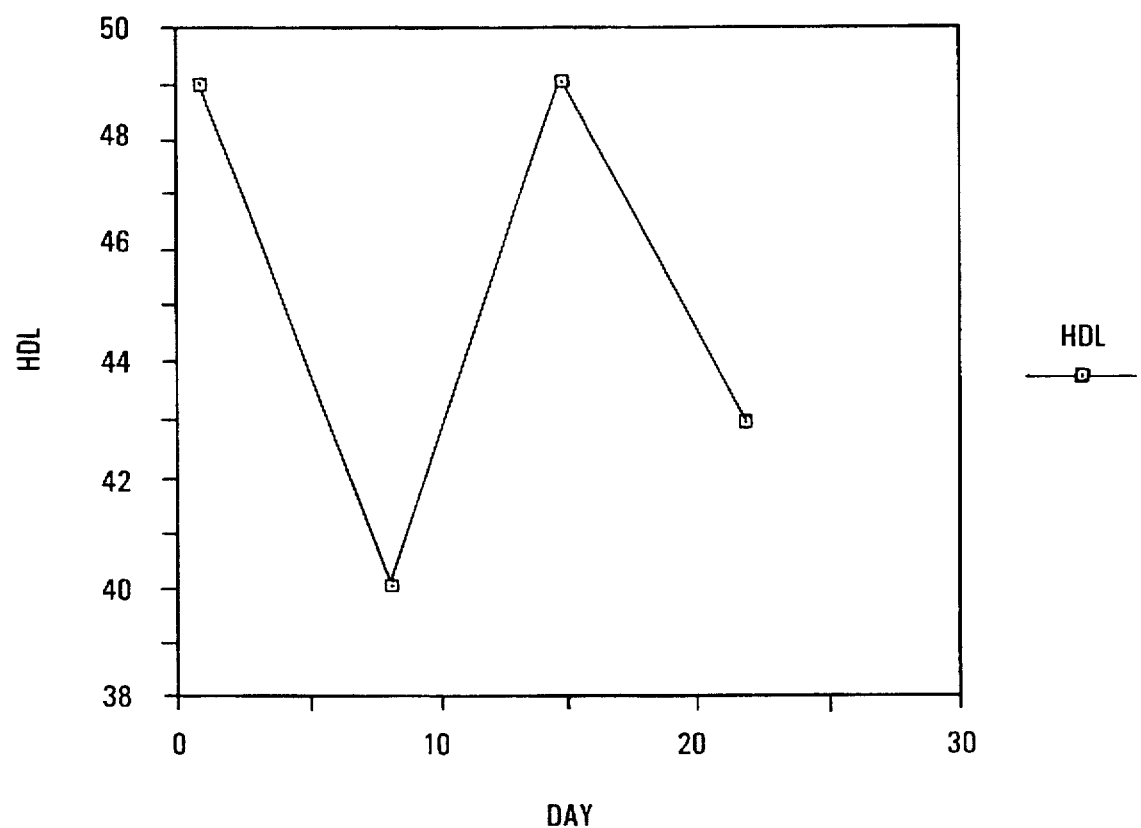
Figure 4C:
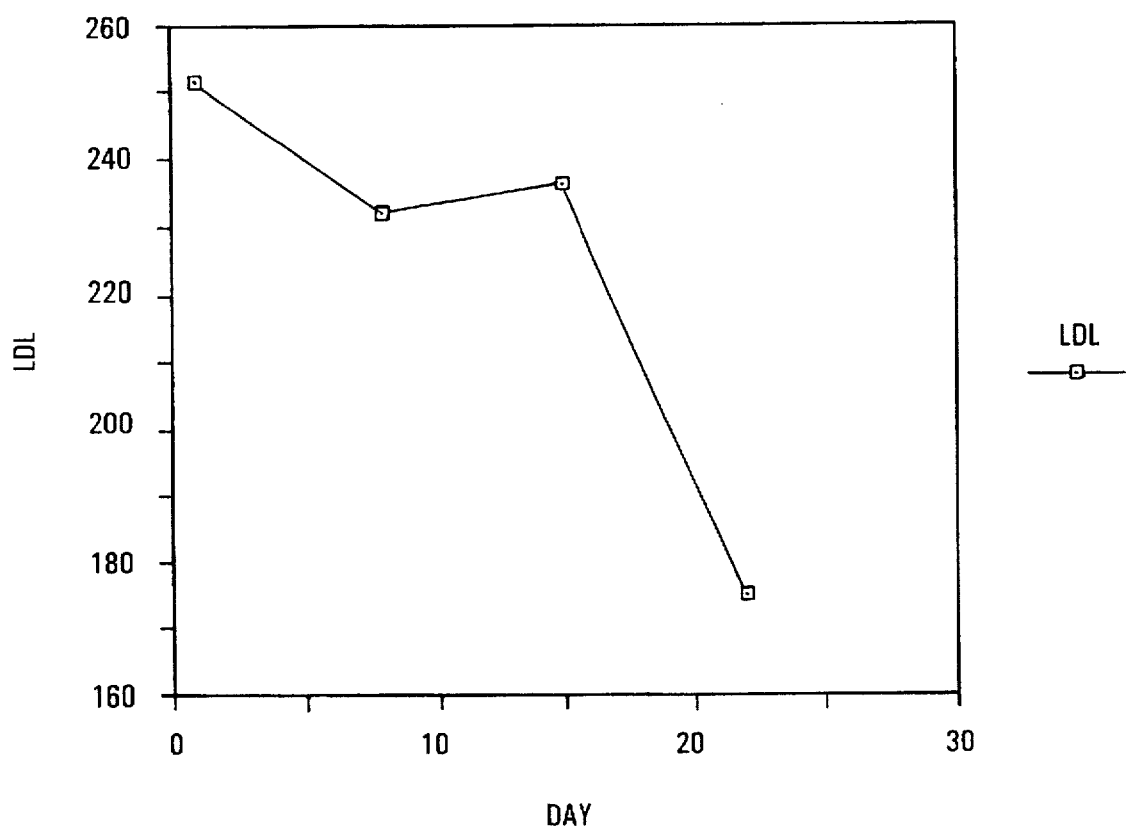
Figure 4D:
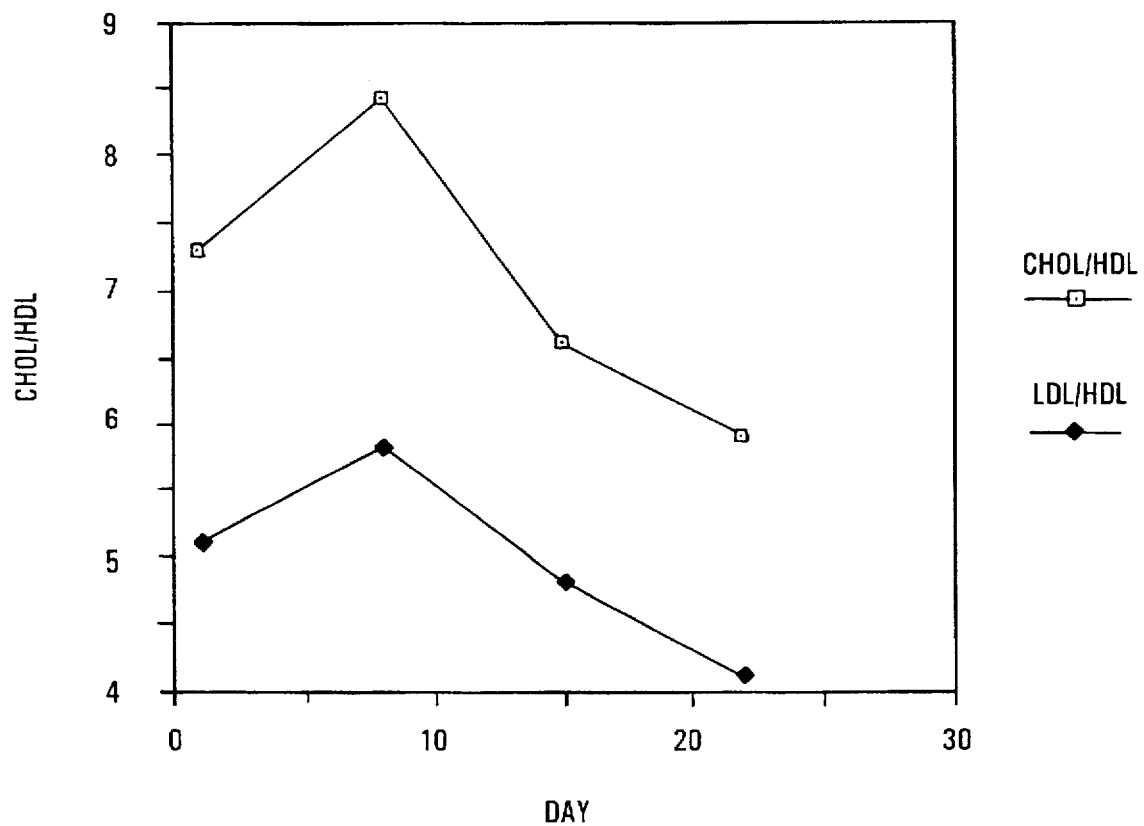
Figure 5A:
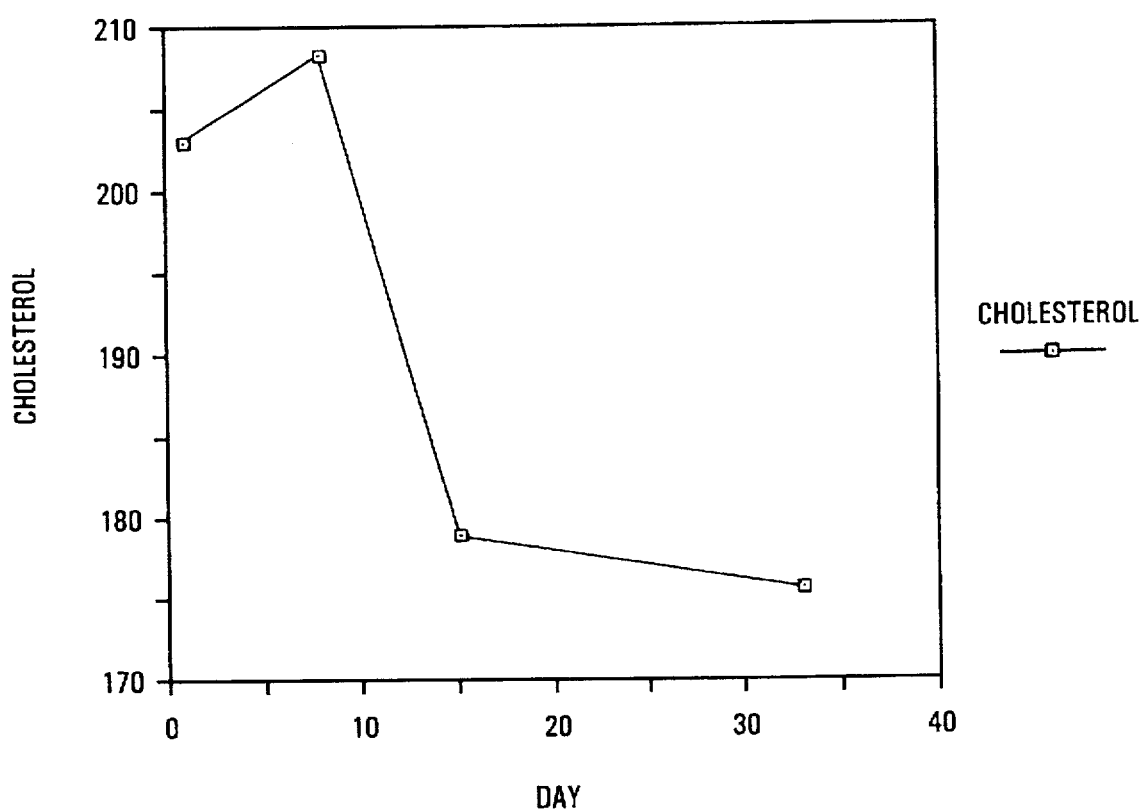
Figure 5B:
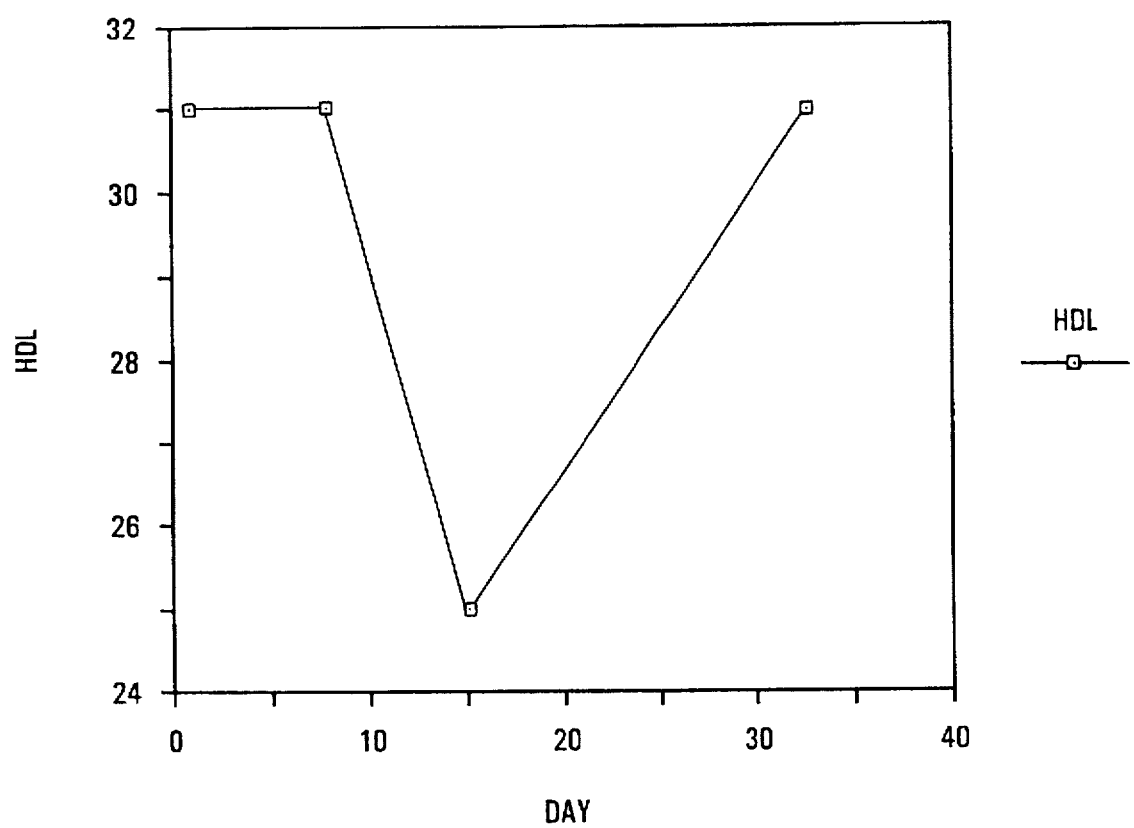
Figure 5C:
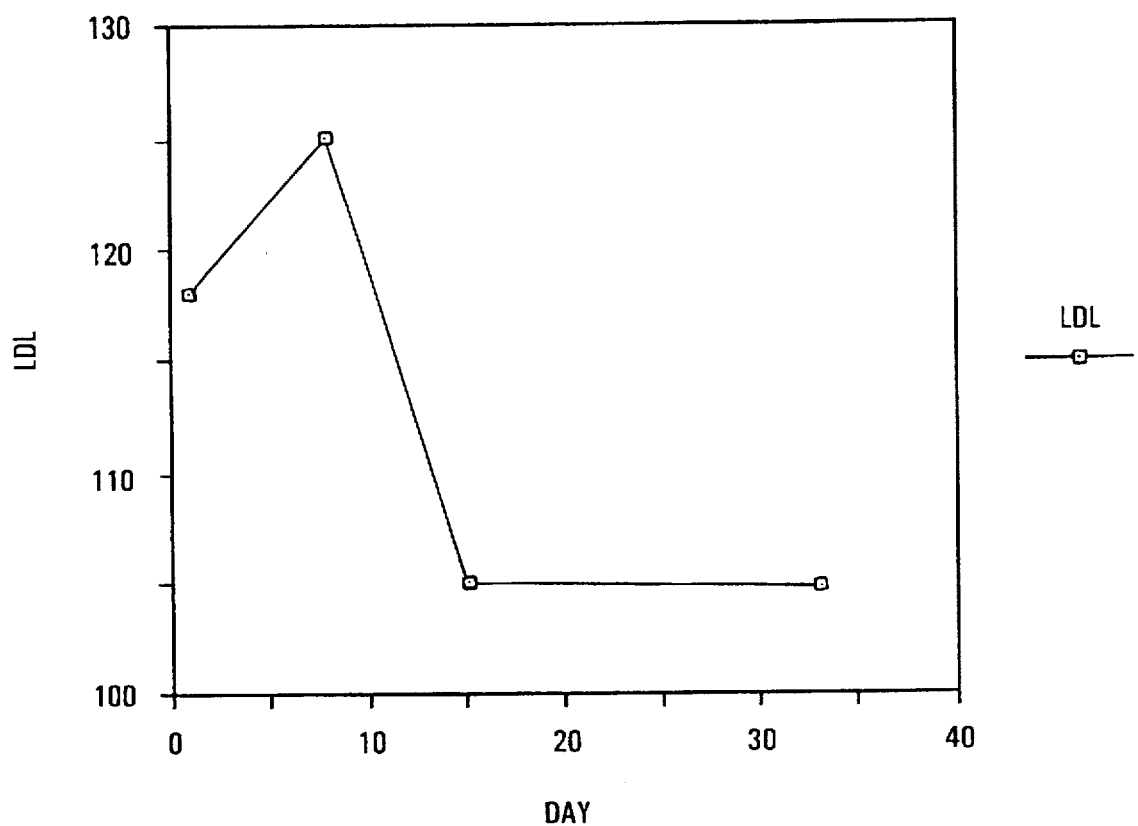
Figure 5D:
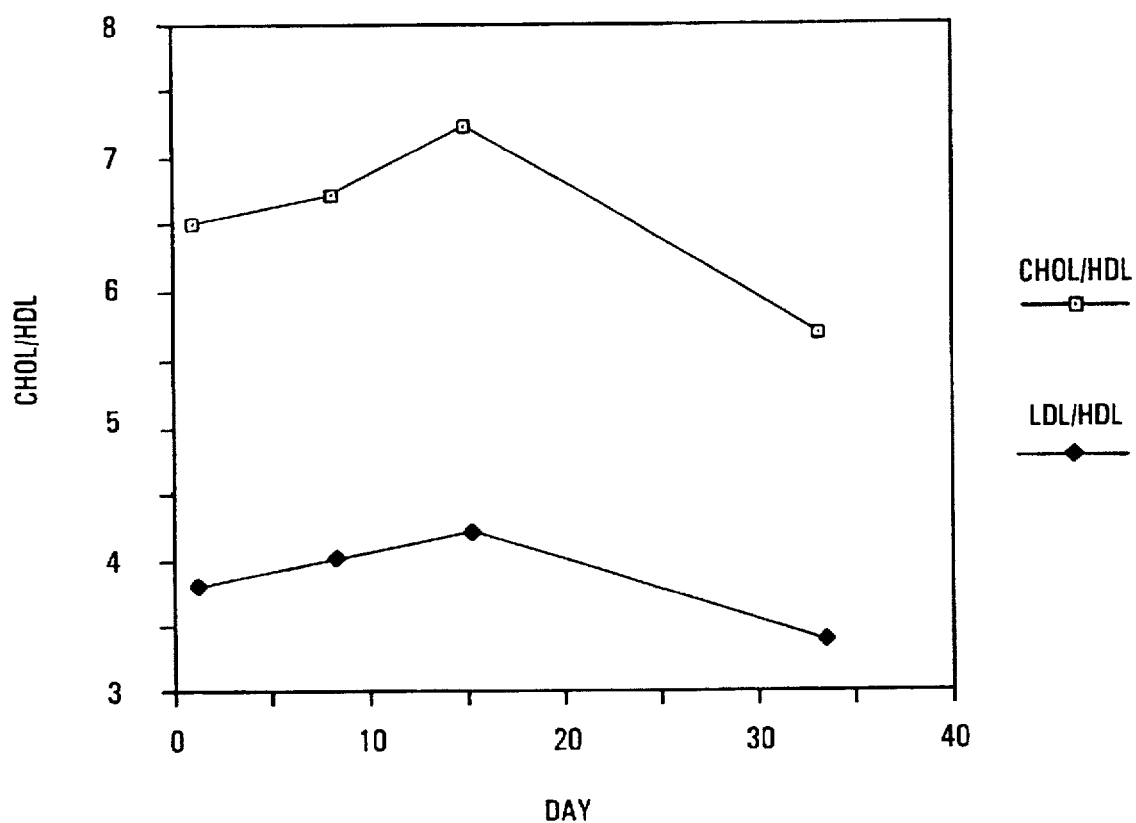
Figure 6A:
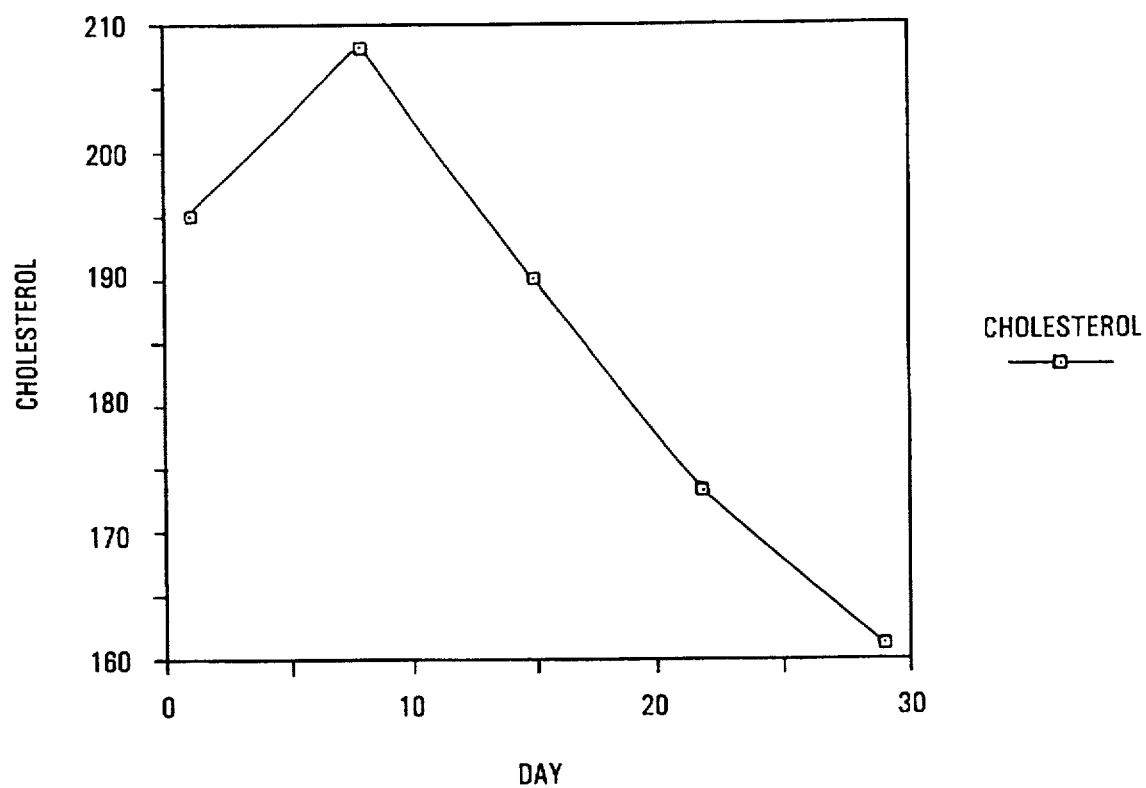
Figure 6B:
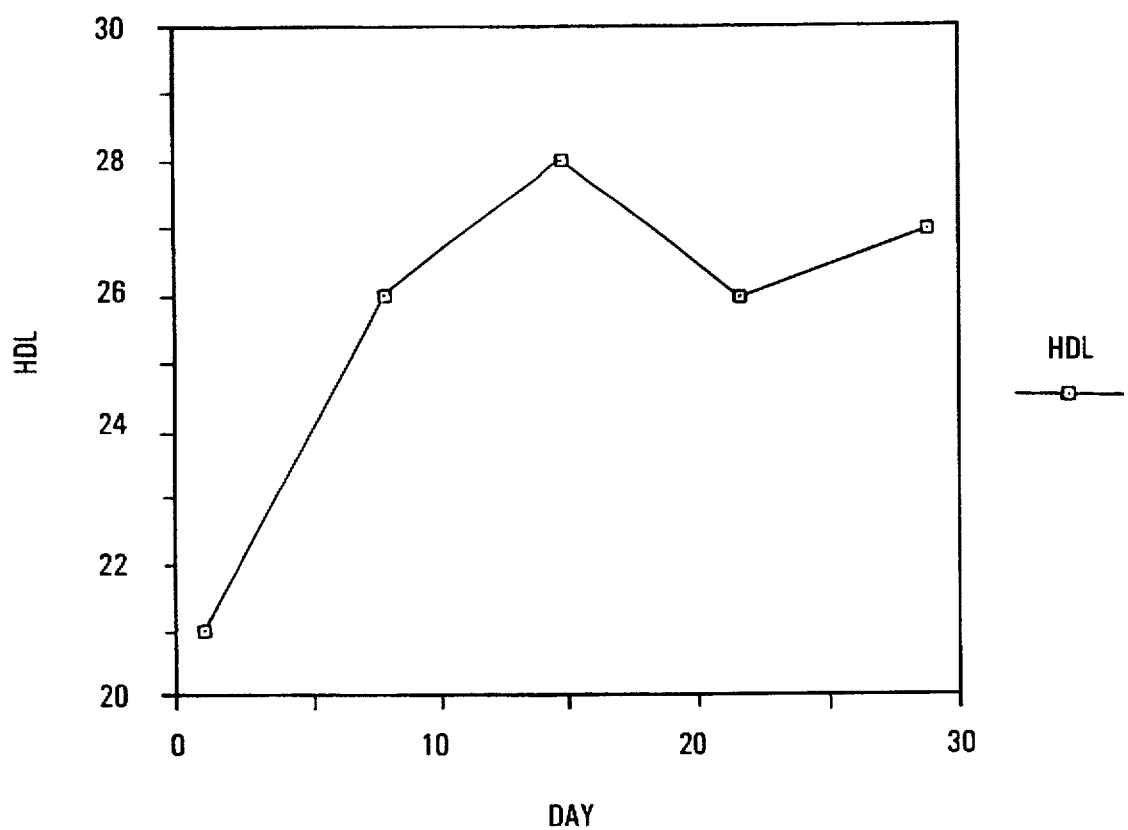
Figure 6C:
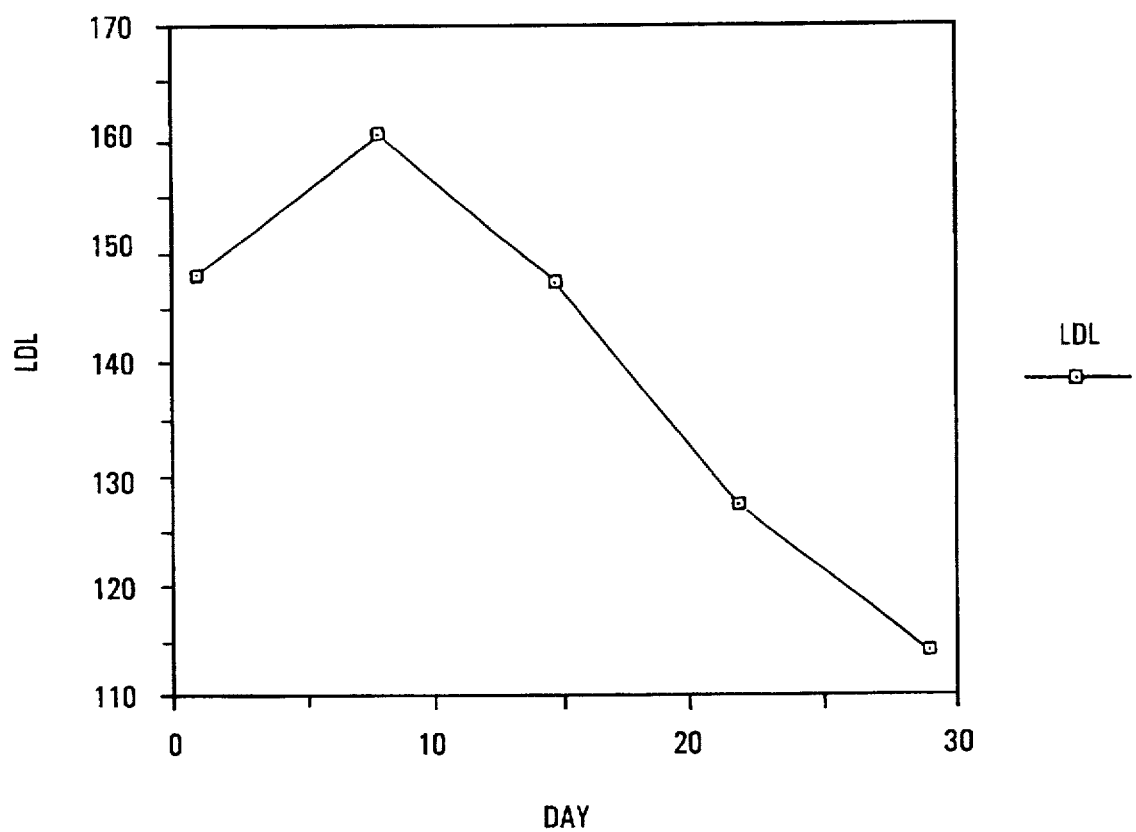
Figure 6D:
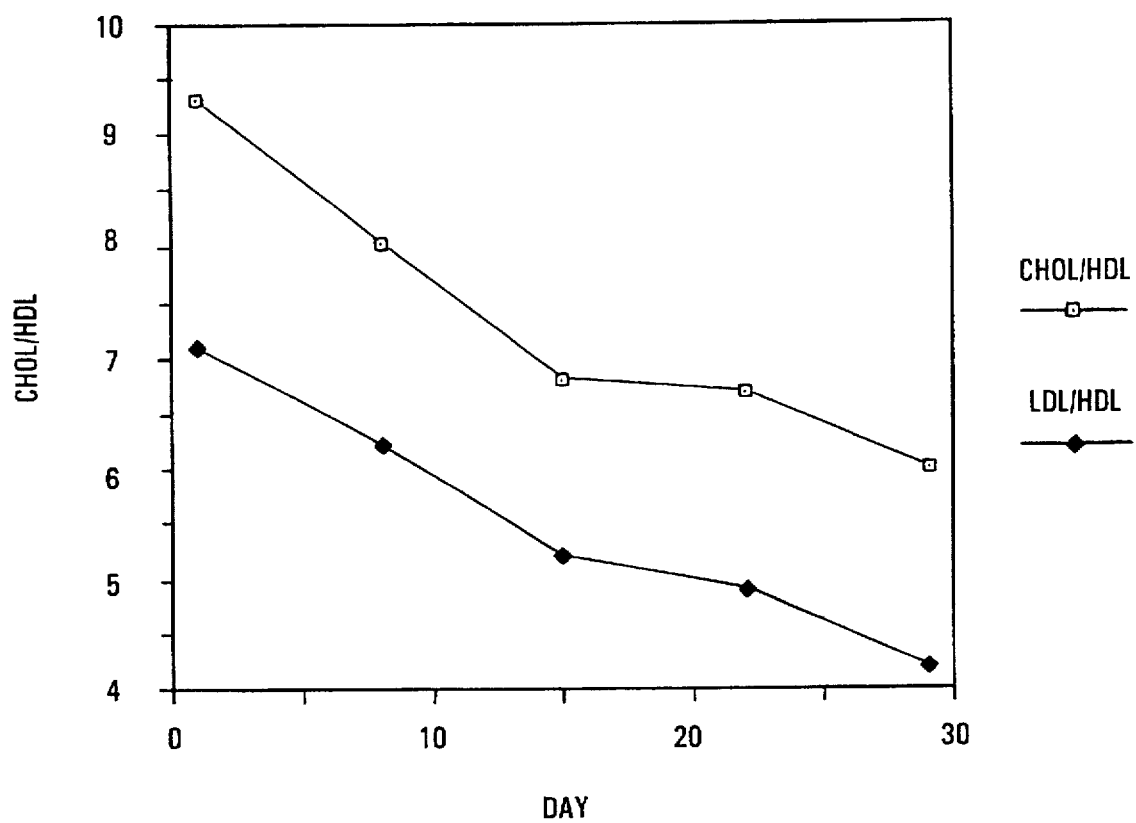
Figure 7A:
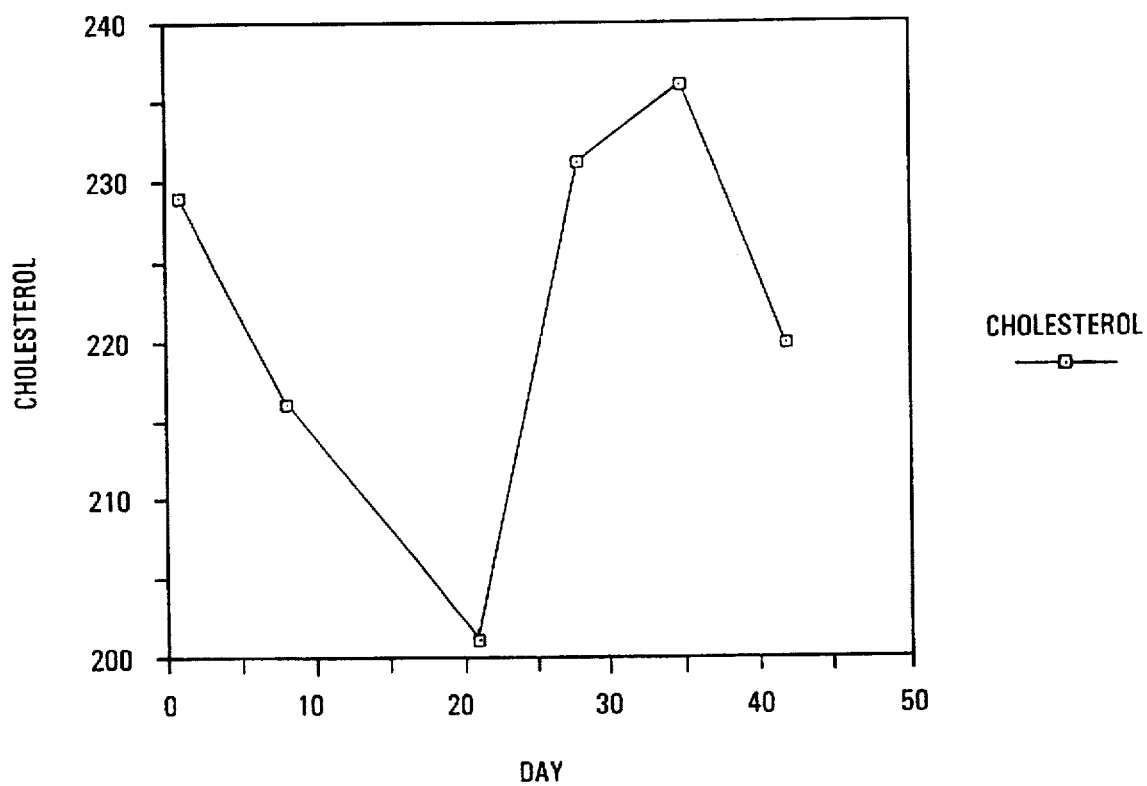
Figure 7B:
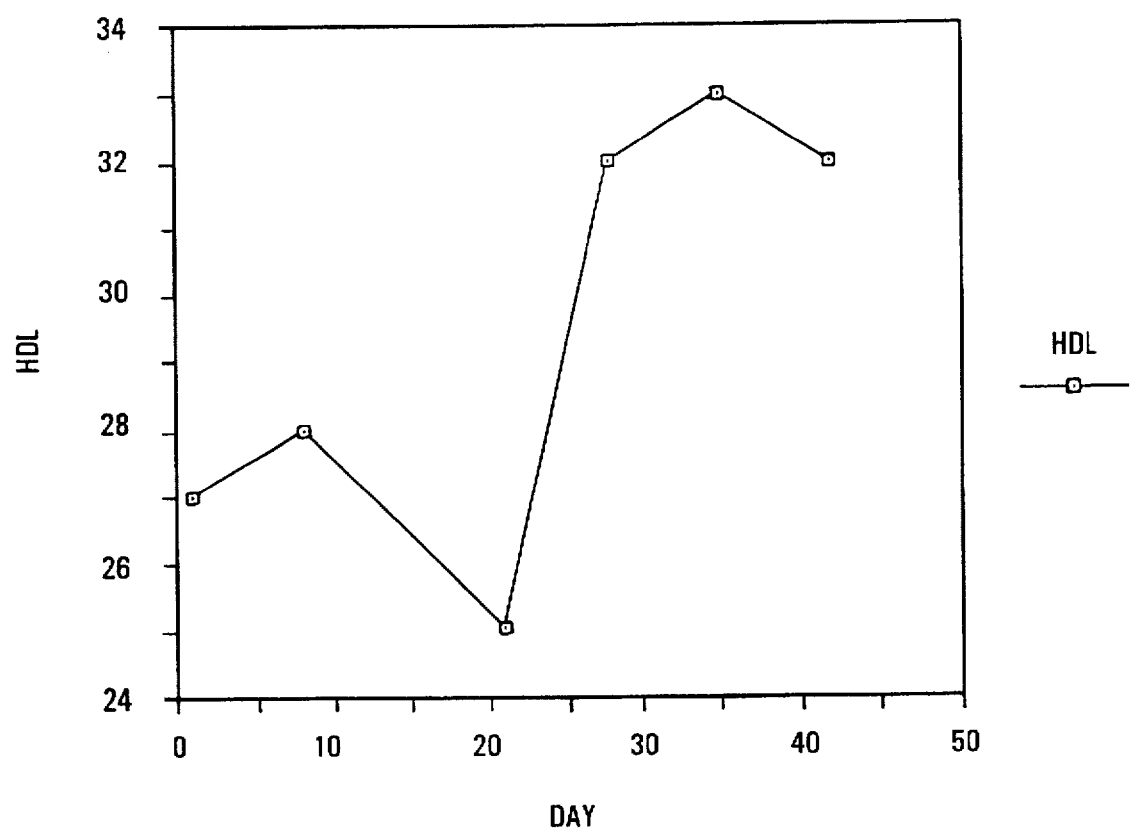
Figure 7C:
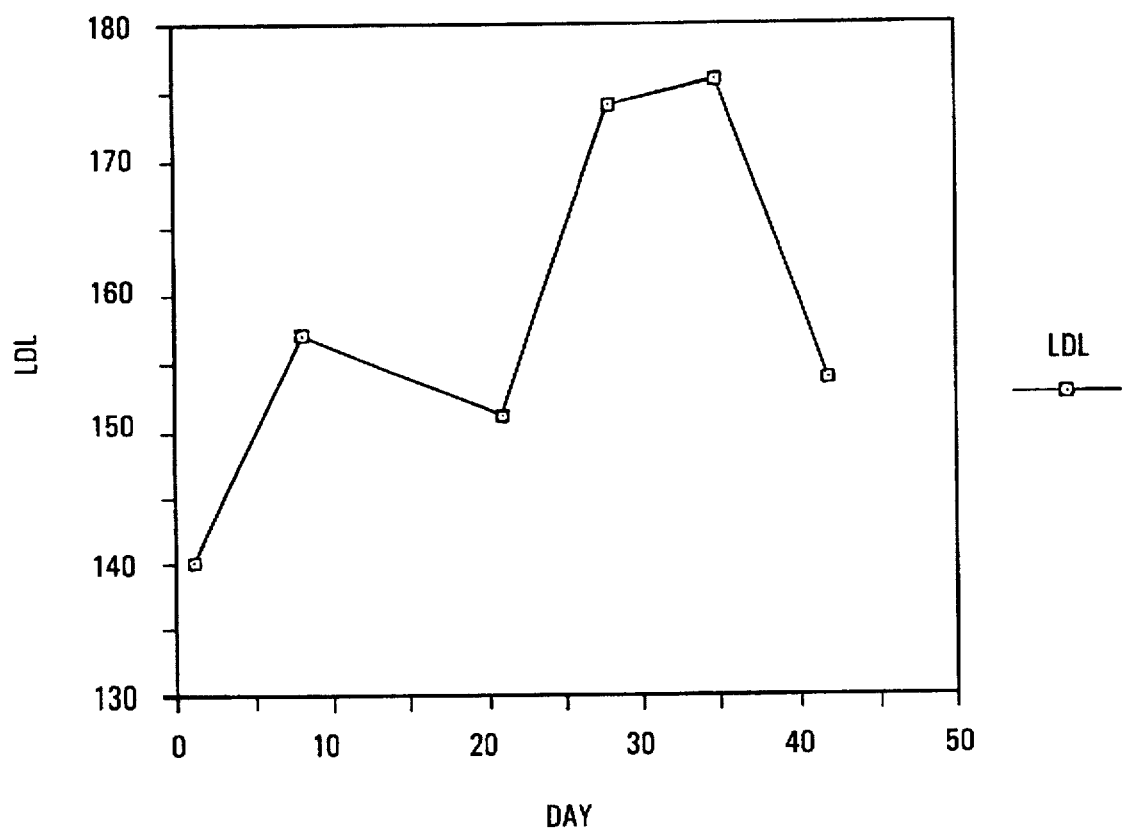
Figure 7D:
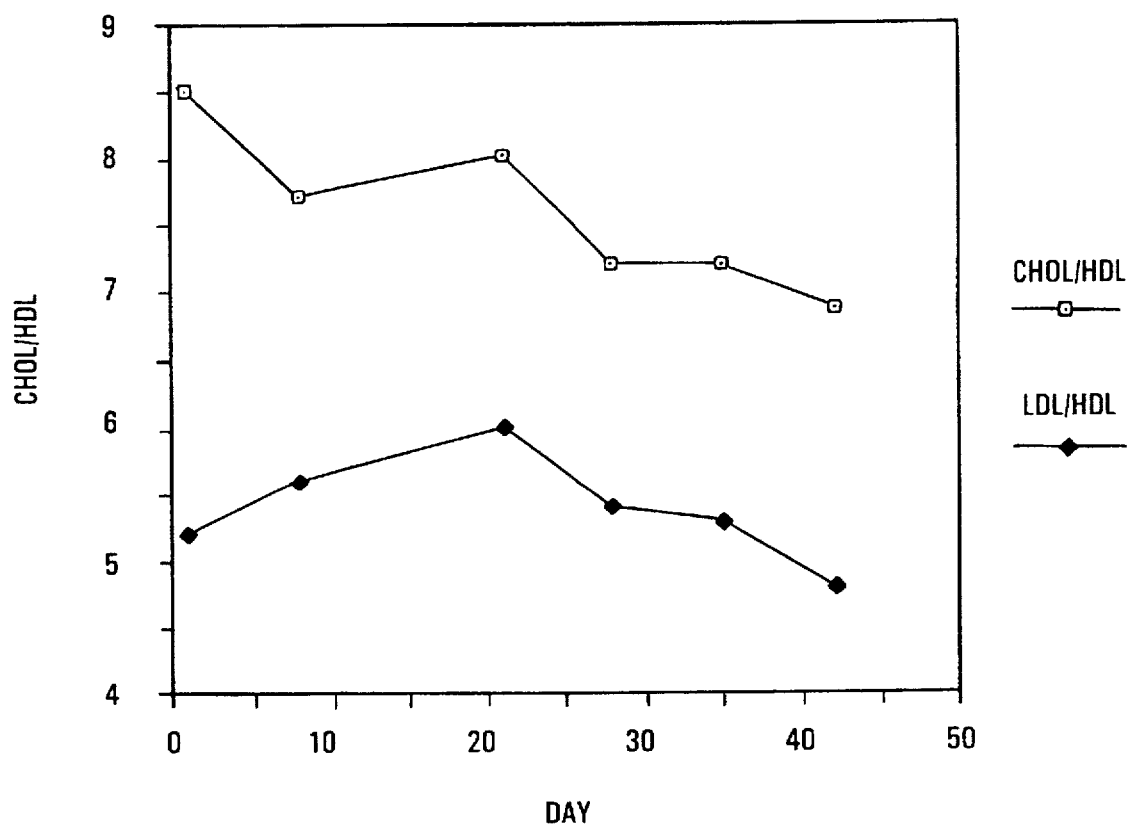
Figure 8A:
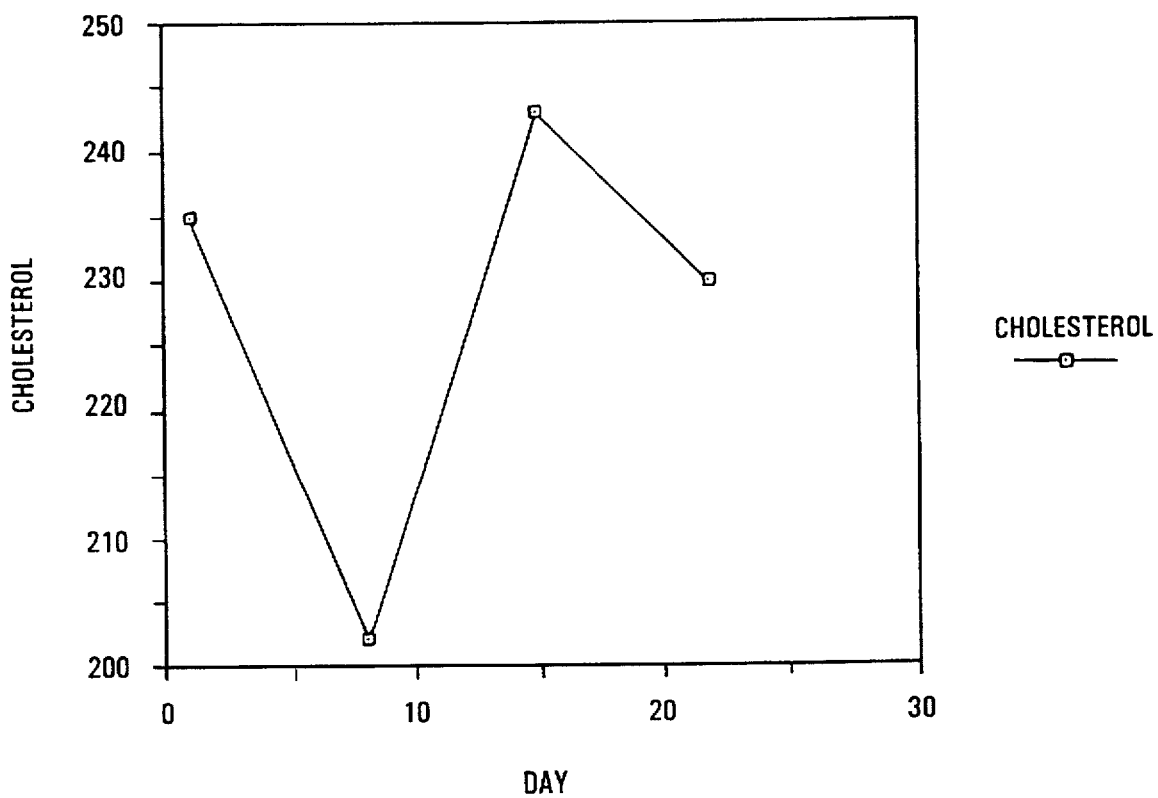
Figure 8B:
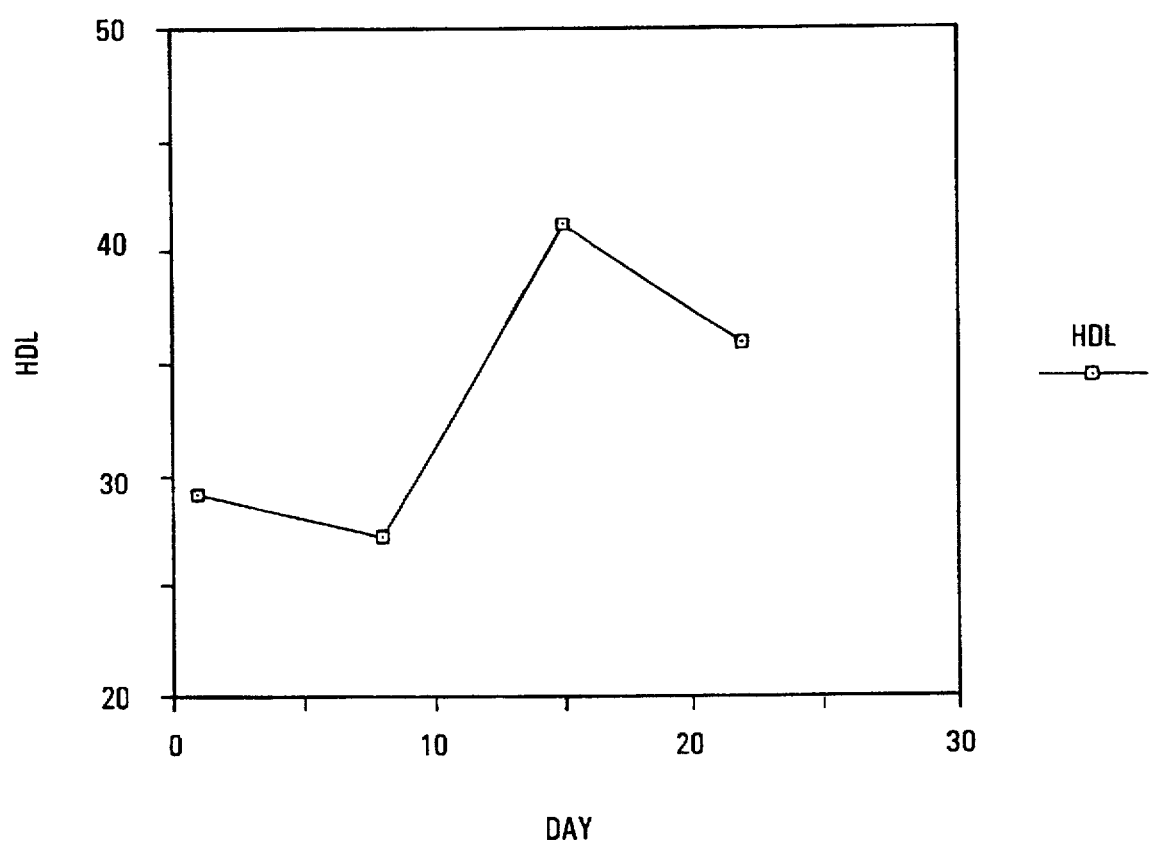
Figure 8C:
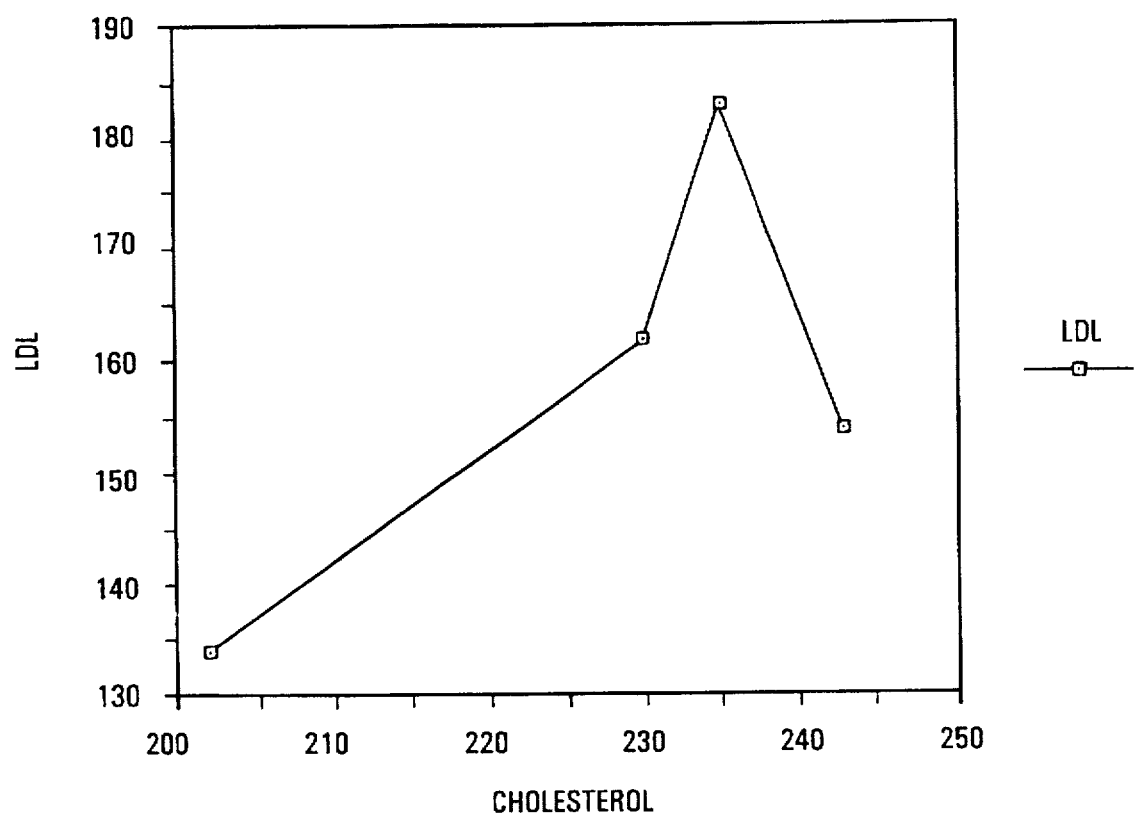
Figure 8D:
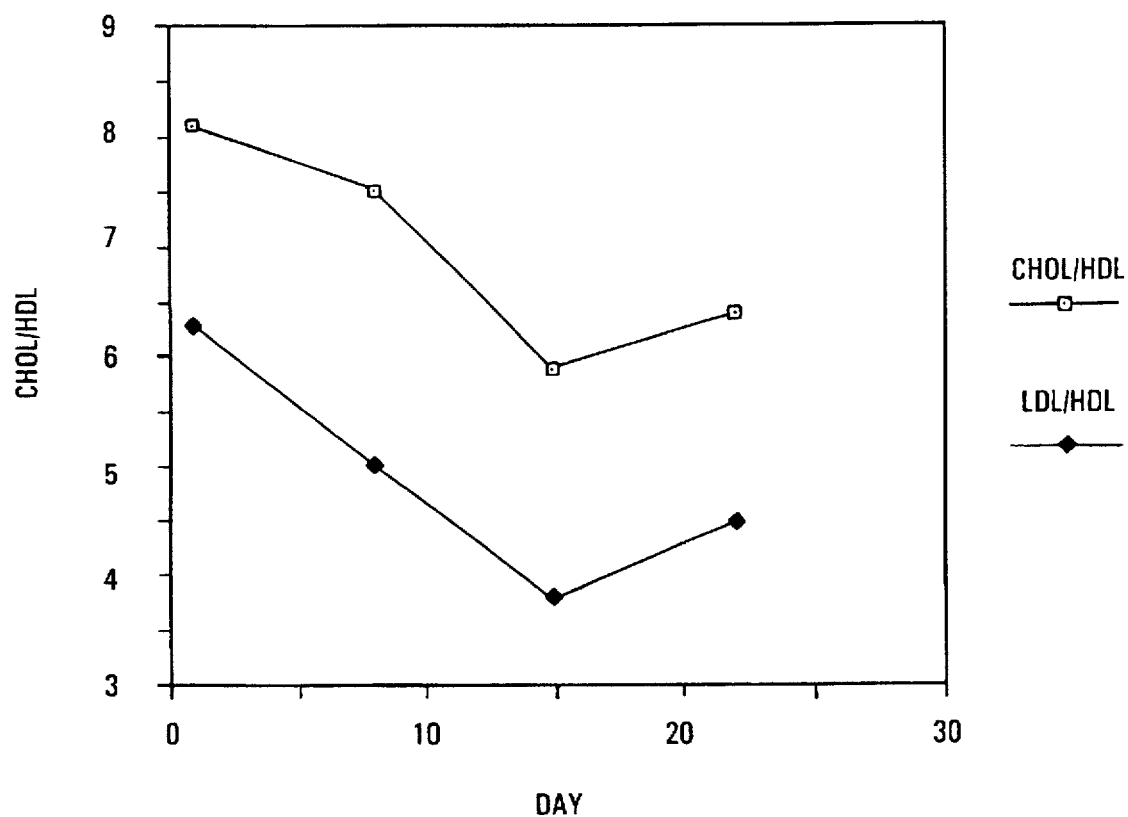
Figure 9A:
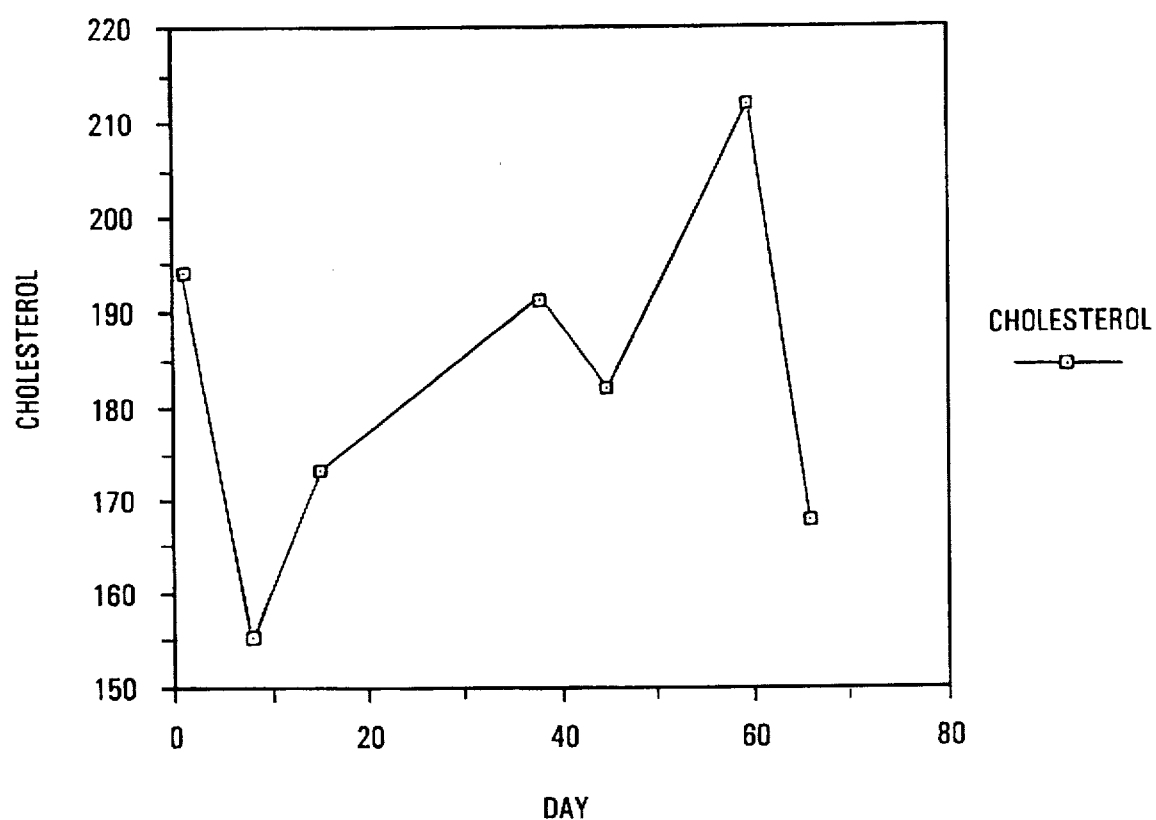
Figure 9B:
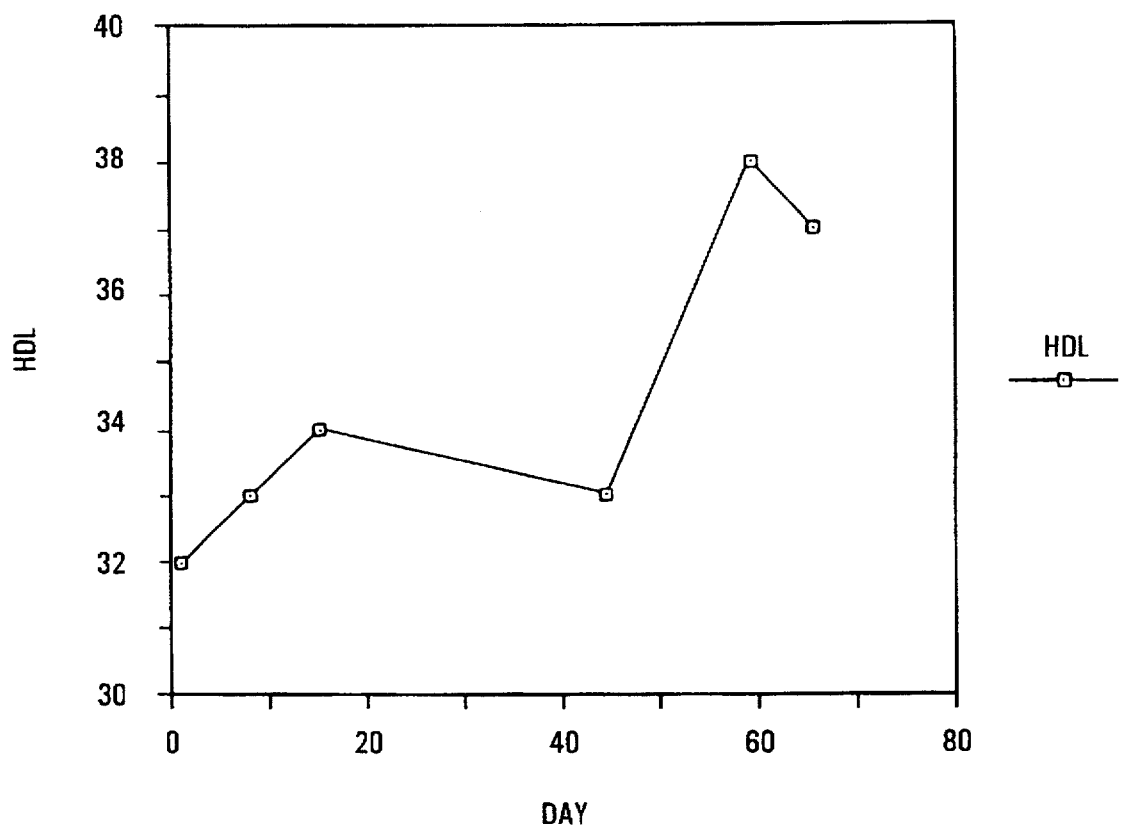
Figure 9C:
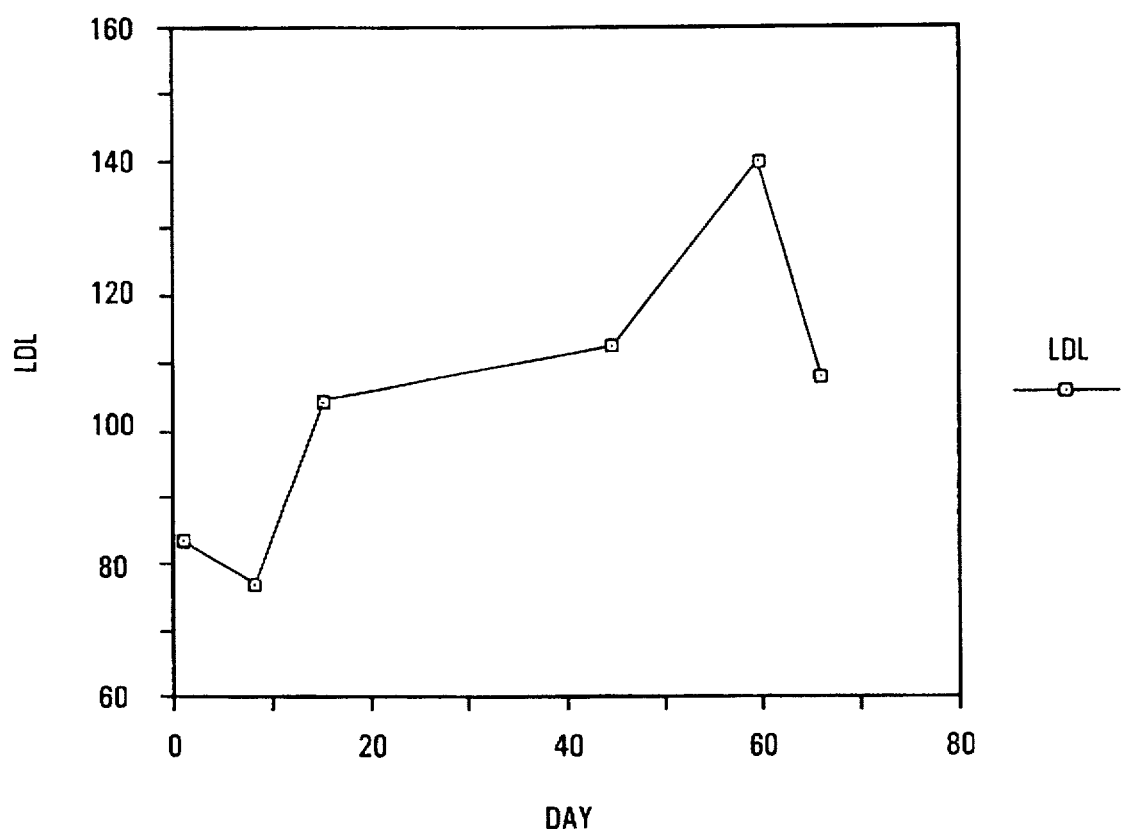
Figure 9D:
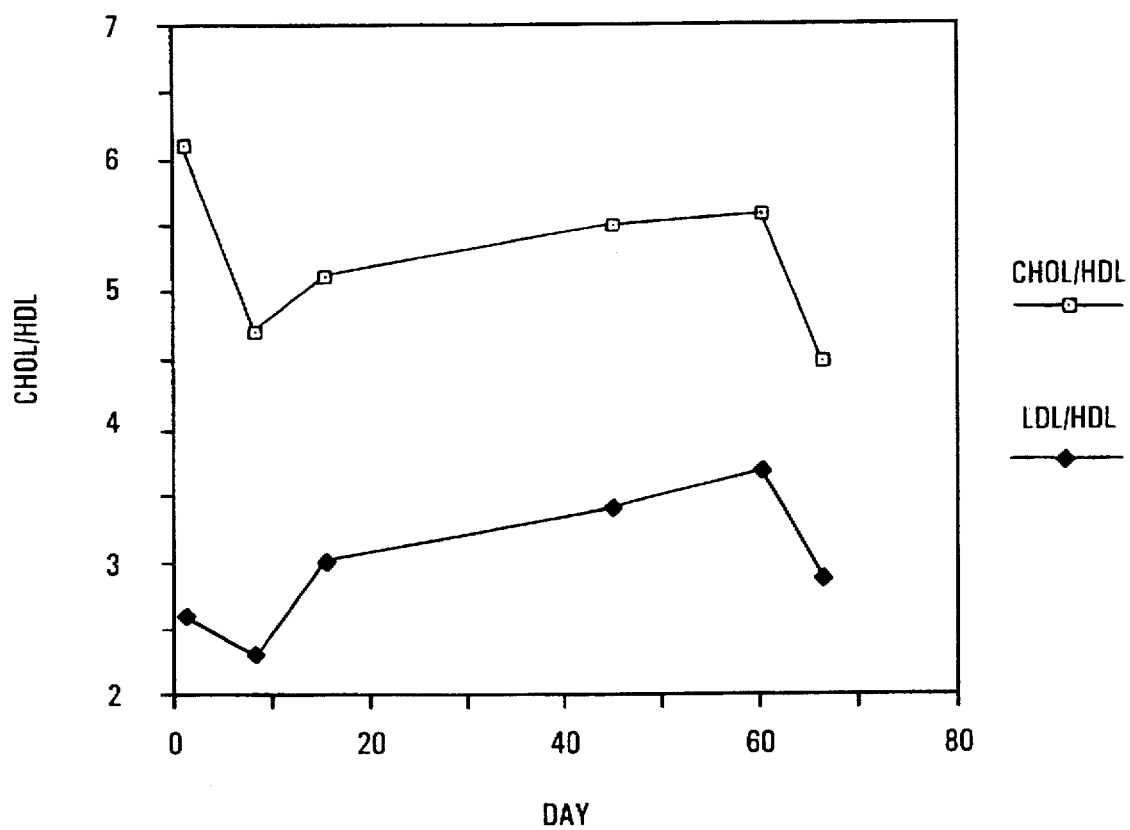
Figure 10A:
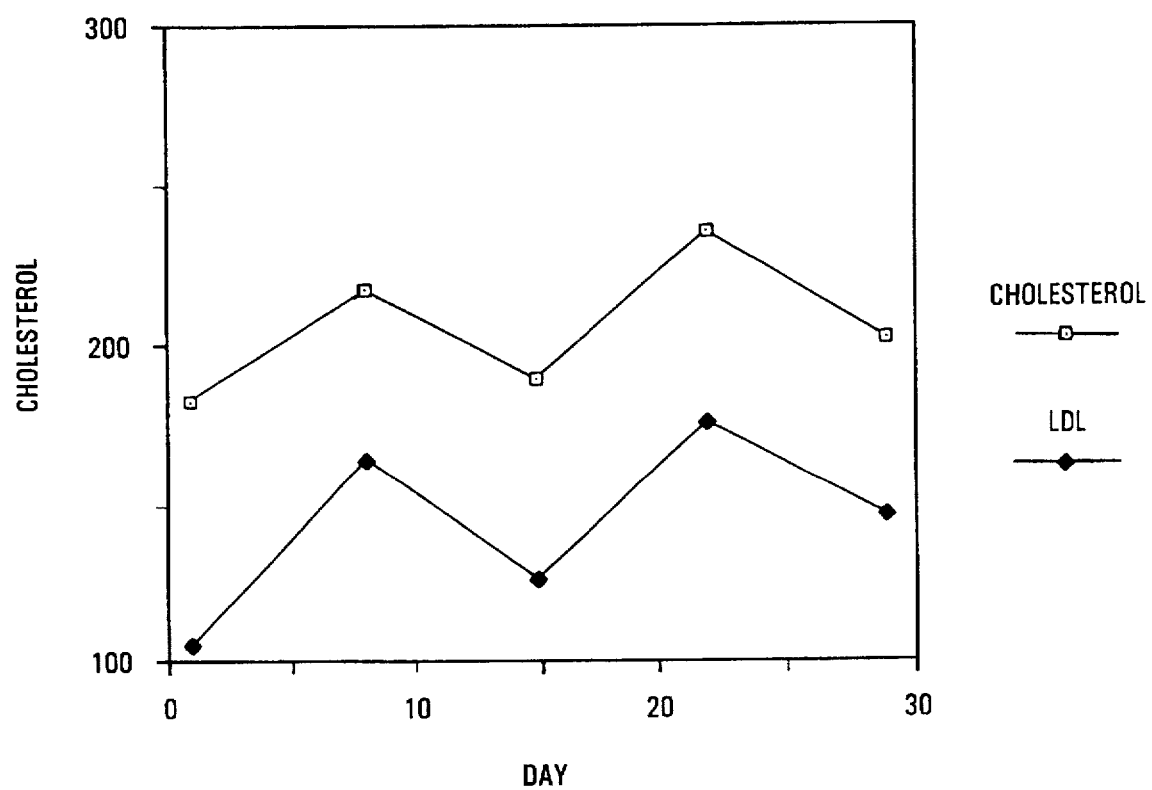
FIG. 10 Panels A–C detail plasma cholesterol levels for Patient #10.
Figure 10B:
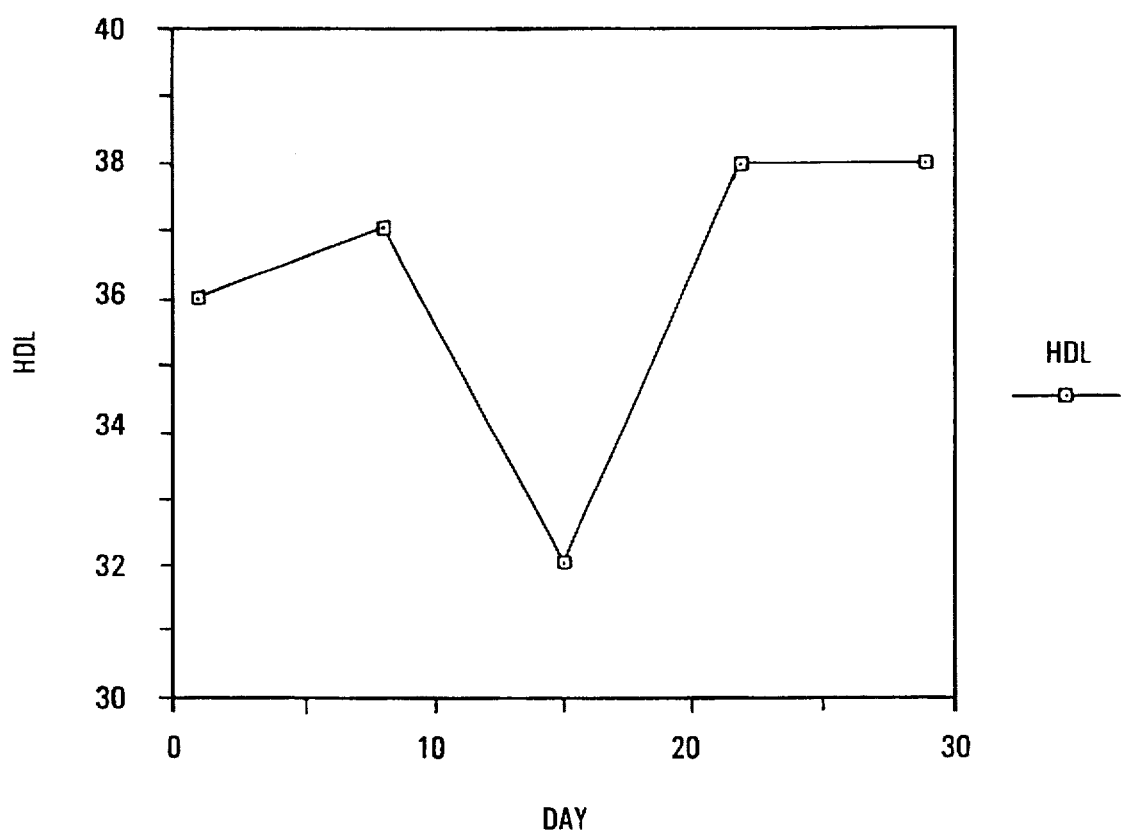
Figure 10C:
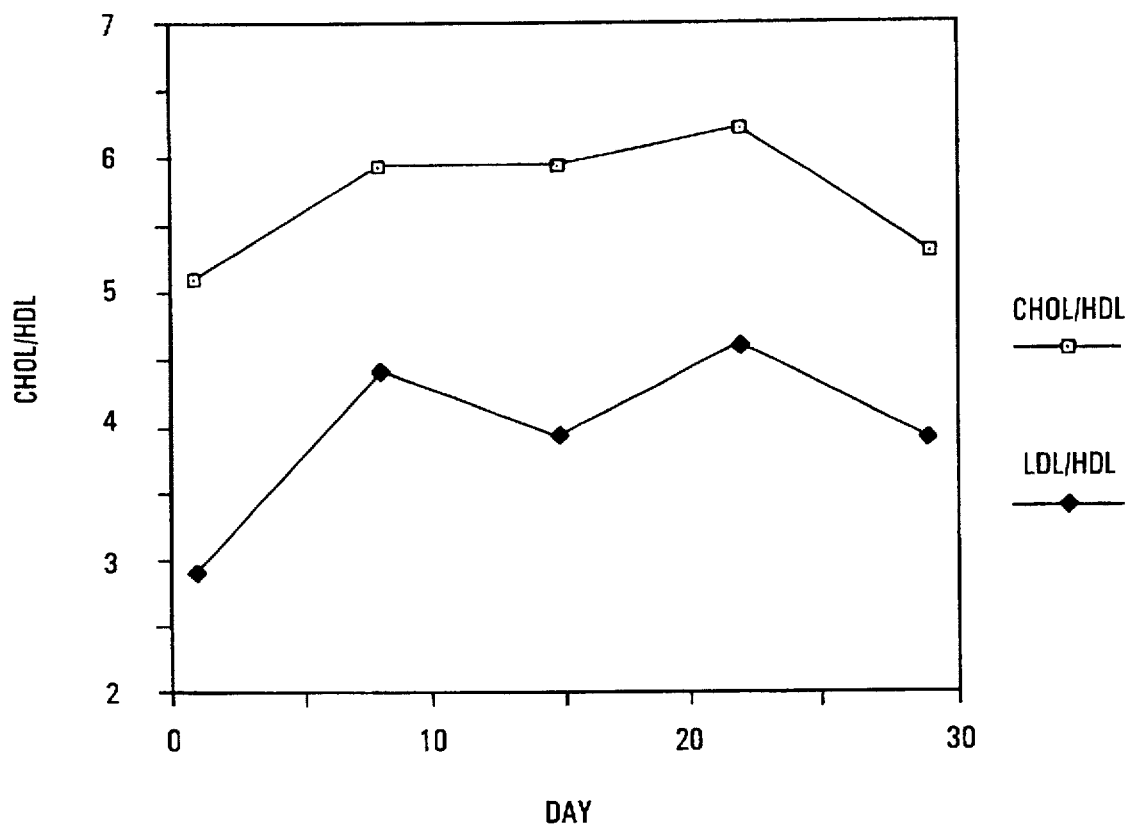
Figure 11A:
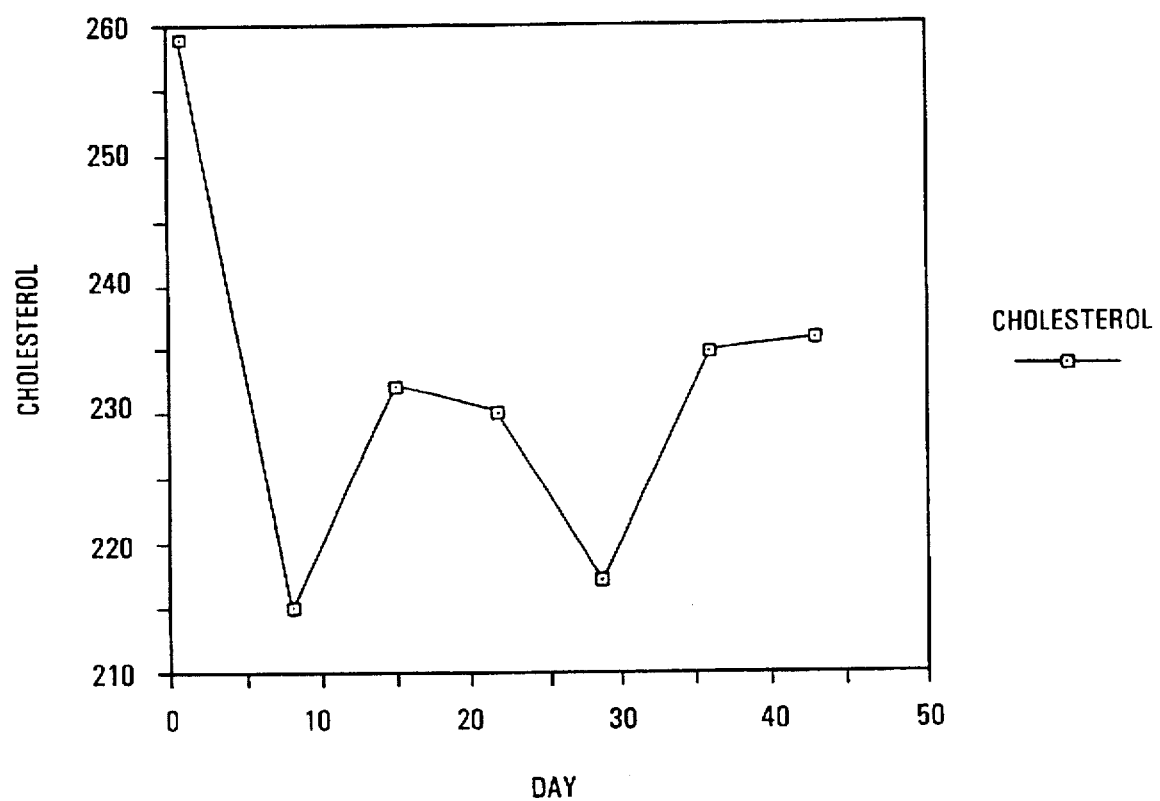
FIG. 11 Panels A–D detail plasma cholesterol levels for Patient #11.
Figure 11B:
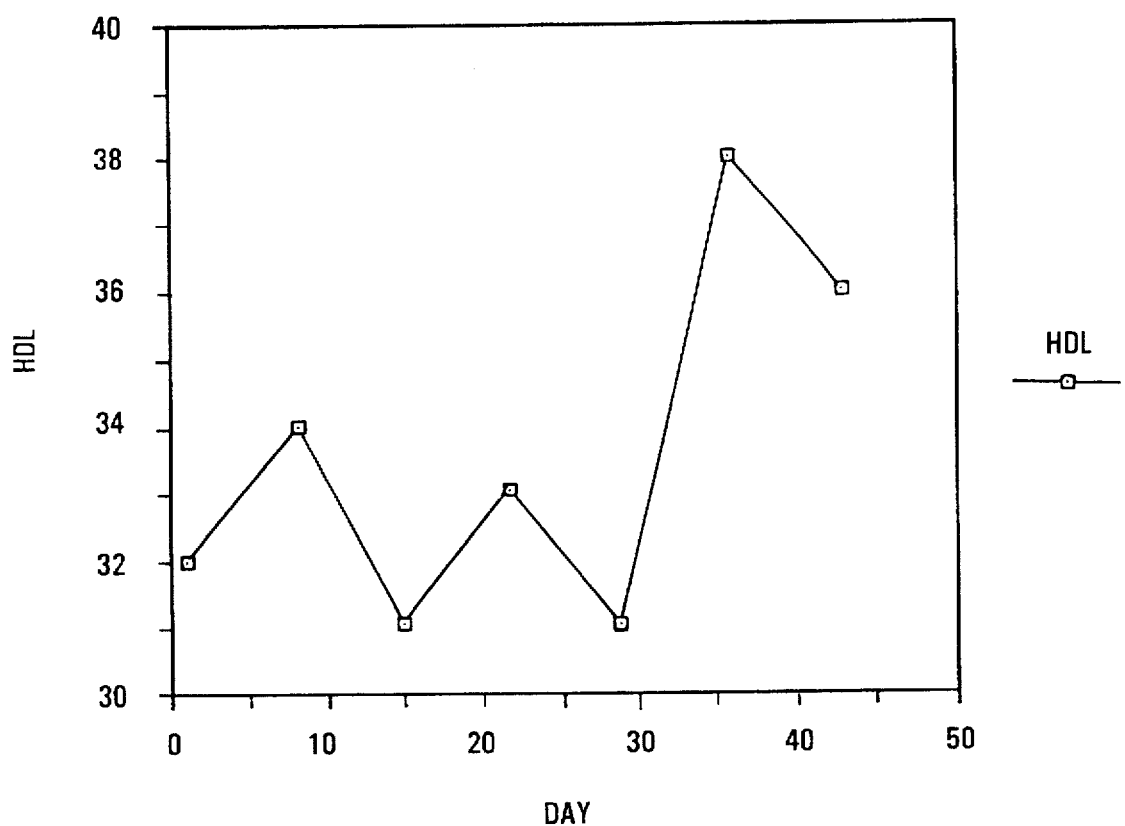
Figure 11C:
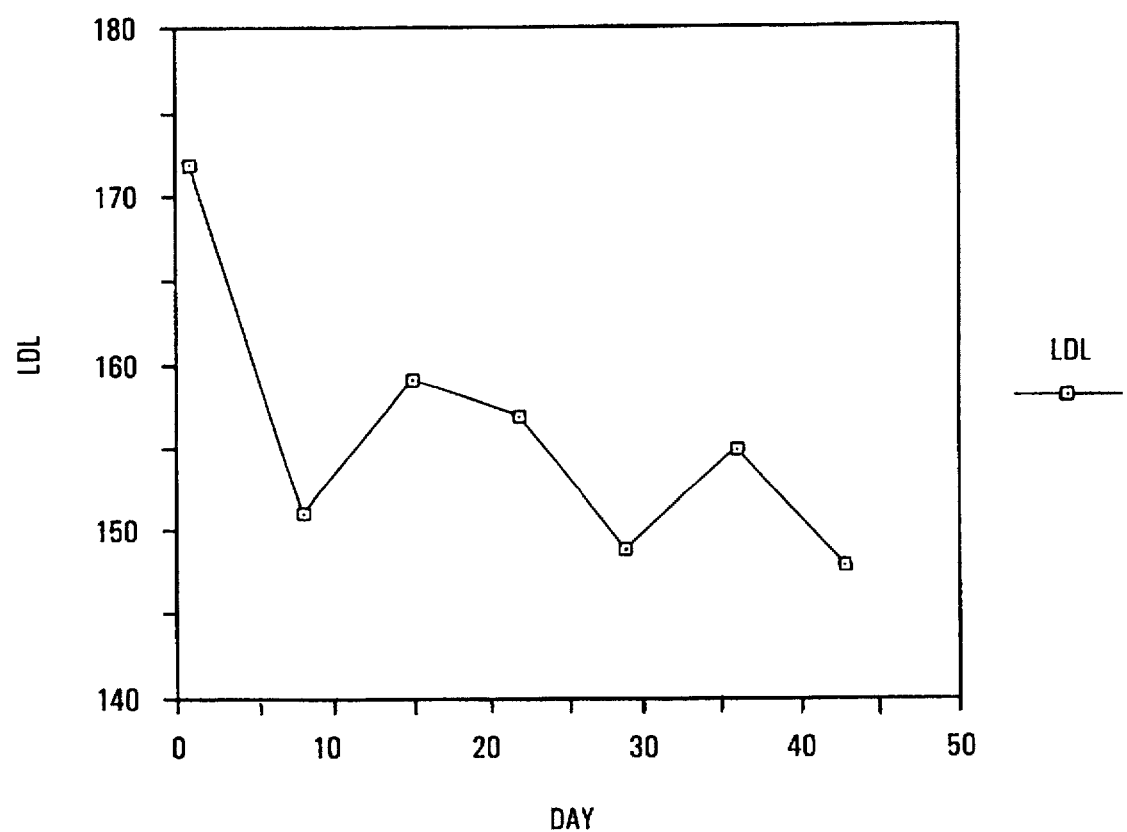
Figure 11D:
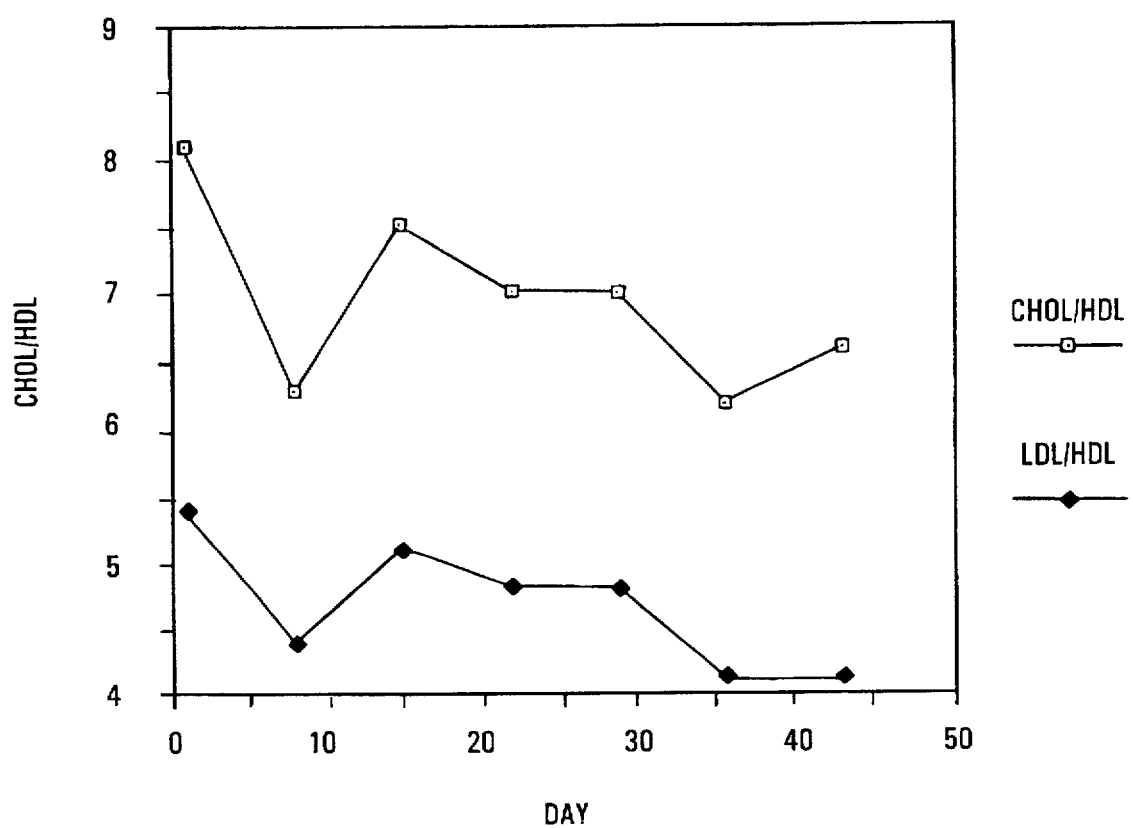
Figure 12A:
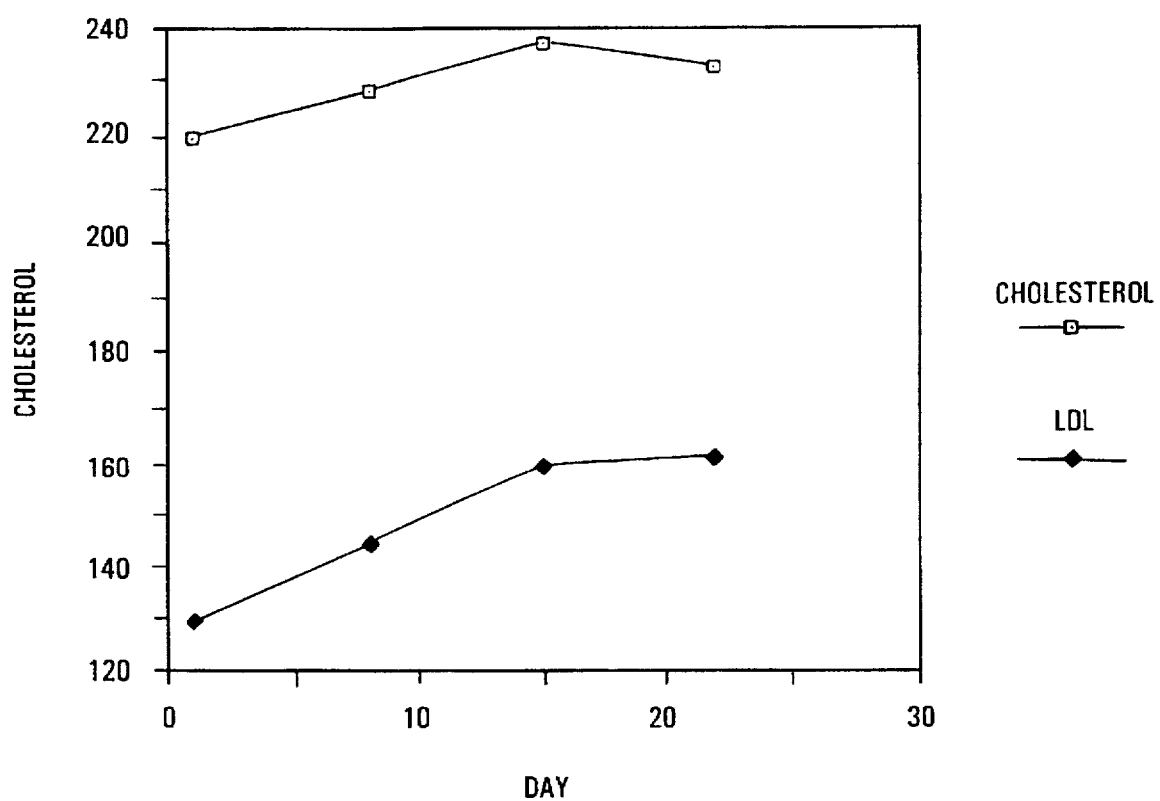
FIGS. 12–14 Panels A–C detail plasma cholesterol levels for Patients #12–#14, respectively.
Figure 12B:
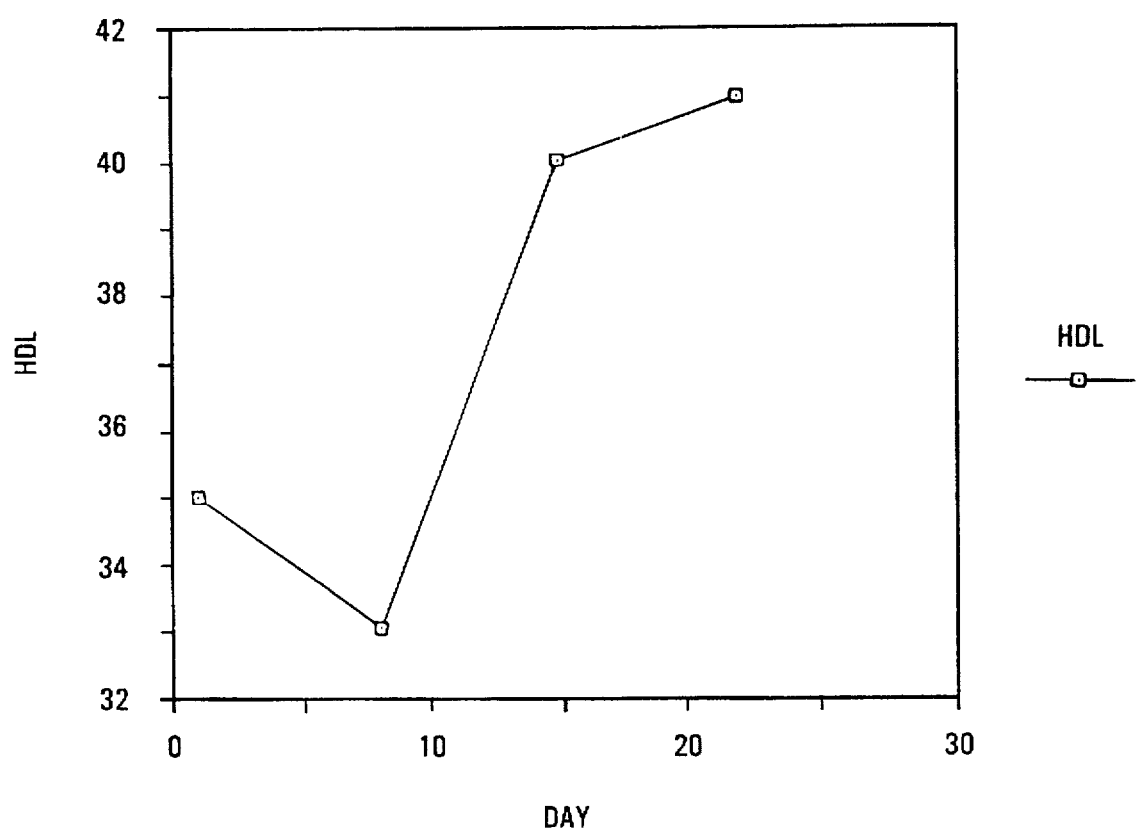
Figure 12C:
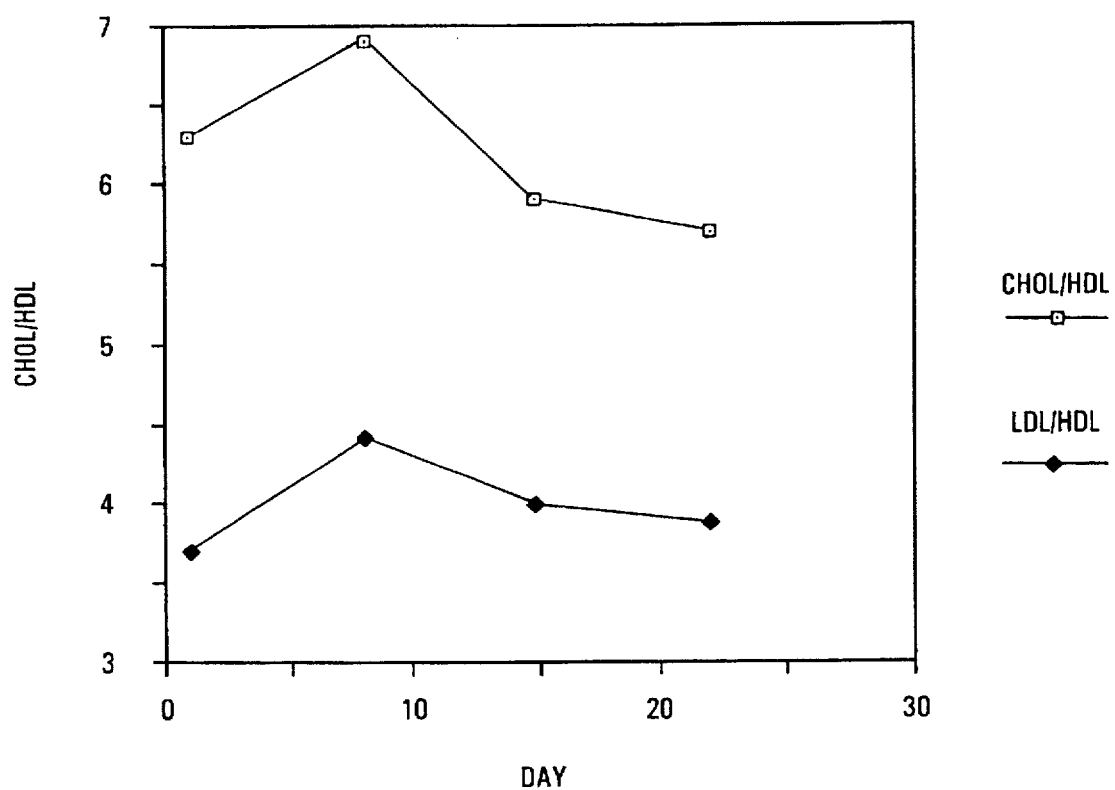
Figure 13A:
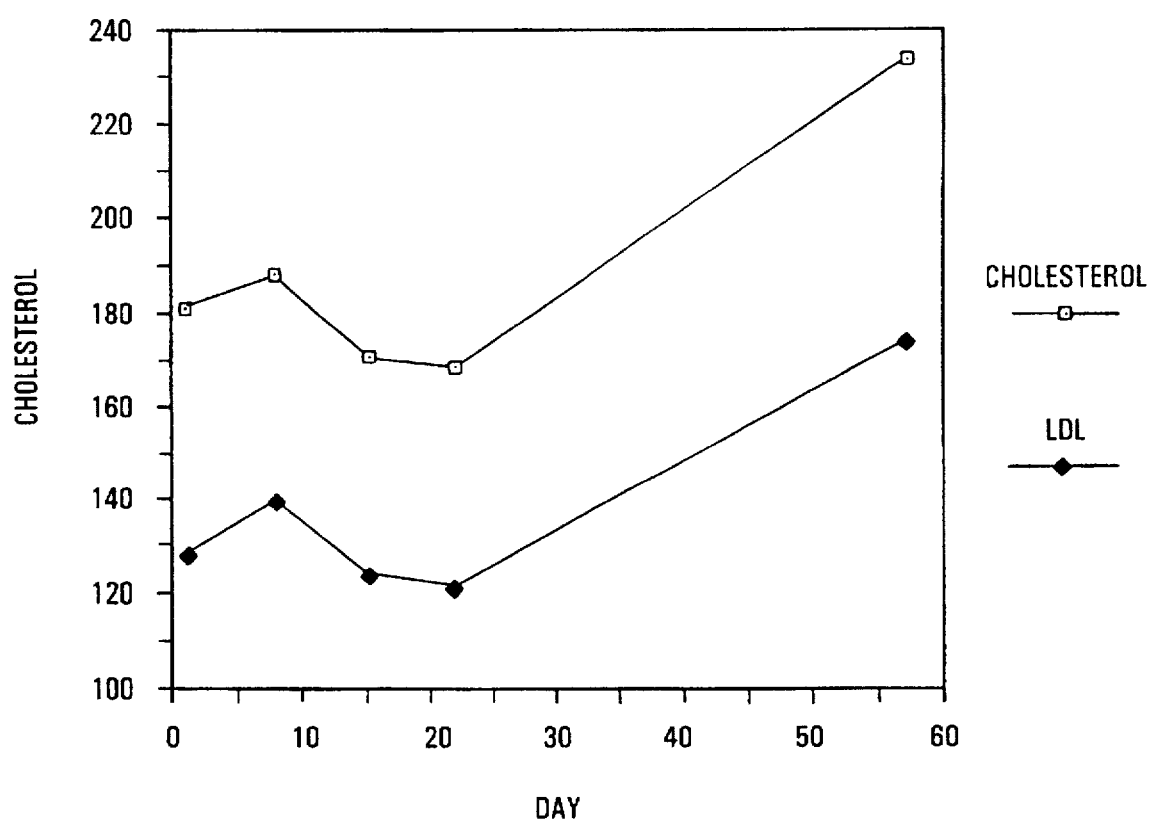
Figure 13B:
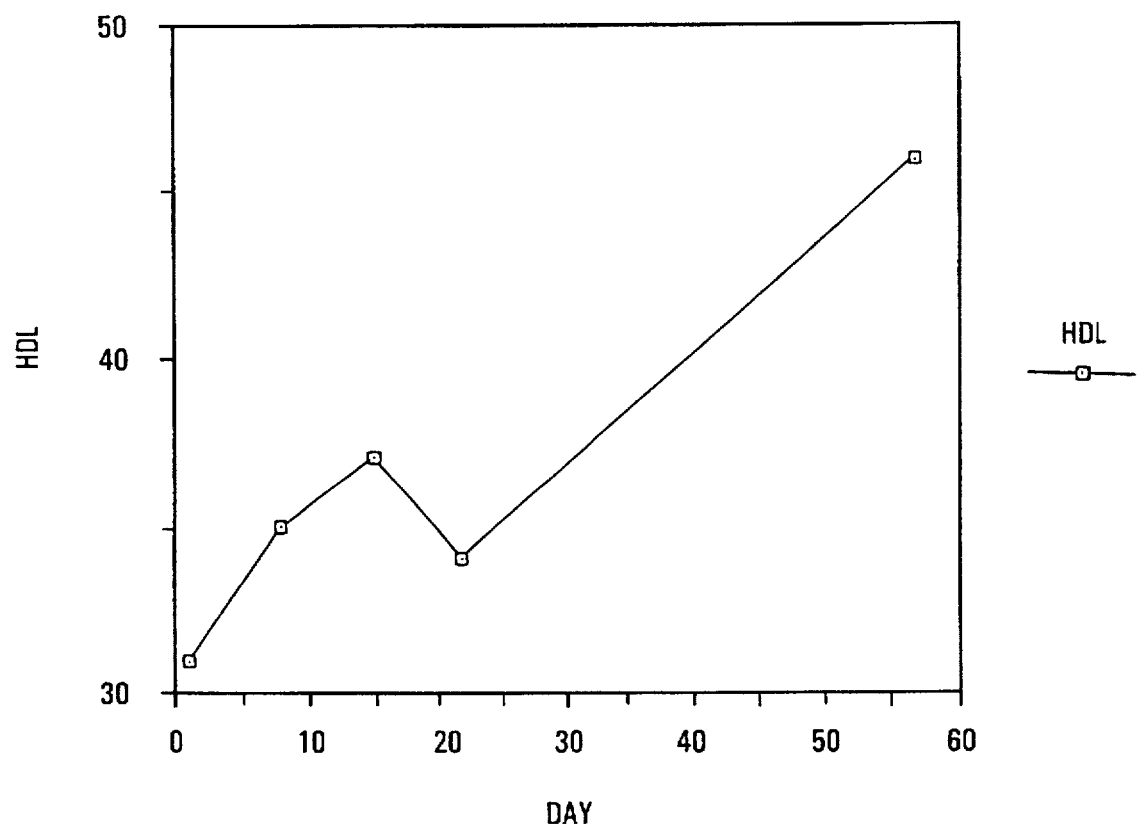
Figure 13C:
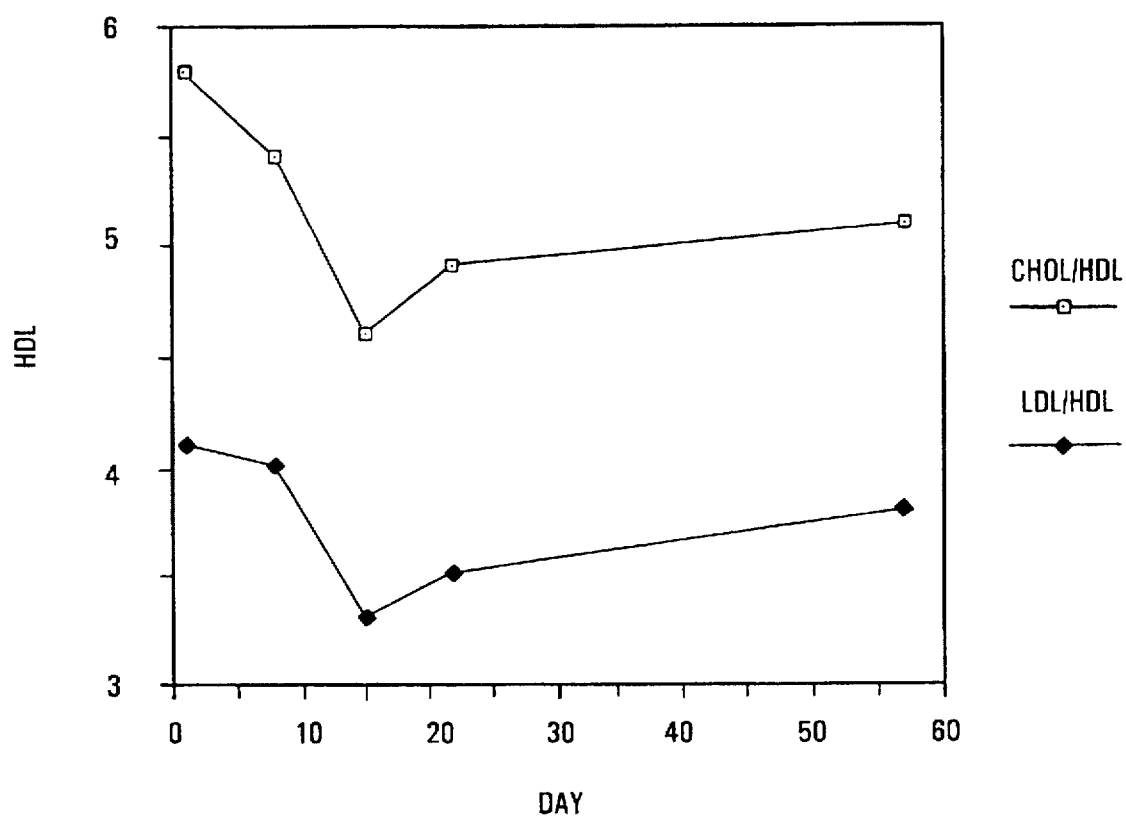
Figure 14A:
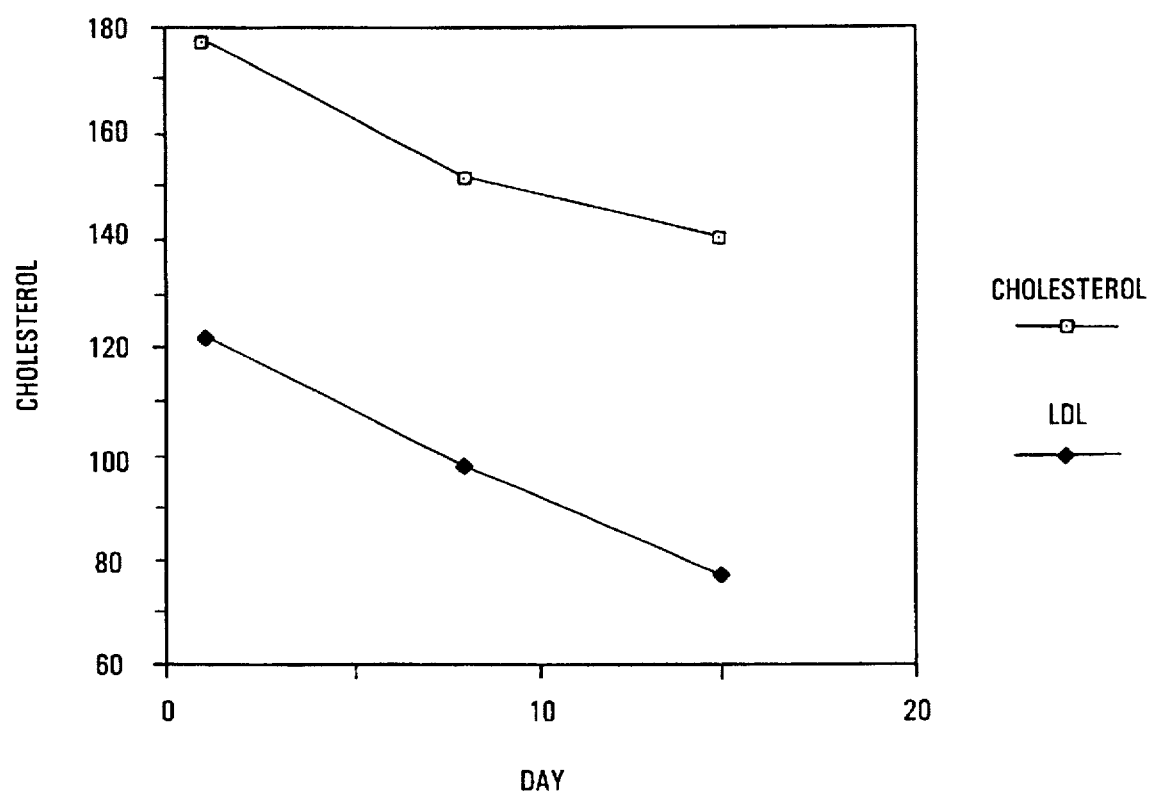
Figure 14B:
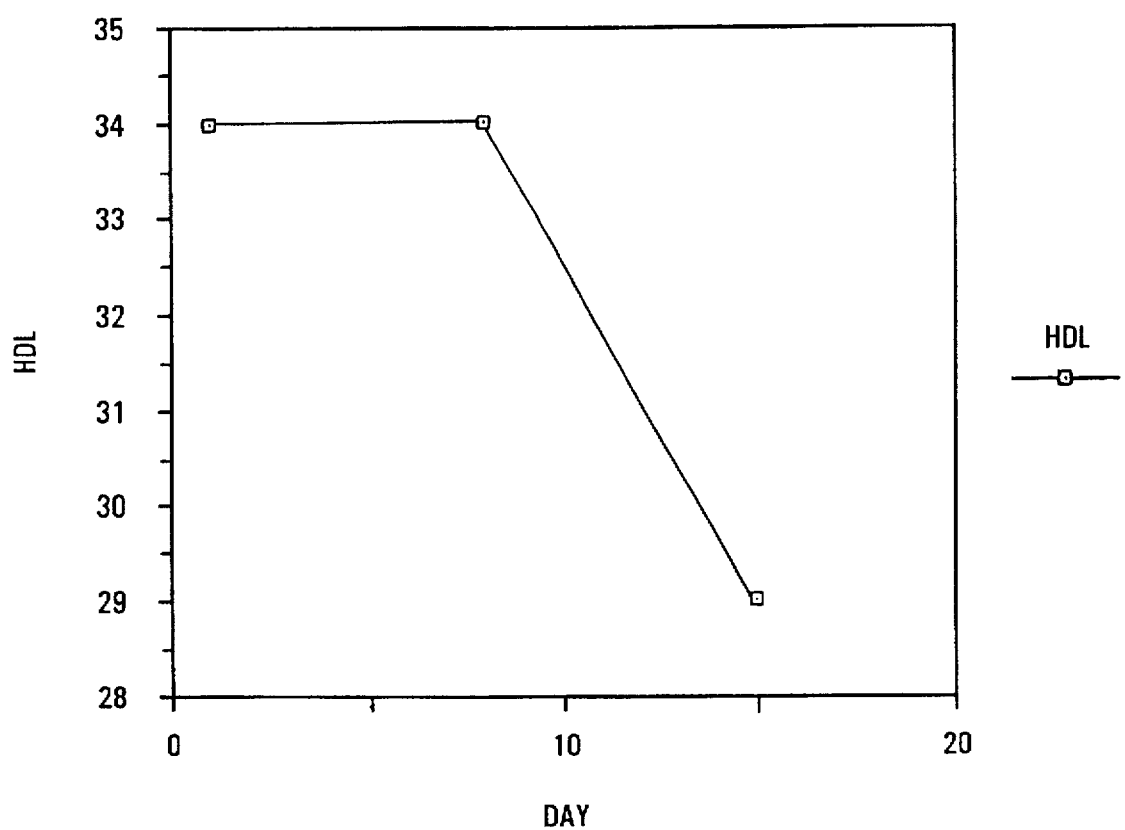
Figure 14C:
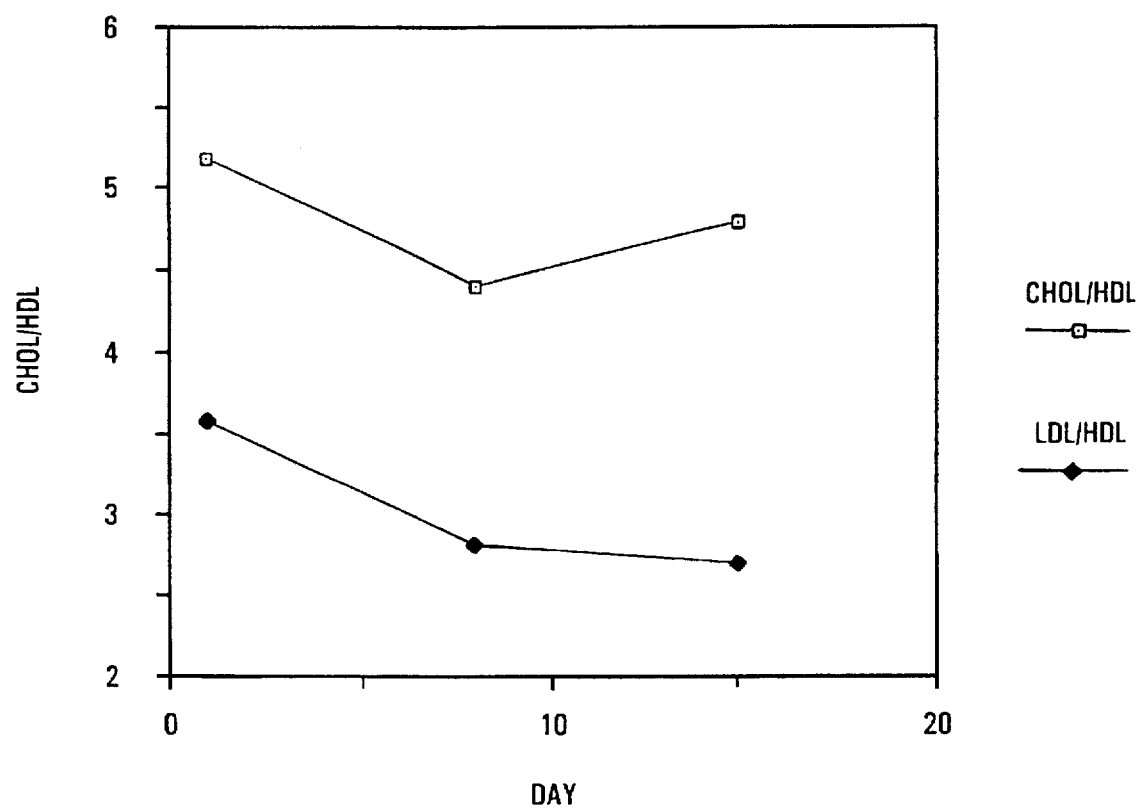
Figure 15A:
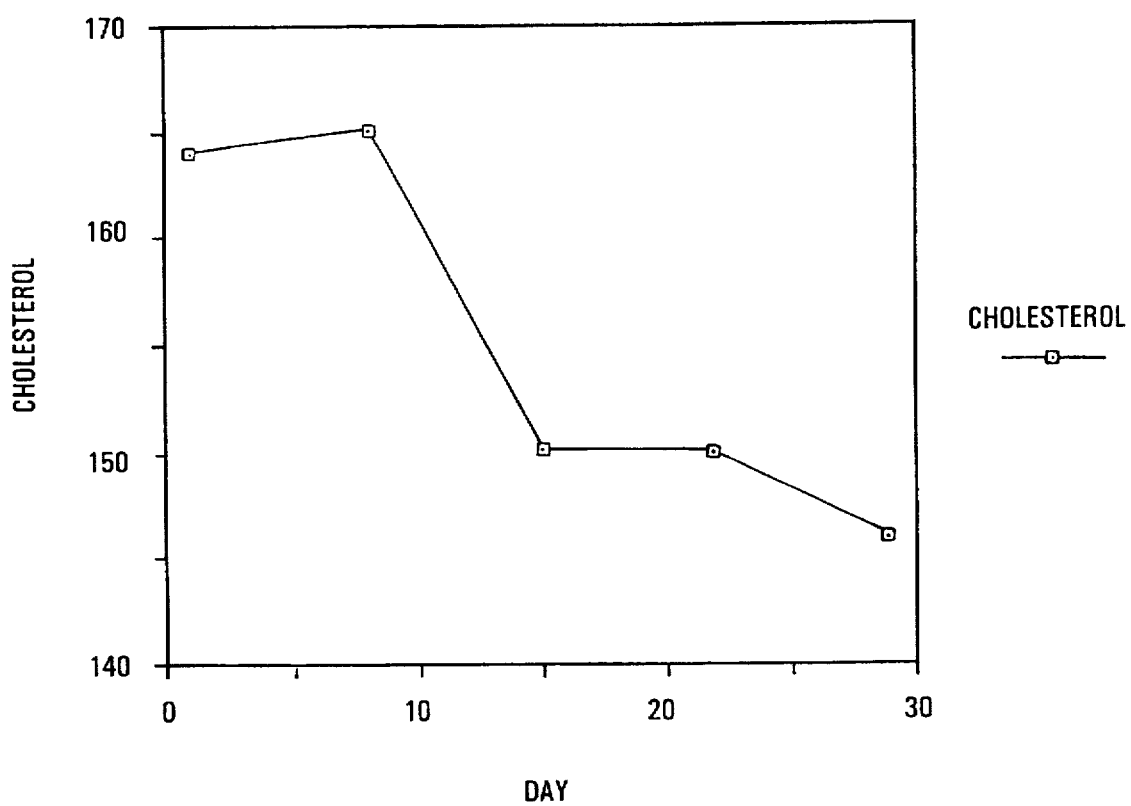
FIGS. 15–17 Panels A–D detail plasma cholesterol levels for Patients #15–#17, respectively.
Figure 15B:
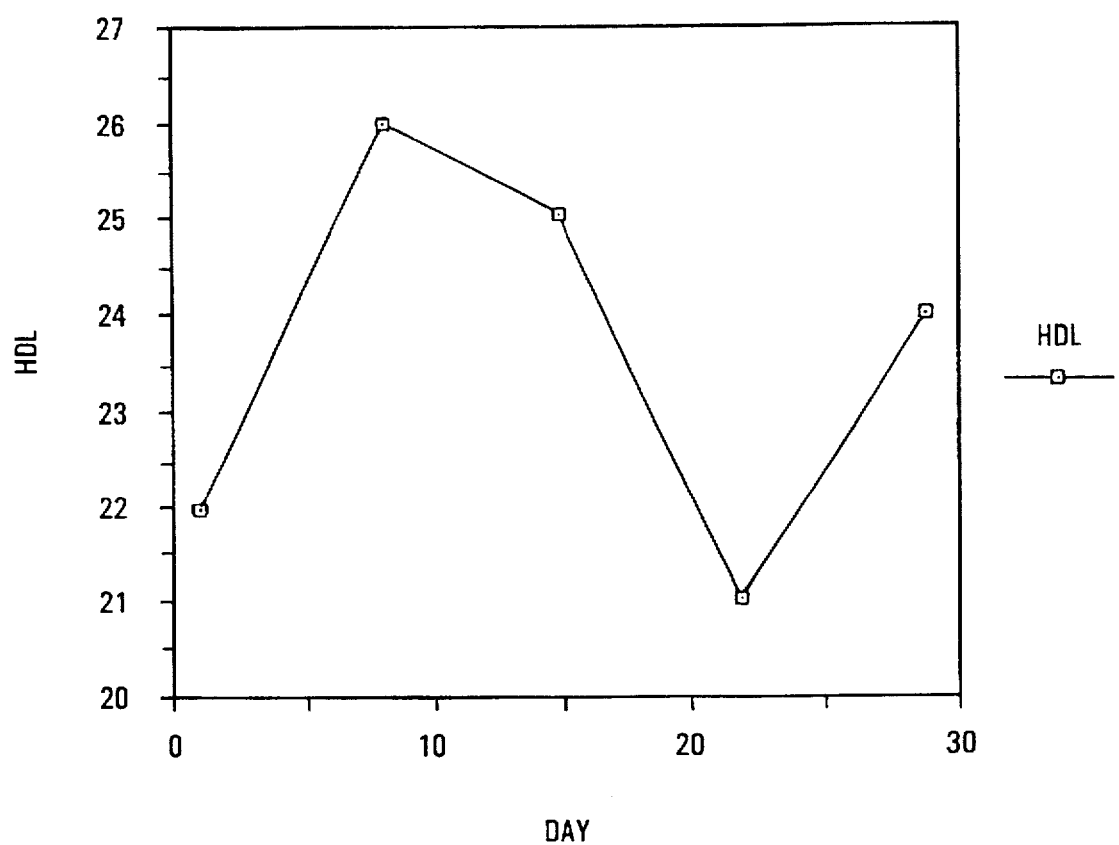
Figure 15C:
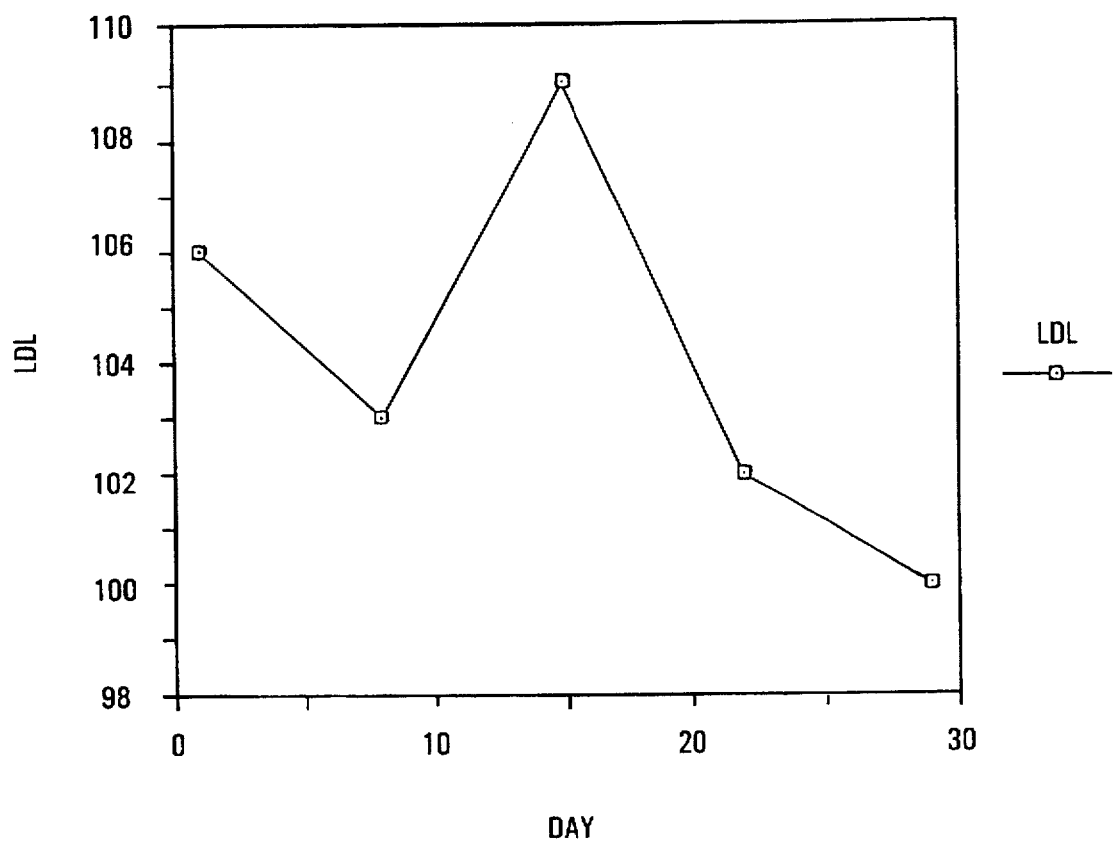
Figure 15D:
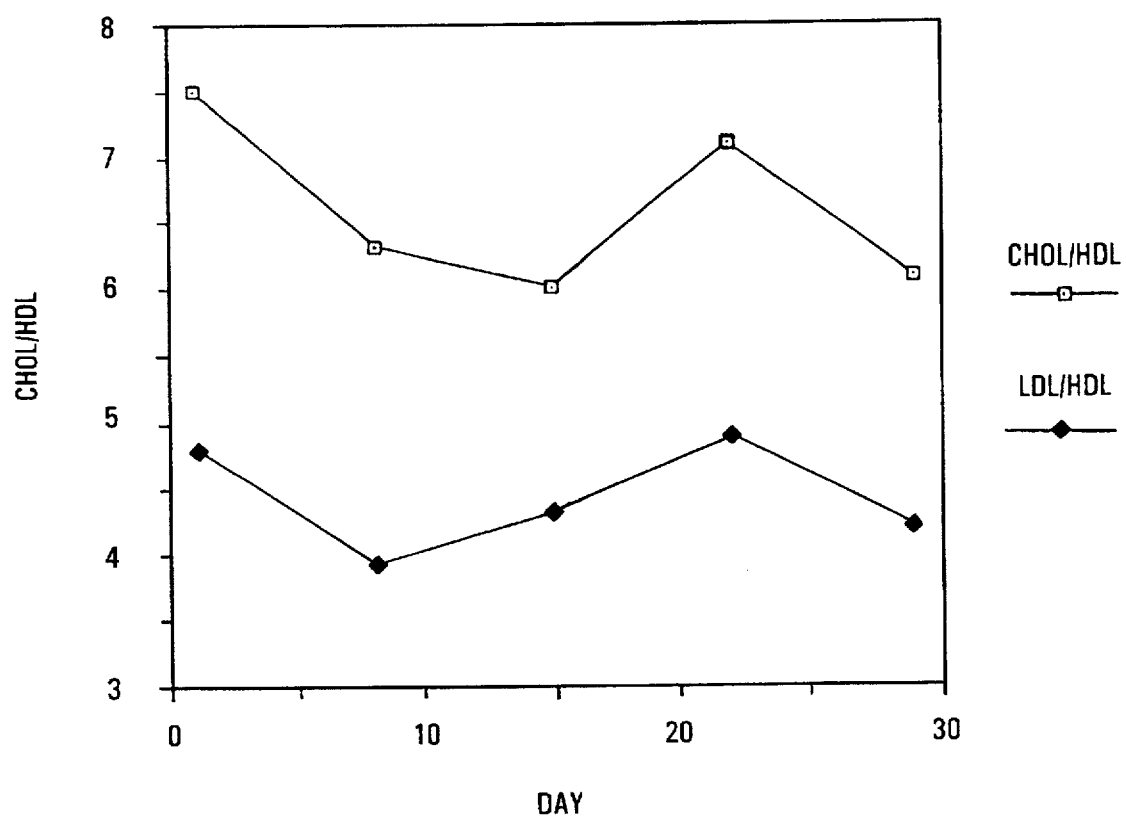
Figure 16A:
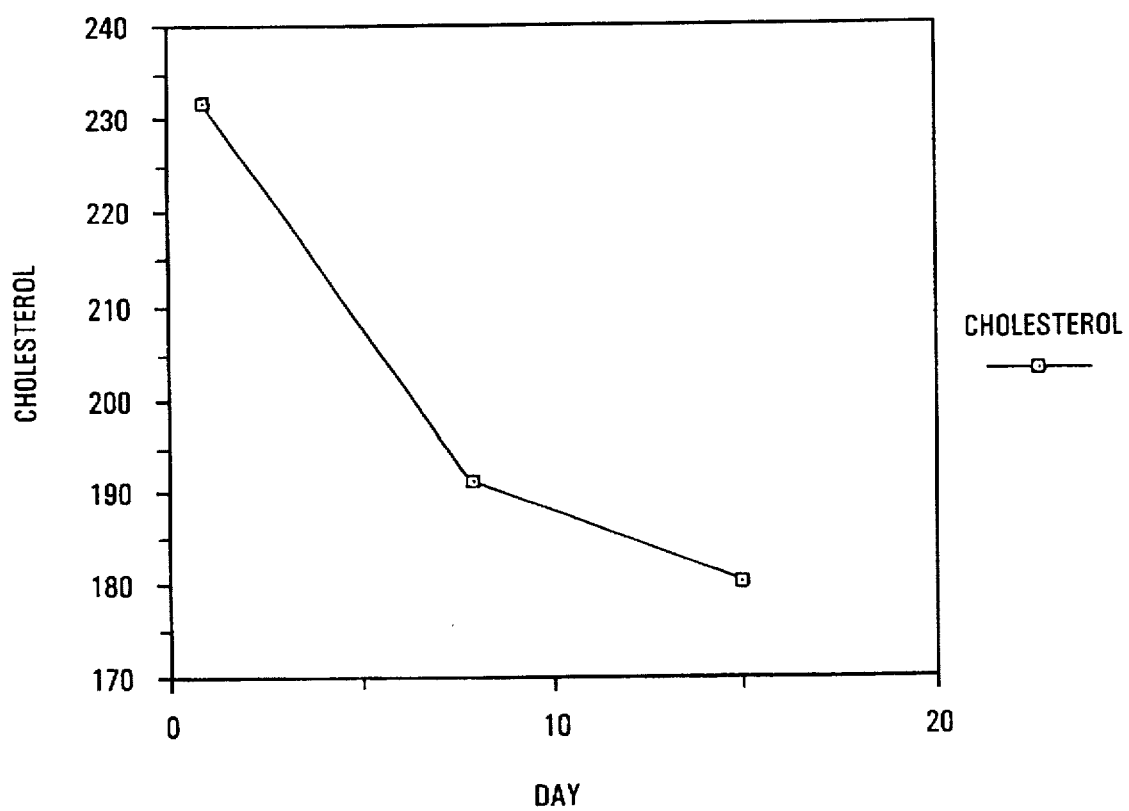
Figure 16B:
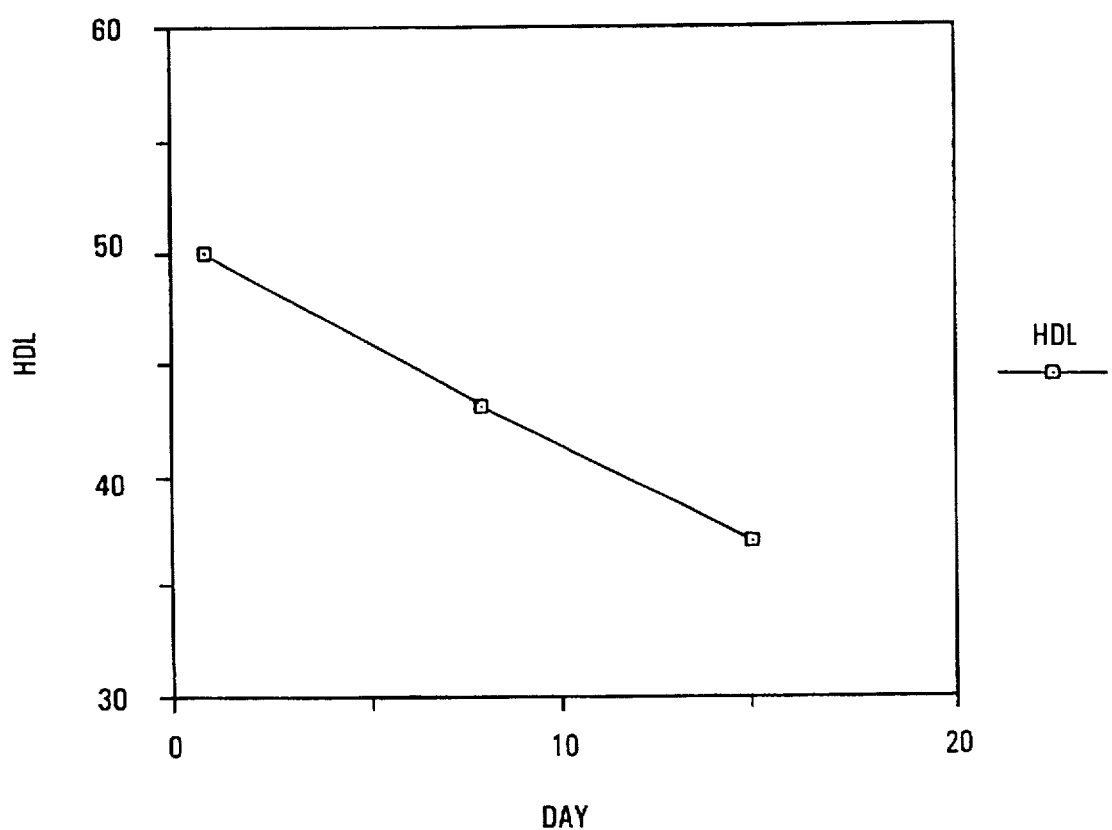
Figure 16C:
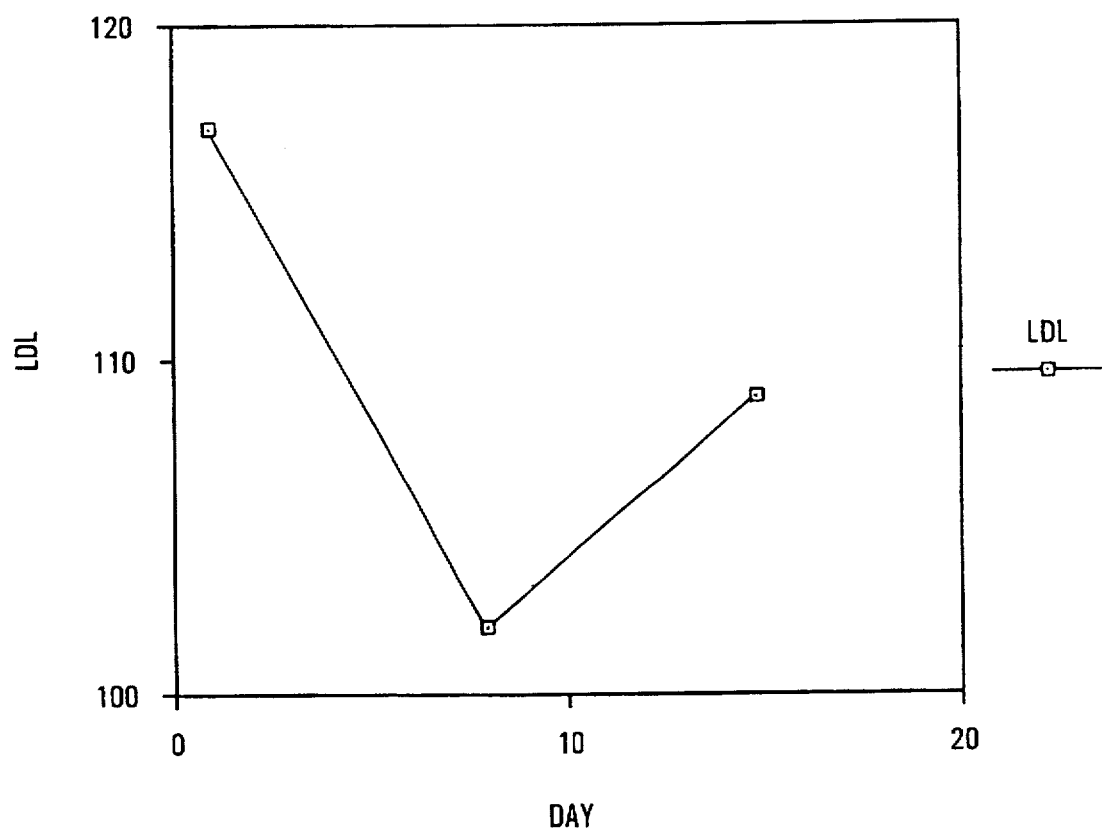
Figure 16D:
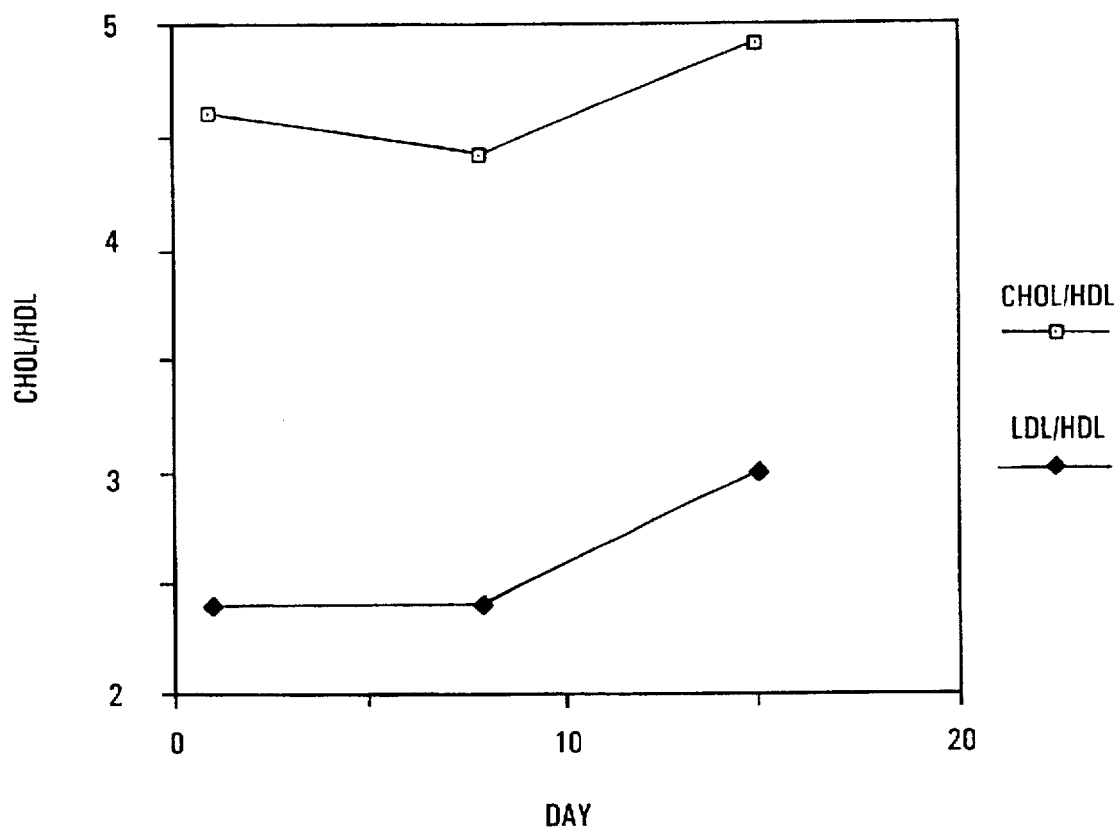
Figure 17A:
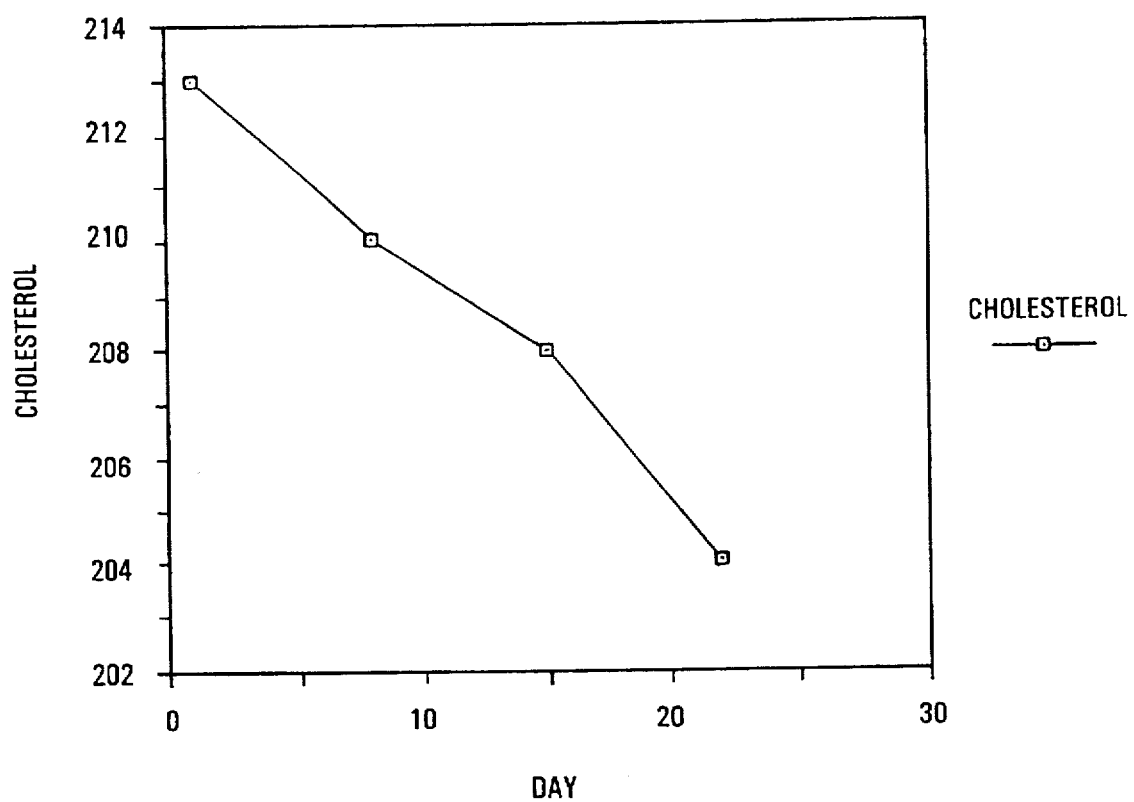
Figure 17B:
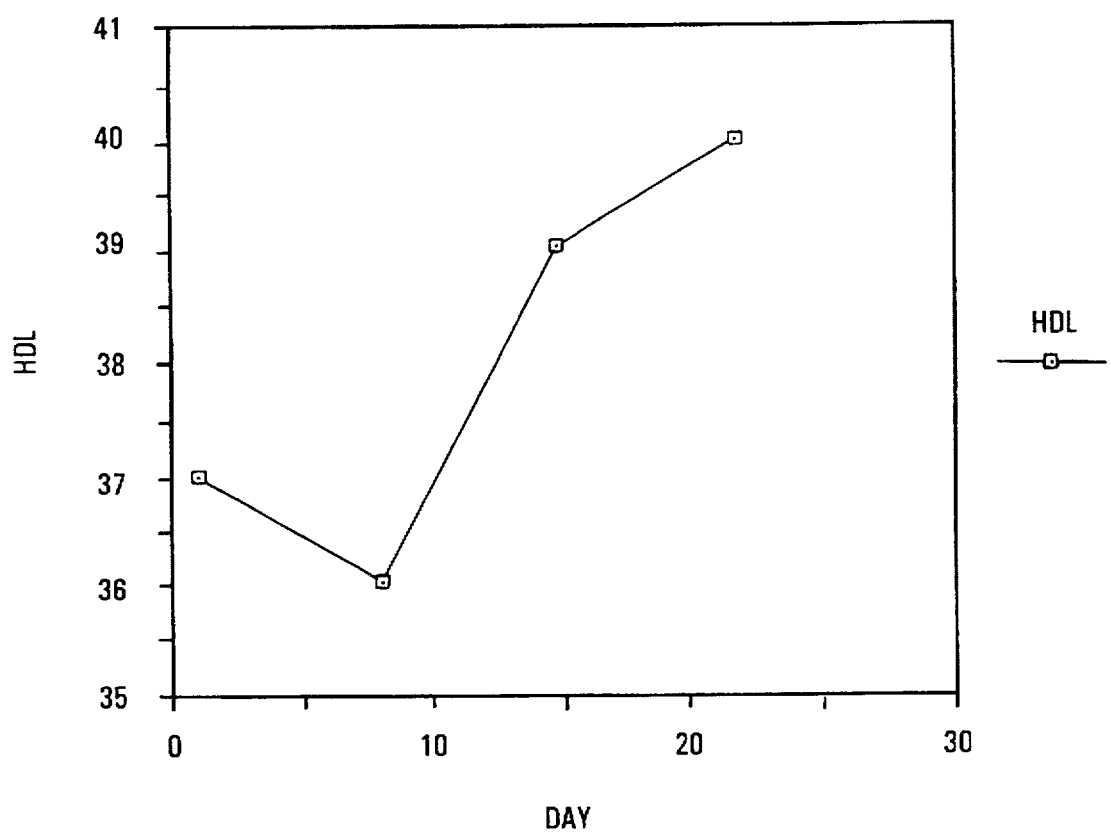
Figure 17C:
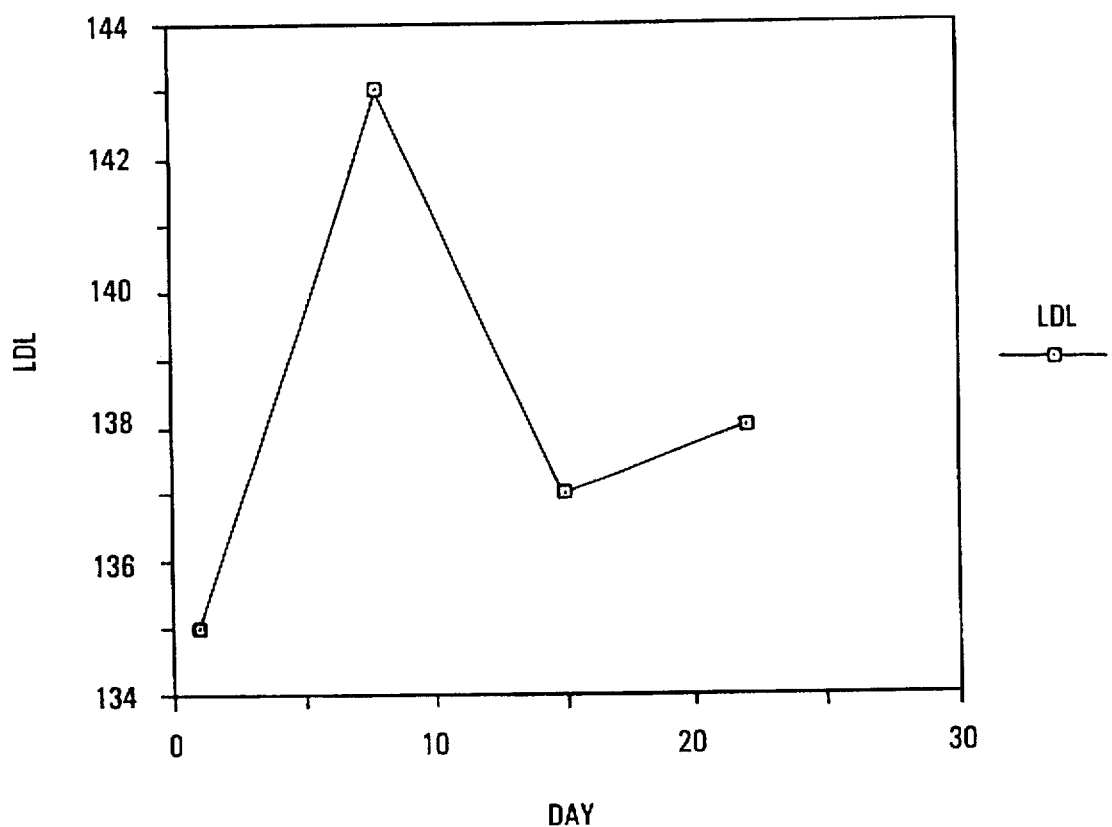
Figure 17D:
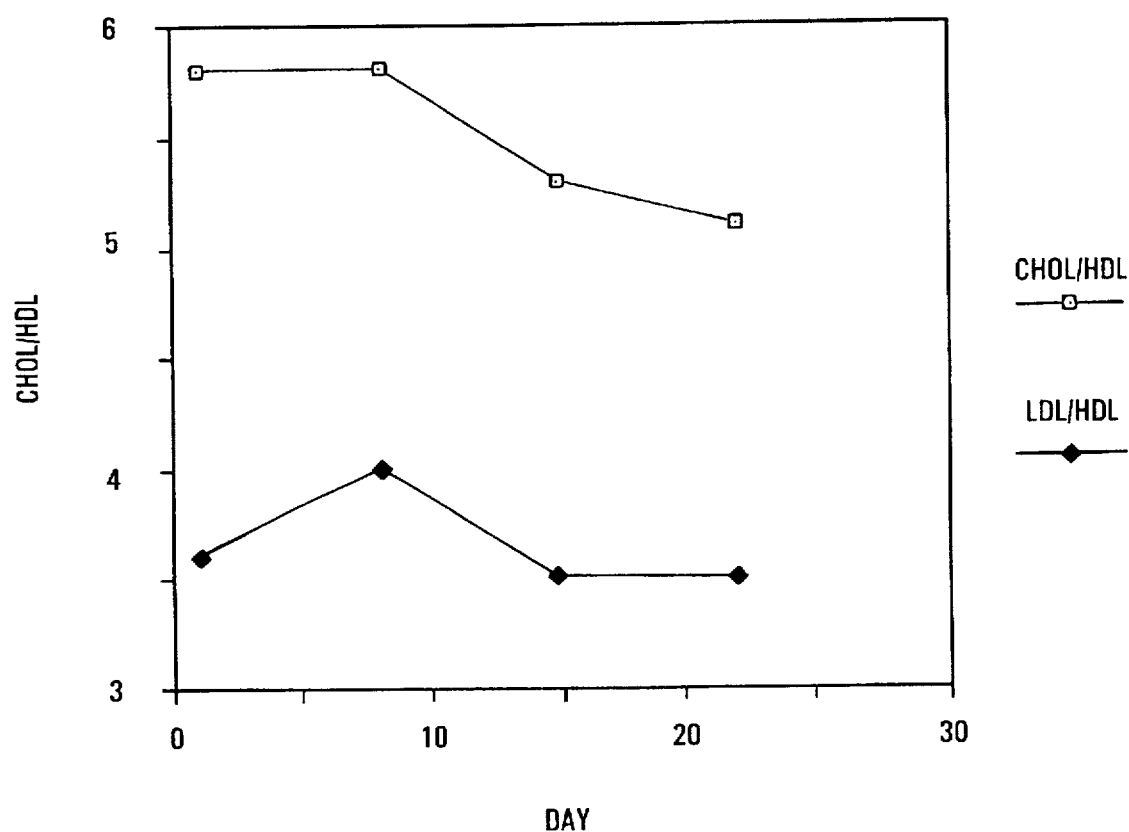
Figure 18A:
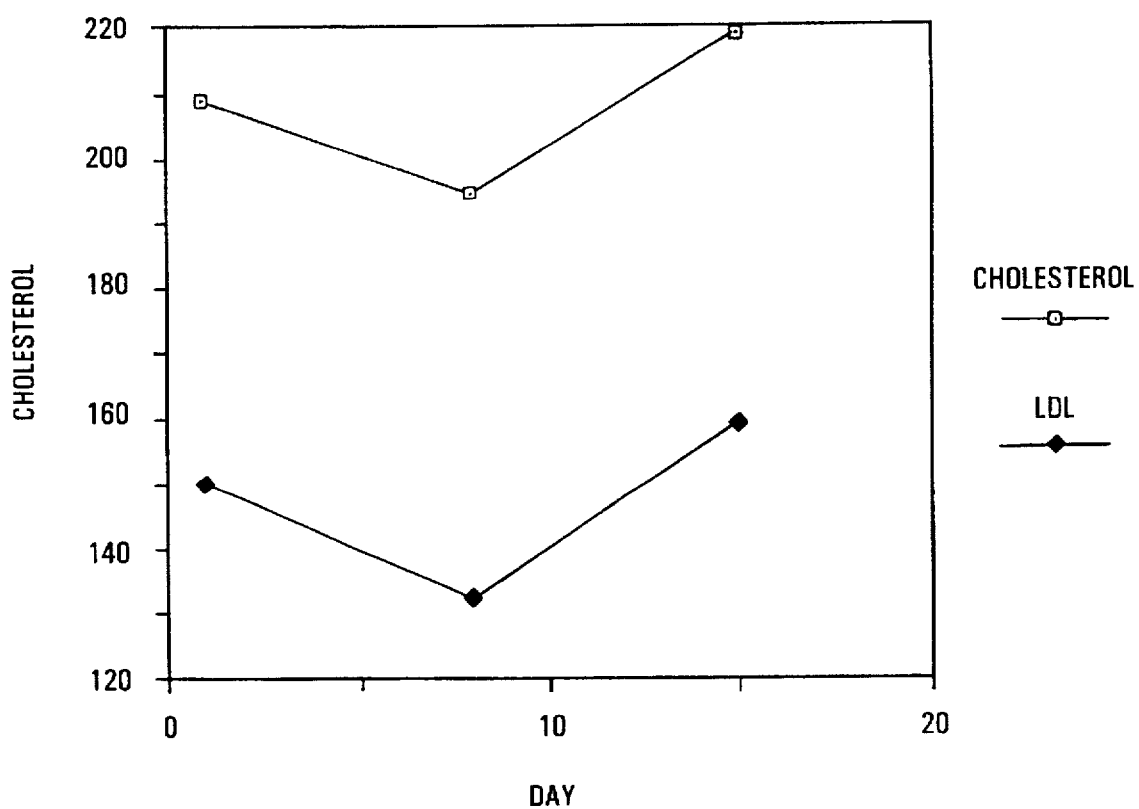
FIG. 18 Panels A–C detail plasma cholesterol levels for Patient #18.
Figure 18B:
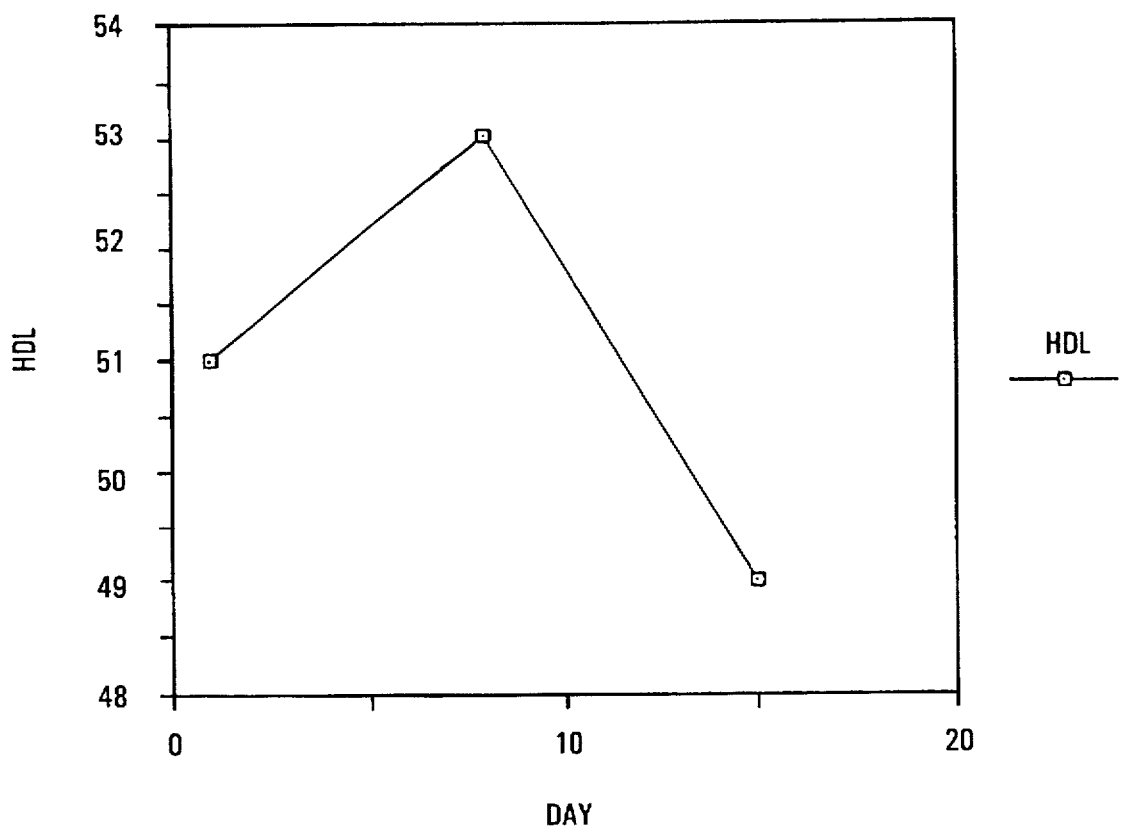
Figure 18C:
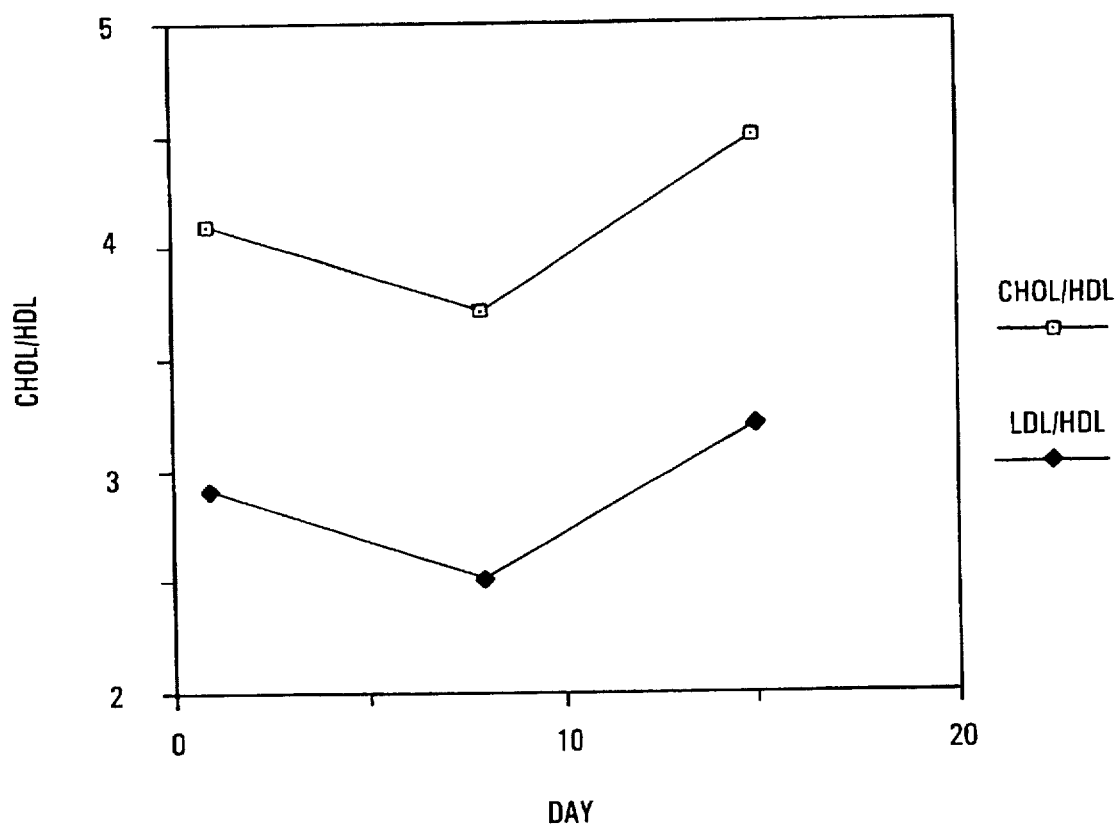
Figure 19A:
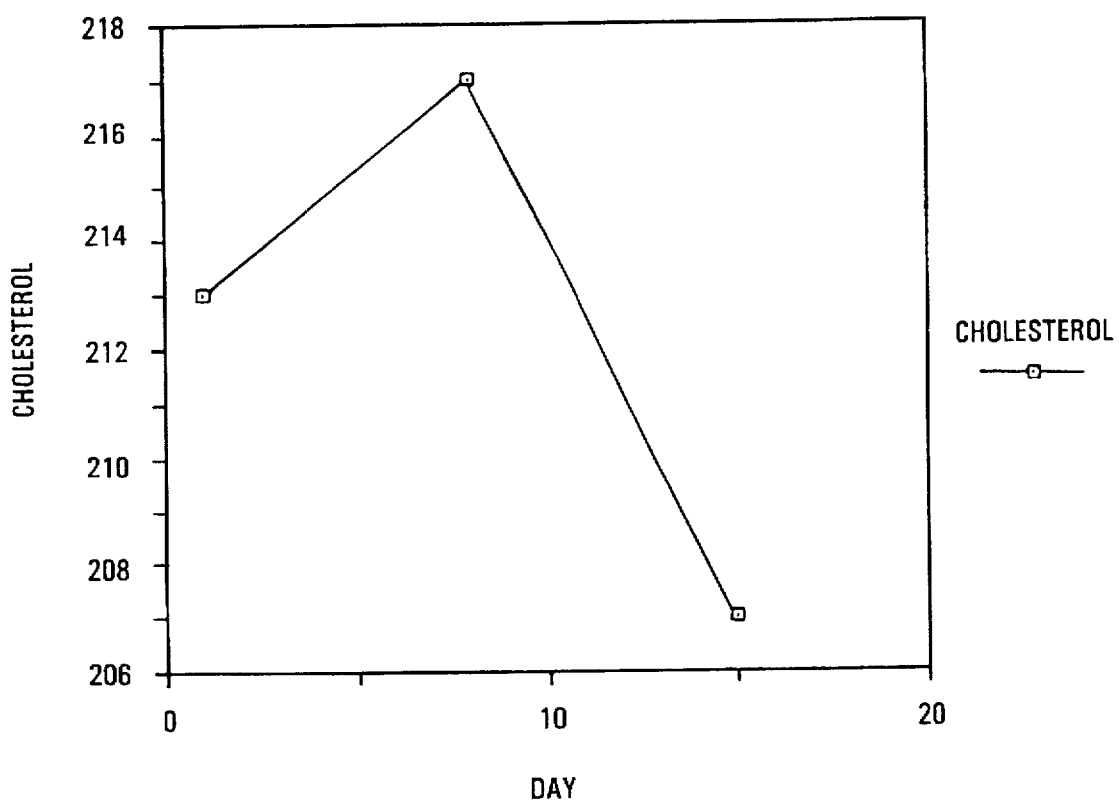
FIG. 19 Panels A–D detail plasma cholesterol levels for Patient #19.
Figure 19B:
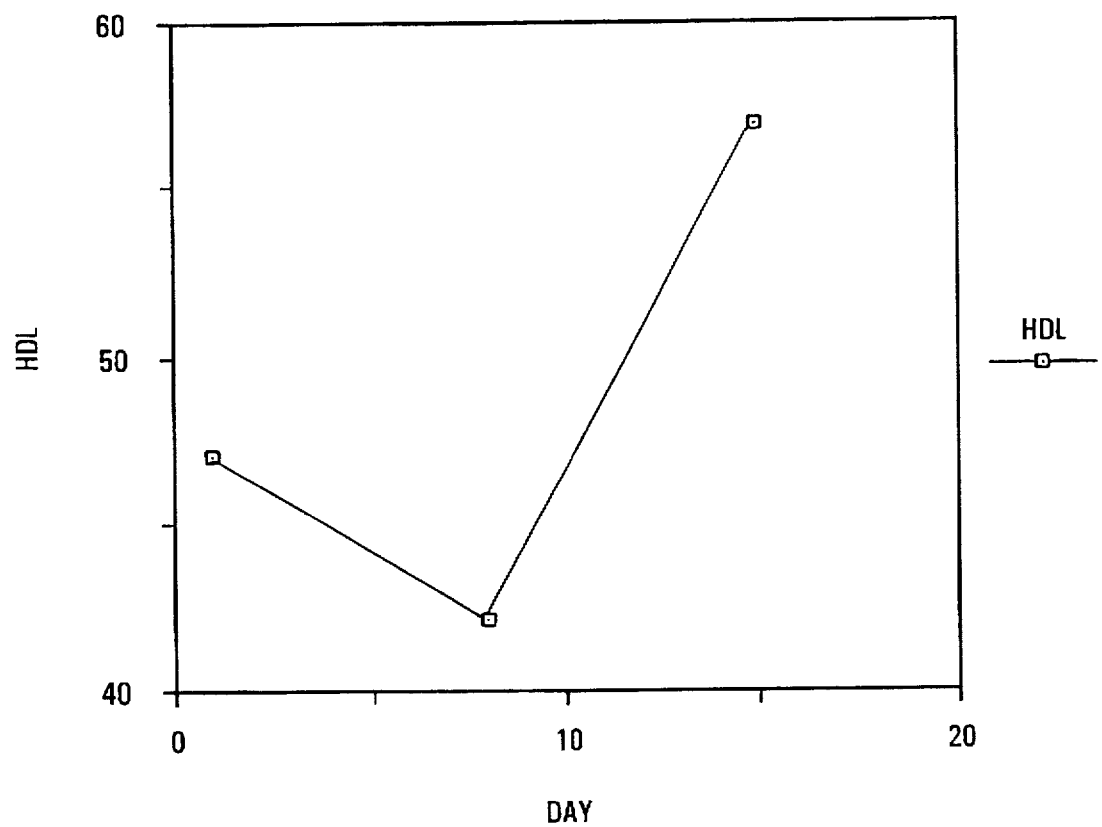
Figure 19C:
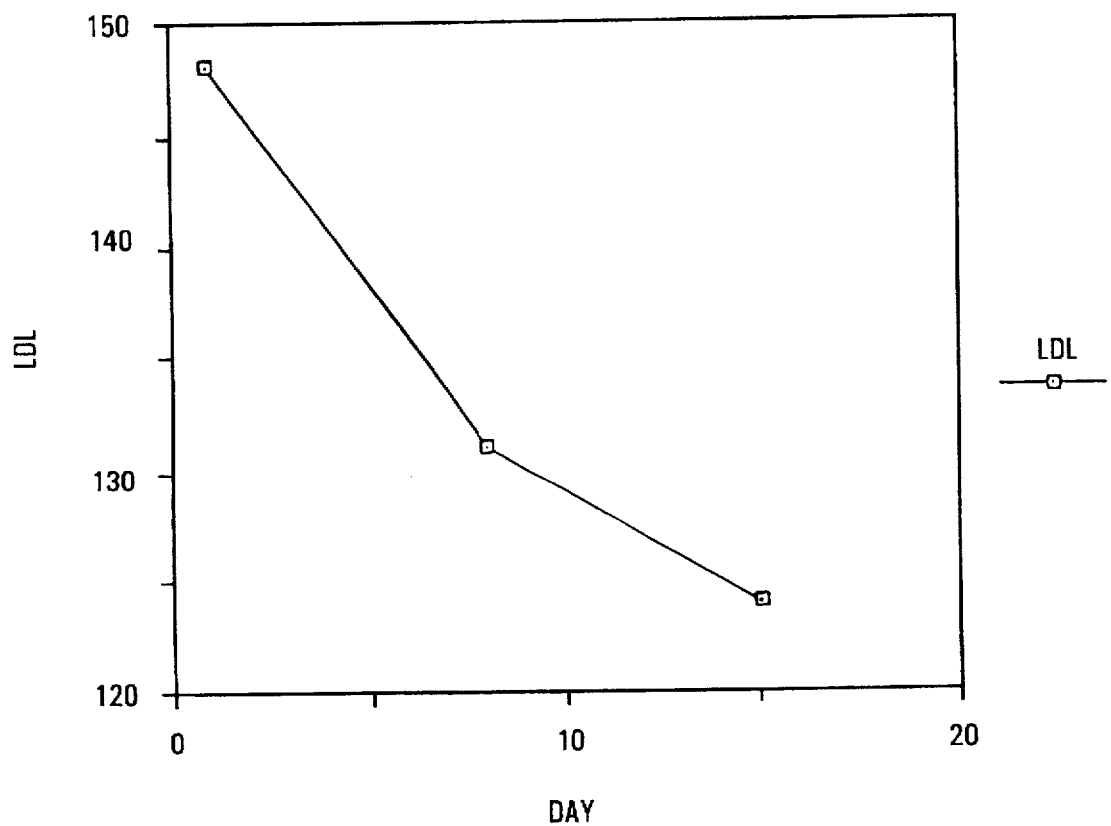
Figure 19D:
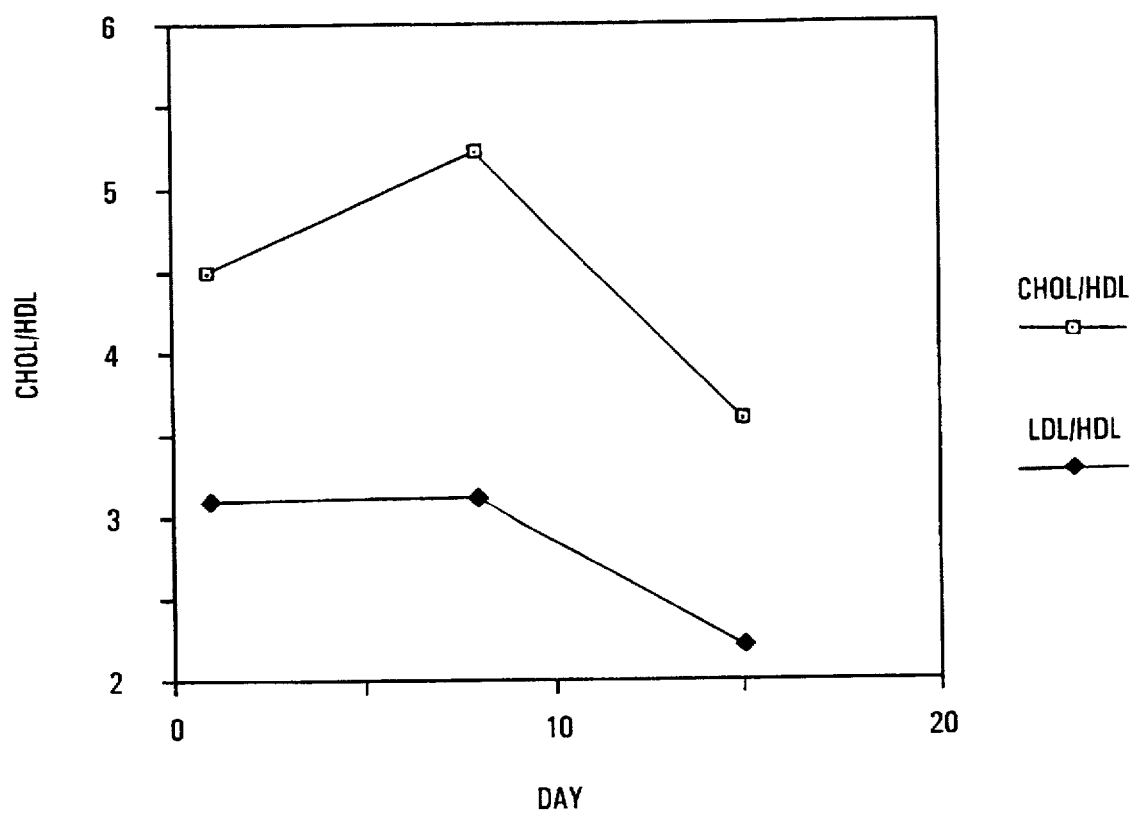
Figure 20A:
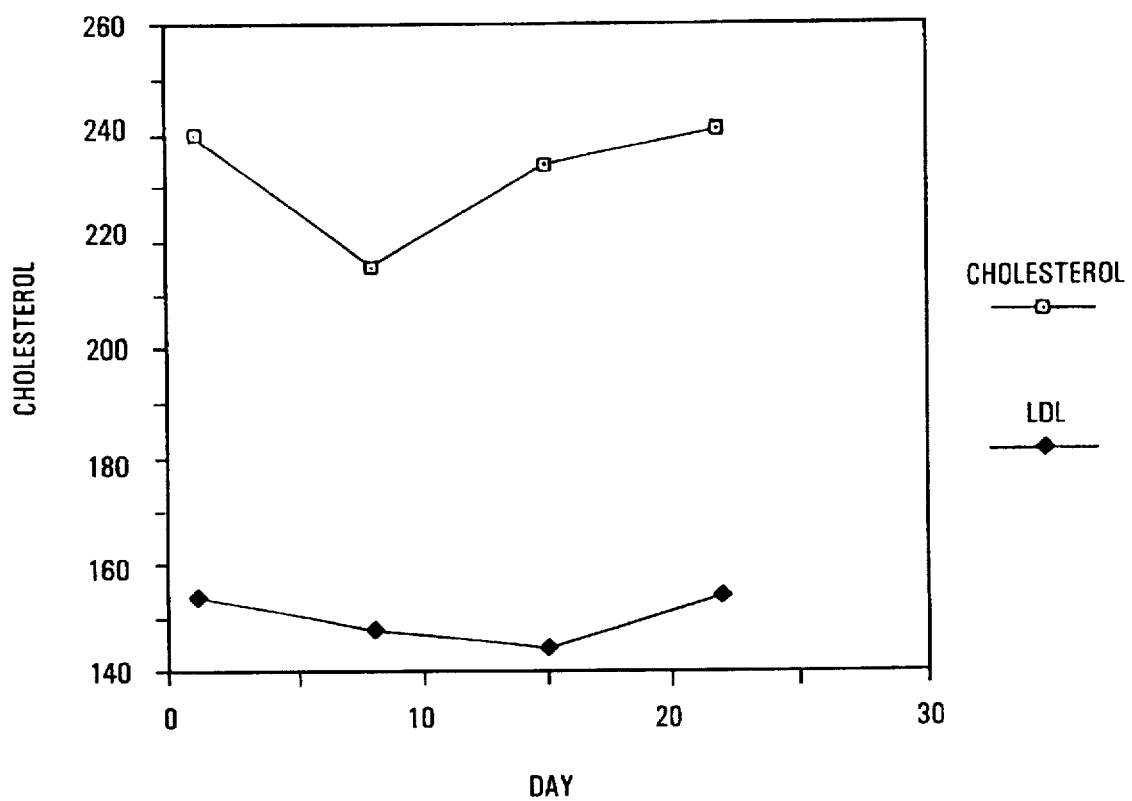
FIG. 20–21 Panels A–C detail plasma cholesterol levels for Patients #20 and 21, respectively.
Figure 20B:
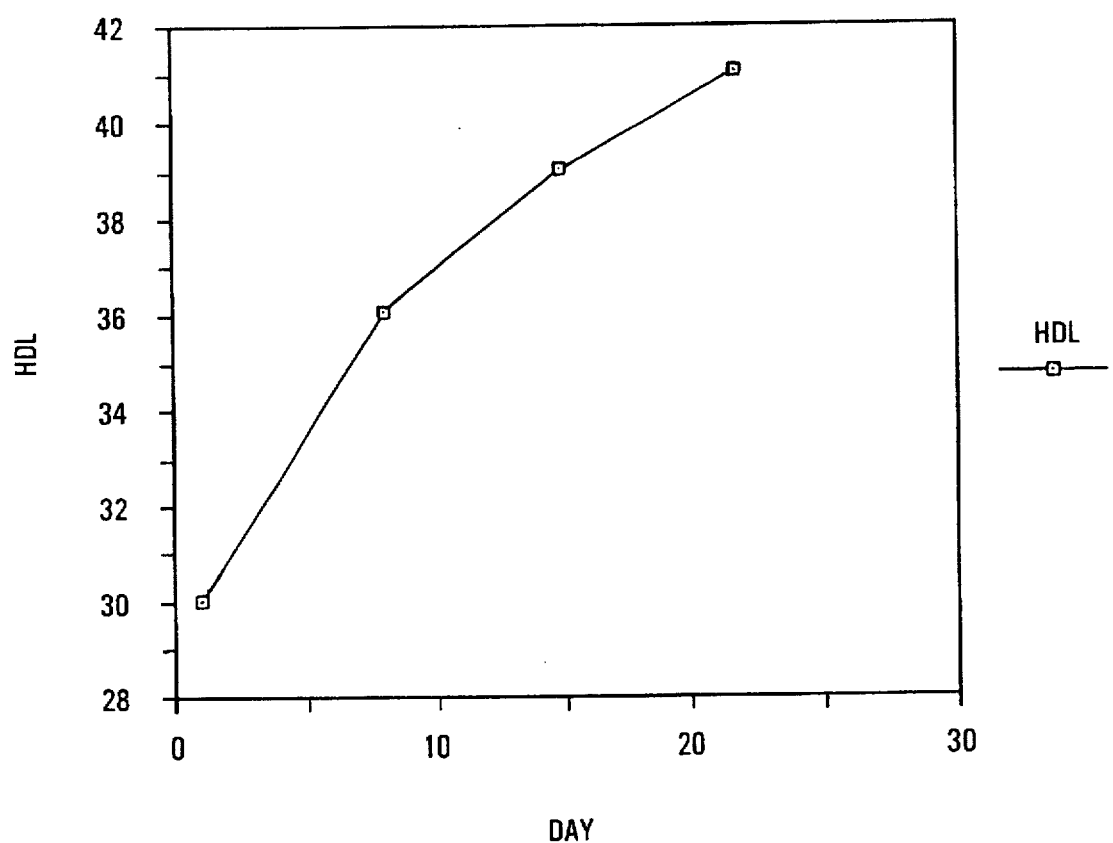
Figure 20C:
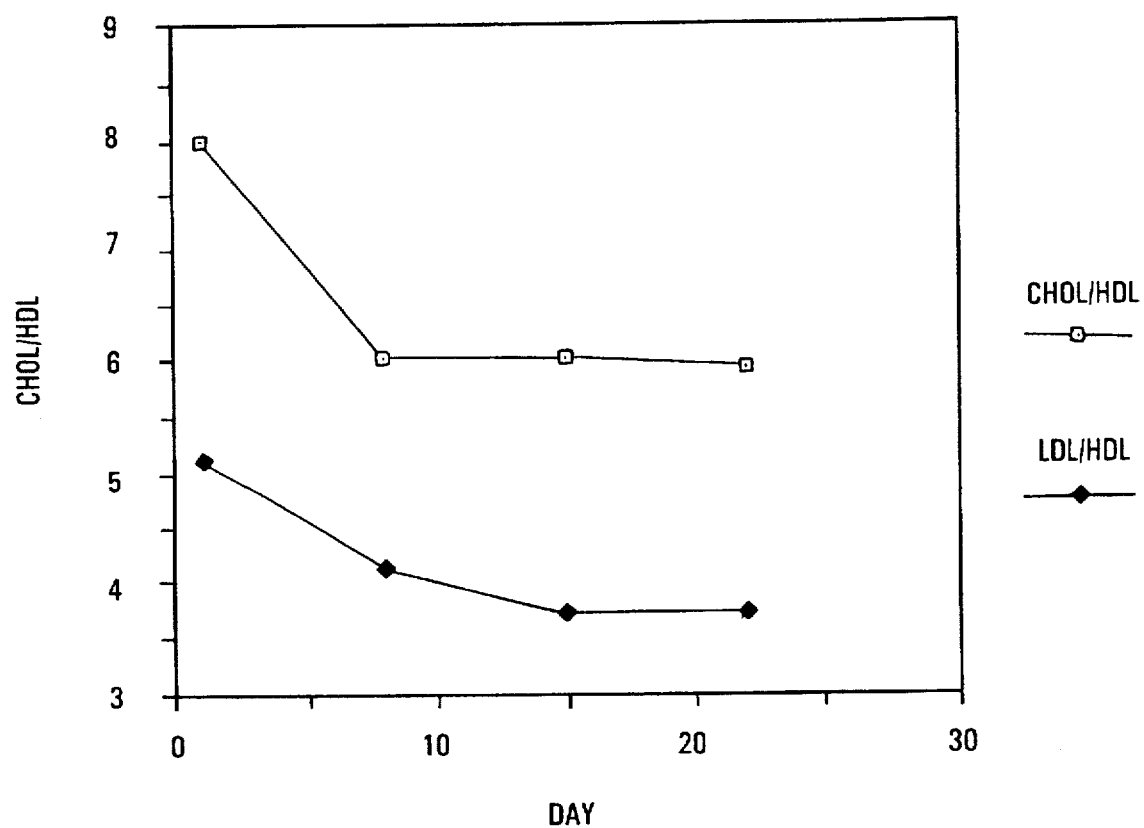
Figure 21A:
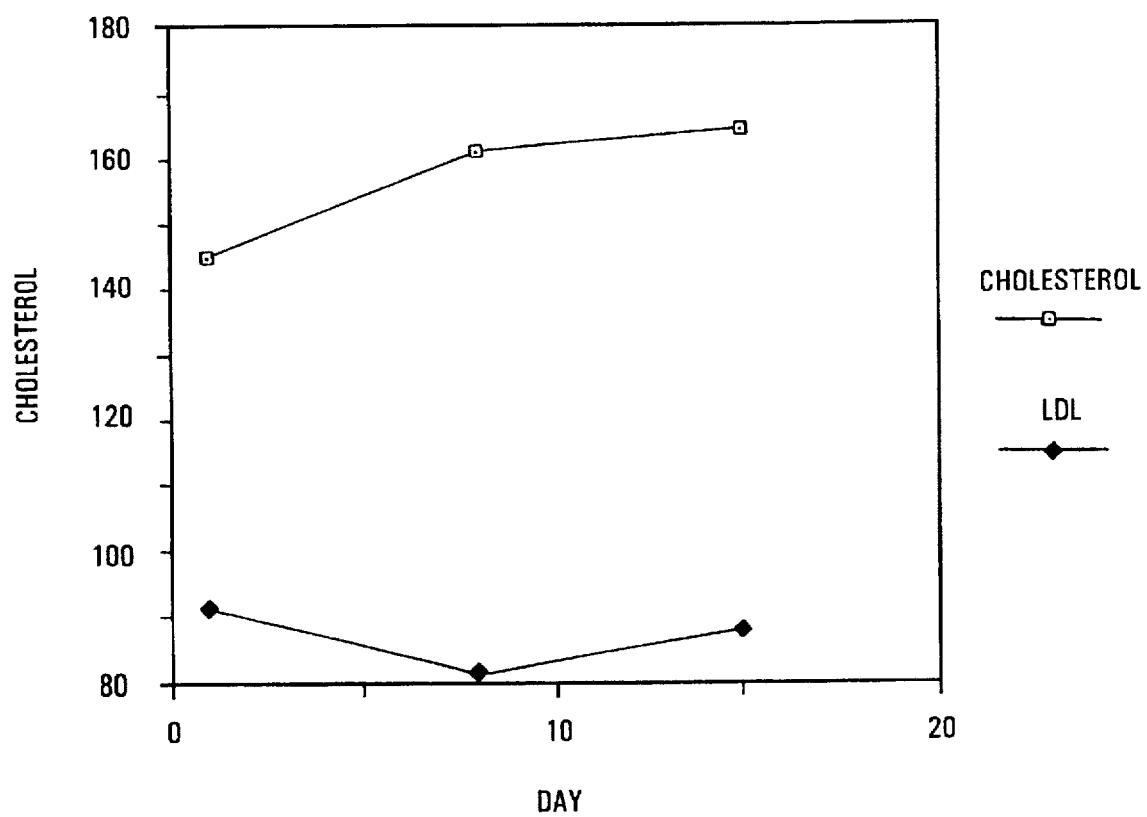
Figure 21B:
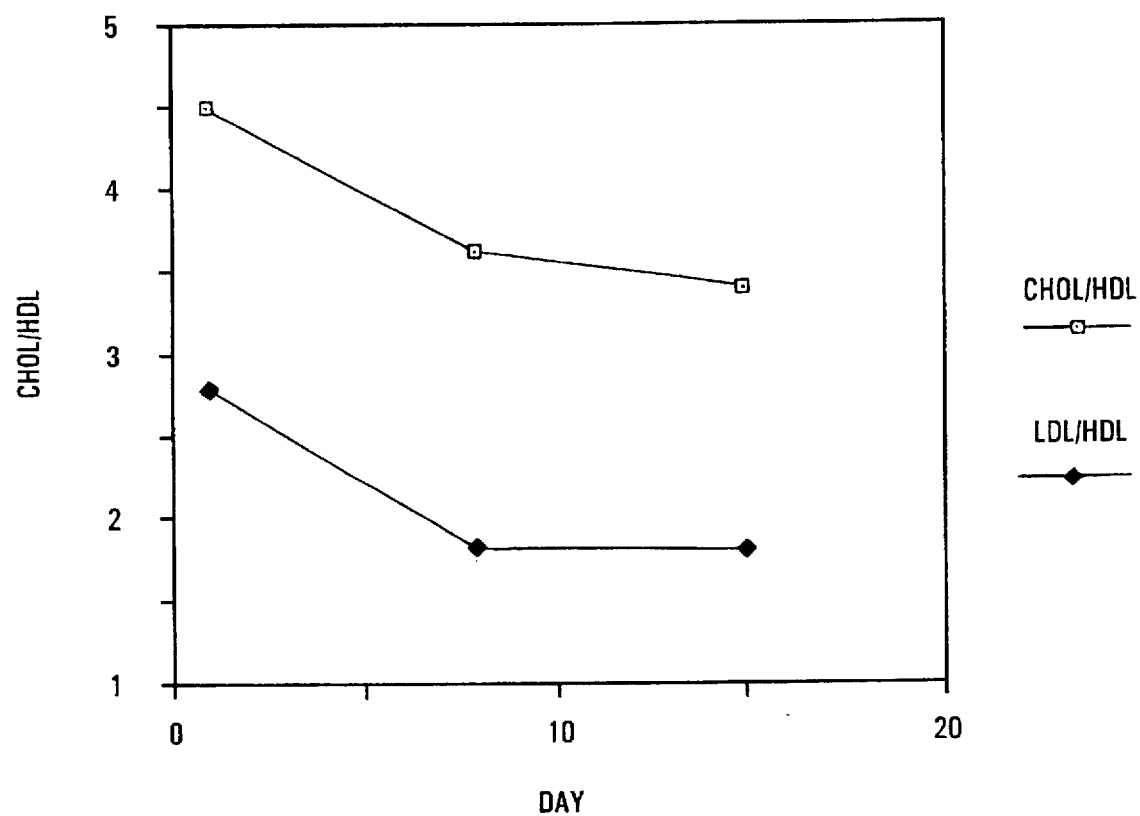
Figure 21C:
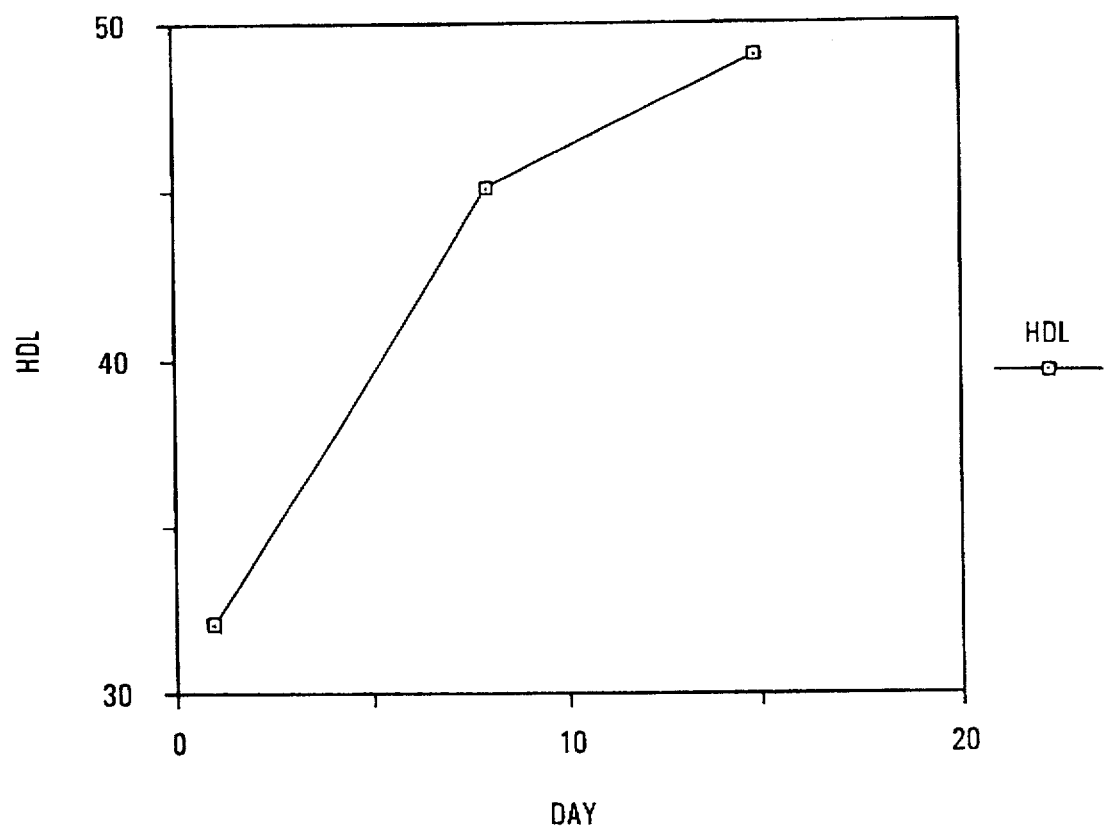

The following references may facilitate understanding or practice of certain aspects of the present invention. Inclusion of a reference in this list is not intended to and does not constitute an admission that the reference represents prior art with respect to the present invention.

Bryskier, A., Agouridas, C., and Chantot, J. F., *Structure and Activity* THE NEW MACROLIDES, AZALIDES, AND STREPTOGRAMINS: PHARMACOLOGY AND CLINICAL APPLICATIONS, 3.3–11 (Neu, H. C., Young, L. S., and Zinner, S. H., eds., 1993.

Fortmann, et al. *Disorders of Lipid Metabolism in Scientific American Medicine*, Metabolism 9-II:14–15, 1993.

Furuchi, et al, *Bafilomycin A1, A Specific Inhibitor or Vacuolar-type H+-ATPase, Blocks Lysosomal Cholesterol Trafficking in Macrophages*, Journal of Biological Chemistry, 268:27345–27348, 1993.

Havel, et al, *Management of Primary Hyperlipidemia*, The New England Journal of Medicine, 332 (22):1491–1498, 1995.

Holme, I., Enger, S. C., Helgeland, A., Hjermann, I., Lerin, P., Lund-Larsen, P. G., Soleberg, L. A., and Strong, J. P.: *Risk factors and raised atherosclerotic lesions in coronary and cerebral arteries. Statistical analysis from the Oslo Study*, Arteriosclerosis 1:250–256, 1991.

Kannel, W. B., Sorlie, P., Brand, F. Castelli, W. P., McNamara, P. M., Gherardi, G. J.: *Epidemiology of coro-* nary atherosclerosis: Postmortem vs clinical risk factor correlation's. The Framingham Study. In: Gotto, A. M., Jr., Smith, L. C., Allen, B., eds. International Symposium on atherosclerosis, 5th, Houston, 1079. Atherosclerosis V. New York Springer-Verlag, pp. 54–56, 1980.

Kawashima, et al, New Cholesterol Biosynthesis Inhibitors . . . , Journal of Antibiotics, 45(1):207–212, 1992.

Lipids Research Clinics Program, The Lipid Research Clinics Coronary Primary Prevention Trial Results. I. Reduction in incidence of coronary heart disease, JAMA 251:351–364, 1984.

McGill, H. C., Jr. McMahan, C. A., Kruski, A. W., and Mott, G. E.: Relationship of lipoprotein cholesterol concentrations to experimental atherosclerosis in baboons. Arteriosclerosis 1:3–12, 1981.

Omura (Omura, S., Macrolide Antibiotics—Chemistry, Biology and Practice 1984.

Physicians' Desk Reference®, 405–407, 1789–91, 1994.

Physicians' Desk Reference®, 421–423, 425–427, 449, 651, 935, 937, 1841, 2102, and 2419, 1995.

Rudel L. L. In: The Use of Nonhuman Primates in Cardiovascular Disease, Kalter, S. S (ed.), University of Texas Press, Austin, Texas, pp. 37–57, 1980.

U.S. Pat. No. 4,331,803, Issued to Watanabe, et al.

U.S. Pat. No. 4,482,540, Issued to Gordon et al, Nov. 13, 1984.

Alternative aspects of the present invention are described within the following claims. In addition, modes alternative to oral administration may be used (e.g., intravenous, intramuscular, intraperitoneal, topical, or the like). Moreover, macrolide antibiotic compounds may be administered on a continuous or an intermittent basis.

The foregoing description has been directed to particular embodiments of the invention in accordance with the Patent Statutes for the purposes of illustration and explanation. It will be apparent, however, to those skilled in this art that many modifications, changes and variations in the claimed invention will be possible without departing from the scope and spirit of the claimed invention. It is intended that the following claims be interpreted to embrace all such modifications and changes.

TABLE 2

EFFECT OF CLARITHROMYCIN ON PLASMA CHOLESTEROL LEVELS IN PATIENTS WITH HYPERCHOLESTEROLEMIA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| | | | | PATIENT 1 CHOLESTEROL DATA | | | | | | | |
| 1 | 1.000 | 220.000 | | 36.000 | | 165.000 | | 6.100 | | 4.600 | |
| 2 | 8.000 | 199.000 | −9.500 | 41.000 | 13.900 | 141.000 | −14.500 | 4.900 | −17.400 | 3.400 | −26.100 |
| 3 | 24.000 | 227.000 | 3.200 | 50.000 | 38.900 | 159.000 | −3.600 | 4.500 | −26.200 | 3.200 | −30.400 |
| | | | | PT. 2 CHOLESTEROL DATA | | | | | | | |
| 1 | 1.000 | 286.000 | | 39.000 | | 183.000 | | 7.300 | | 4.700 | |
| 2 | 8.000 | 284.000 | 0.700 | 37.000 | −5.100 | 190.000 | 3.800 | 7.700 | 5.500 | 5.100 | 7.000 |
| 3 | 15.000 | 267.000 | −7.700 | 35.000 | −10.300 | 164.000 | −10.400 | 7.600 | 4.100 | 4.700 | 0000 |
| 4 | 22.090 | 260.000 | −9.100 | 35.000 | −10.300 | 159.000 | −13.100 | 7.400 | 1.400 | 4.500 | −4.400 |
| 5 | 29.000 | 248.000 | −13.300 | 31.000 | −20.500 | 152.000 | −16.900 | 8.000 | 9.600 | 4.900 | 4.400 |
| | | | | PT. 3 CHOLESTEROL DATA | | | | | | | |
| 1 | 1.000 | 233.000 | | 43.000 | | 164.000 | | 5.400 | | 3.800 | |
| 2 | 8.000 | 230.000 | −5.700 | 41.000 | −4.700 | 166.000 | 12.200 | 5.600 | 3.700 | 4.100 | 7.900 |
| | | | | PT. 4 CHOLESTEROL DATA | | | | | | | |
| 1 | 1.000 | 358.000 | | 49.000 | | 251.000 | | 7.300 | | 5.100 | |
| 2 | 8.000 | 336.000 | −6.100 | 40.000 | −18.400 | 231.000 | −8.000 | 8.400 | 15.100 | 5.800 | 13.700 |
| 3 | 15.000 | 321.000 | −10.300 | 49.000 | 0.000 | 236.000 | −6.000 | 6.600 | −9.600 | 4.800 | −5.900 |
| 4 | 22.000 | 254.000 | −29.100 | 43.000 | −12.200 | 175.000 | −30.300 | 5.900 | −19.200 | 4.100 | −19.600 |
| | | | | PT. 5 CHOLESTEROL DATA | | | | | | | |
| 1 | 1.000 | 203.000 | | 31.000 | | 118.000 | | 6.500 | | 3.800 | |
| 2 | 8.000 | 208.000 | 2.500 | 31.000 | 0.000 | 125.000 | 5.900 | 6.700 | 3.100 | 4.000 | 5.300 |
| 3 | 15.000 | 179.000 | −11.800 | 25.000 | −19.400 | 105.000 | −11.000 | 7.200 | 10.800 | 4.200 | 10.500 |
| 4 | 33.000 | 176.000 | −13.300 | 31.000 | 0.000 | 105.000 | −11.000 | 5.700 | −12.300 | 3.400 | −10.500 |
| | | | | PT. 6 CHOLESTEROL DATA | | | | | | | |
| 1 | 1.000 | 195.000 | | 21.000 | | 148.000 | | 9.300 | | 7.100 | |
| 2 | 8.000 | 208.000 | 6.700 | 26.000 | 23.800 | 160.000 | 8.100 | 8.000 | −14.000 | 6.200 | −12.700 |
| 3 | 15.000 | 190.000 | −2.600 | 28.000 | 33.300 | 147.000 | −0.700 | 6.800 | −26.900 | 5.200 | −26.800 |
| 4 | 22.000 | 173.000 | −11.300 | 26.000 | 23.800 | 127.000 | −14.200 | 6.700 | −28.000 | 4.900 | −31.000 |
| 5 | 29.000 | 161.000 | −22.600 | 27.000 | 28.600 | 114.000 | −23.000 | 6.000 | −35.500 | 4.200 | −40.800 |
| | | | | PT 7 CHOLESTEROL DATA | | | | | | | |
| 1 | 1.000 | 229.000 | | 27.000 | | 140.000 | | 8.500 | | 5.200 | |
| 2 | 8.000 | 216.000 | −5.700 | 28.000 | 3.700 | 157.000 | 12.100 | 7.700 | −9.400 | 5.600 | 7.700 |
| 3 | 21.000 | 201.000 | −12.200 | 25.000 | −7.400 | 151.000 | 7.900 | 8.000 | −5.900 | 6.000 | 15.400 |
| 4 | 28.000 | 231.000 | 0.900 | 32.000 | 18.500 | 174.000 | 24.300 | 7.200 | −15.300 | 5.400 | 3.800 |
| 5 | 35.000 | 236.000 | 3.100 | 33.000 | 22.200 | 176.000 | 25.700 | 7.200 | −15.300 | 5.300 | 1.900 |
| 6 | 42.000 | 220.000 | −3.900 | 32.000 | 18.500 | 154.000 | 10.000 | 6.900 | −18.900 | 4.800 | −7.700 |
| | | | | PT. 8 CHOLESTEROL DATA | | | | | | | |
| 1 | 1.000 | 235.000 | | 29.000 | | 183.000 | | 8.100 | | 6.300 | |

TABLE 2-continued

EFFECT OF CLARITHROMYCIN ON PLASMA CHOLESTEROL
LEVELS IN PATIENTS WITH HYPERCHOLESTEROLEMIA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 2 | 8.000 | 202.000 | −16.300 | 27.000 | −6.900 | 134.000 | −26.800 | 7.500 | −7.400 | 5.000 | −20.600 |
| 3 | 15.000 | 243.000 | 3.400 | 41.000 | 34.500 | 154.000 | −15.800 | 5.900 | −27.200 | 3.800 | −39.700 |
| 4 | 22.000 | 230.000 | −2.100 | 36.000 | 26.900 | 162.000 | −11.500 | 6.400 | −21.000 | 4.500 | −28.600 |

PT. 9 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 194.000 | | 32.000 | | 83.000 | | 6.100 | | 2.600 | |
| 2 | 8.000 | 155.000 | −20.100 | 33.000 | 3.100 | 77.000 | −7.200 | 4.700 | −23.000 | 2.300 | 11.500 |
| 3 | 15.000 | 173.000 | −10.800 | 34.000 | 6.200 | 104.000 | 25.300 | 5.100 | −16.400 | 3.000 | 15.400 |
| 4 | 38.000 | 191.000 | −1.500 | | | | | | | | |
| 5 | 45.000 | 182.000 | −6.200 | 33.000 | 3.100 | 112.000 | 34.900 | 5.500 | −9.800 | 3.400 | 30.800 |
| 6 | 60.000 | 212.000 | 9.300 | 38.000 | 18.700 | 140.000 | 40.700 | 5.600 | −8.200 | 3.700 | 42.300 |
| 7 | 66.000 | 168.000 | −13.400 | 37.000 | 15.600 | 108.000 | 30.100 | 4.500 | −26.200 | 2.900 | 11.500 |

PT. 10 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 183.000 | | 36.000 | | 104.000 | | 5.100 | | 2.900 | |
| 2 | 8.000 | 217.000 | 18.600 | 37.000 | 2.800 | 164.000 | 58.000 | 5.900 | 15.700 | 4.400 | 51.700 |
| 3 | 15.000 | 190.000 | 3.800 | 32.000 | −11.100 | 126.000 | 21.200 | 5.900 | 15.700 | 3.900 | 34.400 |
| 4 | 22.000 | 235.000 | 28.400 | 38.000 | 5.600 | 176.000 | 69.200 | 6.200 | 21.600 | 4.600 | 58.600 |
| 5 | 29.000 | 202.000 | 10.400 | 38.000 | 5.600 | 146.000 | 40.400 | 5.300 | 3.900 | 3.900 | 34.400 |

PT. 11 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 259.000 | | 32.000 | | 172.000 | | 8.100 | | 5.400 | |
| 2 | 8.000 | 215.000 | −17.000 | 34.000 | 6.300 | 151.000 | −12.200 | 6.300 | −22.200 | 4.400 | −18.500 |
| 3 | 15.000 | 232.000 | −10.400 | 31.000 | −3.100 | 159.000 | −7.600 | 7.500 | −7.400 | 5.100 | −5.600 |
| 4 | 22.000 | 230.000 | −15.100 | 33.000 | 3.100 | 157.000 | −8.700 | 7.000 | −13.600 | 4.800 | −11.100 |
| 5 | 29.000 | 217.000 | −16.200 | 31.000 | −3.100 | 149.000 | −13.400 | 7.000 | −13.600 | 4.800 | −11.100 |
| 6 | 36.000 | 235.000 | −9.300 | 38.000 | 18.700 | 155.000 | −9.900 | 6.200 | −23.500 | 4.100 | −24.100 |
| 7 | 43.000 | 236.000 | −8.800 | 36.000 | 12.500 | 148.000 | −14.000 | 6.600 | −18.500 | 4.100 | −24.100 |

PT. 12 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 220.000 | | 35.000 | | 129.000 | | 6.300 | | 3.700 | |
| 2 | 8.000 | 228.000 | 3.600 | 33.000 | −5.700 | 144.000 | 11.600 | 6.900 | 9.500 | 4.400 | 18.900 |
| 3 | 15.000 | 237.000 | 7.700 | 40.000 | 14.300 | 159.000 | 23.200 | 5.900 | −6.300 | 4.000 | 8.100 |
| 4 | 22.000 | 233.000 | 5.900 | 41.000 | 17.100 | 161.000 | 39.000 | 5.700 | −9.500 | 3.900 | 5.400 |

PT. 13 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 181.000 | | 31.000 | | 128.000 | | 5.800 | | 4.100 | |
| 2 | 8.000 | 188.000 | 3.700 | 35.000 | 11.400 | 139.000 | 8.500 | 5.400 | −6.900 | 4.000 | −2.400 |
| 3 | 15.000 | 170.000 | −6.100 | 37.000 | 19.300 | 123.000 | −3.900 | 4.600 | −20.700 | 3.300 | −19.500 |
| 4 | 22.000 | 168.000 | −7.200 | 34.000 | 9.700 | 120.000 | 6.300 | 4.900 | −15.500 | 3.500 | −14.600 |
| 5 | 57.000 | 234.000 | 29.300 | 46.000 | 48.400 | 174.000 | 35.900 | 5.100 | −12.100 | 3.800 | −7.300 |

PT. 14 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 177.000 | | 34.000 | | 122.000 | | 5.200 | | 3.600 | |
| 2 | 8.000 | 151.000 | −14.700 | 34.000 | 0.000 | 97.000 | −20.500 | 4.400 | −15.400 | 2.800 | −22.200 |
| 3 | 15.000 | 140.000 | −20.900 | 29.000 | −14.700 | 77.000 | −36.900 | 4.800 | −7.700 | 2.700 | −25.000 |

PT. 15 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 164.000 | | 22.000 | | 106.000 | | 7.500 | | 4.800 | |
| 2 | 8.000 | 165.000 | 0.600 | 26.000 | 18.200 | 103.000 | −2.800 | 6.300 | −16.000 | 3.900 | −18.700 |
| 3 | 15.000 | 150.000 | −6.100 | 25.000 | 13.600 | 109.000 | 2.800 | 6.000 | −20.000 | 4.300 | −10.400 |
| 4 | 22.000 | 150.000 | −6.100 | 21.000 | −4.500 | 102.000 | −3.800 | 7.100 | −5.300 | 4.900 | 2.100 |
| 5 | 29.000 | 146.000 | −11.000 | 24.000 | 9.100 | 100.000 | −5.700 | 6.100 | −18.700 | 4.200 | −12.500 |

PT. 16 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 232.000 | | 50.000 | | 117.000 | | 4.600 | | 2.400 | |
| 2 | 8.000 | 191.000 | −17.700 | 43.000 | −14.000 | 102.000 | −12.800 | 4.400 | −4.300 | 2.400 | 0.000 |
| 3 | 15.000 | 180.000 | 22.400 | 37.000 | −26.000 | 109.000 | −6.800 | 4.900 | 6.500 | 3.000 | 25.000 |

PT. 17 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 213.000 | | 37.000 | | 135.000 | | 5.800 | | 3.600 | |
| 2 | 8.000 | 210.000 | −1.400 | 36.000 | −2.800 | 143.000 | 5.900 | 5.800 | 0.000 | 4.000 | 11.100 |
| 3 | 15.000 | 208.000 | −2.300 | 39.000 | 5.400 | 137.000 | 1.500 | 5.300 | −8.600 | 3.500 | −2.800 |
| 4 | 22.000 | 204.000 | −4.200 | 40.000 | 8.100 | 138.000 | 1.200 | 5.100 | −12.100 | 3.500 | −2.800 |

PT. 18 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 209.000 | | 51.000 | | 150.000 | | 4.100 | | 2.900 | |
| 2 | 8.000 | 194.000 | −7.200 | 53.000 | 3.900 | 132.000 | −12.000 | 3.700 | −9.800 | 2.500 | −13.800 |
| 3 | 15.000 | 219.000 | 4.500 | 49.000 | −3.900 | 159.000 | 5.700 | 4.500 | 9.800 | 3.200 | 10.300 |

PT. 19 CHOLESTEROL DATA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| 1 | 1.000 | 213.000 | | 47.000 | | 148.000 | | 4.500 | | 3.100 | |
| 2 | 8.000 | 217.000 | 1.800 | 42.000 | −10.600 | 131.000 | −7.400 | 5.200 | 15.600 | 3.100 | 0.000 |
| 3 | 15.000 | 207.000 | −2.800 | 57.000 | 21.200 | 124.000 | −16.200 | 3.600 | −20.000 | 2.200 | −29.000 |

TABLE 2-continued

EFFECT OF CLARITHROMYCIN ON PLASMA CHOLESTEROL LEVELS IN PATIENTS WITH HYPERCHOLESTEROLEMIA

| | DAY | CHOLESTEROL | % CHANGE | HDL | % CHANGE | LDL | % CHANGE | CHOL/HDL | % CHANGE | LDL/HDL | % CHANGE |
|---|---|---|---|---|---|---|---|---|---|---|---|
| | | | | PT. 20 CHOLESTEROL DATA | | | | | | | |
| 1 | 1.000 | 240.000 | | 30.000 | | 154.000 | | 8.000 | | 5.100 | |
| 2 | 8.000 | 215.000 | −10.400 | 36.000 | 20.000 | 147.000 | −4.500 | 6.000 | −25.000 | 4.100 | −19.600 |
| 3 | 15.000 | 234.000 | −2.500 | 39.000 | 30.000 | 144.000 | −6.500 | 6.000 | −25.000 | 3.700 | −37.800 |
| 4 | 22.000 | 241.000 | 0.400 | 41.000 | 36.700 | 154.000 | 0.000 | 5.900 | −26.200 | 3.700 | −37.800 |
| | | | | PT. 21 CHOLESTEROL DATA | | | | | | | |
| 1 | 1.000 | 145.000 | | 32.000 | | 91.000 | | 4.500 | | 2.800 | |
| 2 | 8.000 | 161.000 | 11.000 | 45.000 | 40.600 | 81.000 | −11.000 | 3.600 | −20.000 | 1.800 | −35.700 |
| 3 | 15.000 | 165.000 | 13.800 | 49.000 | 53.100 | 88.000 | −3.300 | 3.400 | −24.400 | 1.800 | −35.700 |

What is claimed is:

1. A method of treating a human having hypercholesterolemia comprising administering to the human an effective dose for treating hypercholesterolemia of an erythromycin compound.

2. The method of claim 1, wherein the erythromycin compound is selected from the group consisting of clarithromycin, troleandomycin, erythromycin, and azithromycin.

3. The method of claim 1, wherein the dose is administered orally and ranges from about 100 mg/day to about 6,000 mg/day.

4. The method of claim 1, wherein the dose ranges from 1 mg/kg of body weight/day to 100 mg/kg of body weight/day.

5. A method of treating a human having hypercholesterolemia characterized by a supranormal total plasma cholesterol concentration comprising administering to the human an effective dose for decreasing the total plasma cholesterol concentration of an erythromycin compound.

6. The method of claim 5, wherein the erythromycin compound is selected from the group consisting of clarithromycin, troleandomycin, erythromycin, and azithromycin.

7. The method of claim 5, wherein the dose is administered orally and ranges from about 100 mg/day to about 6,000 mg/day.

8. The method of claim 5 wherein the dose ranges from 1 mg/kg of body weight/day to 100 mg/kg of body weight/day.

9. A method of treating a human having hypercholesterolemia characterized by a supranormal ratio of plasma low-density lipoprotein cholesterol concentration to plasma high-density lipoprotein cholesterol concentration comprising administering to the human an effective dose for decreasing the ratio of plasma low-density lipoprotein concentration to plasma high-density lipoprotein concentration of an erythromycin compound.

10. The method of claim 9, wherein the erythromycin compound is selected from the group consisting of clarithromycin, troleandomycin, erythromycin, and azithromycin.

11. The method of claim 9 wherein the dose is administered orally and ranges from about 100 mg/day to about 6,000 mg/day.

12. The method of claim 9 wherein the dose ranges from 1 mg/kg of body weight/day to 100 mg/kg of body weight/day.

13. A method of treating a human having hyoercholesterolemia characterized by a supranormal plasma low-density lipoprotein cholesterol concentration comprising administering to the human an effective dose for decreasing the plasma low-density lipoprotein cholesterol concentration of an erythromycin compound.

14. The method of claim 13, wherein the erythromycin compound is selected from the group consisting of clarithromycin, troleandomycin, erythromycin, and azithromycin.

15. The method of claim 13 wherein the dose is administered orally and ranges from about 100 mg/day to about 6,000 mg/day.

16. The method of claim 13 wherein the dose ranges from 1 mg/kg of body weight/day to 100 mg/kg of body weight/day.

17. A method of treating a human having hypercholesterolemia characterized by a below normal plasma high-density lipoprotein cholesterol concentration comprising administering to the human an effective dose for increasing the plasma high-density lipoprotein cholesterol concentration of an erythromycin compound.

18. The method of claim 17, wherein the erythromycin compound is selected from the group consisting of clarithromycin, troleandomycin, erythromycin, and azithromycin.

19. The method of claim 17, wherein the dose is administered orally and ranges from about 100 mg/day to about 6,000 mg/day.

20. The method of claim 17, wherein the dose ranges from 1 mg/kg of body weight/day to 100 mg/kg of body weight/day.

21. The method of claim 1, wherein the dose is about 11 mg/kg of body weight/day.

22. The method of claim 1, wherein the dose is about 22 mg/kg of body weight/day.

23. A method of treating a human having hypercholesterolemia, comprising:
   administering to the human a dose of an erythromycin compound ranging from 1 mg/kg of body weight/day to 100 mg/kg of body weight/day;
   decreasing the plasma low-density lipoprotein cholesterol concentration in the human; and
   increasing the plasma high-density lipoprotein cholesterol concentration in the human.

24. The method of claim 23, further comprising decreasing the total plasma cholesterol concentration in the human.

25. The method of claim 23, further comprising decreasing the ratio of the plasma low-density lipoprotein cholesterol concentration to the plasma high-density lipoprotein cholesterol concentration in the human.

26. The method of claim 23, further comprising decreasing the ratio of the total plasma cholesterol concentration to the plasma high-density lipoprotein cholesterol concentration in the human.

27. A method of treating a human having hypercholesterolemia, comprising:
  administering to the human a dose of clarithromycin ranging from 1 mg/kg of body weight/day to 100 mg/kg of body weight/day;
  decreasing the plasma low-density lipoprotein cholesterol concentration in the human; and
  increasing the plasma high-density lipoprotein cholesterol concentration in the human.

28. The method of claim 27, further comprising decreasing the total plasma cholesterol concentration in the human.

29. The method of claim 28, further comprising decreasing the ratio of the plasma low-density lipoprotein cholesterol concentration to the plasma high-density lipoprotein cholesterol concentration in the human.

30. The method of claim 29, further comprising decreasing the ratio of the total plasma cholesterol concentration to the plasma high-density lipoprotein cholesterol concentration in the human.

31. The method of claim 5, wherein the dose is about 11 mg/kg of body weight/day.

32. The method of claim 5, wherein the dose is about 22 mg/kg of body weight/day.

33. The method of claim 5, further comprising decreasing the plasma low-density lipoprotein cholesterol concentration in the human.

34. The method of claim 5, further comprising increasing the plasma high-density lipoprotein cholesterol concentration in the human.

35. The method of claim 5, further comprising decreasing the ratio of plasma low-density lipoprotein cholesterol concentration to plasma high-density lipoprotein cholesterol concentration in the human.

36. The method of claim 5, further comprising decreasing the ratio of total plasma cholesterol concentration to plasma high-density lipoprotein cholesterol concentration in the human.

37. The method of claim 9, wherein the dose is about 11 mg/kg of body weight/day.

38. The method of claim 9, wherein the dose is about 22 mg/kg of body weight/day.

39. The method of claim 9, further comprising decreasing the plasma low-density lipoprotein cholesterol concentration in the human.

40. The method of claim 9, further comprising increasing the plasma high-density lipoprotein cholesterol concentration in the human.

41. The method of claim 9, further comprising decreasing the ratio of total plasma cholesterol concentration to plasma high-density lipoprotein cholesterol concentration in the human.

42. The method of claim 9, further comprising decreasing the total plasma cholesterol concentration in the human.

43. The method of claim 13, wherein the dose is about 11 mg/kg of body weight/day.

44. The method of claim 13, wherein the dose is about 22 mg/kg of body weight/day.

45. The method of claim 13, further comprising increasing the plasma high-density lipoprotein cholesterol concentration in the human.

46. The method of claim 13, further comprising decreasing the ratio of plasma low-density lipoprotein cholesterol concentration to plasma high-density lipoprotein cholesterol concentration in the human.

47. The method of claim 13, further comprising decreasing the ratio of total plasma cholesterol concentration to plasma high-density lipoprotein cholesterol concentration in the human.

48. The method of claim 13, further comprising decreasing the total plasma cholesterol concentration in the human.

49. The method of claim 17, wherein the dose is about 11 mg/kg of body weight/day.

50. The method of claim 17, wherein the dose is about 22 mg/kg of body weight/day.

51. The method of claim 17, further comprising decreasing the plasma low-density lipoprotein cholesterol concentration in the human.

52. The method of claim 17, further comprising decreasing the ratio of plasma low-density lipoprotein cholesterol concentration to plasma high-density lipoprotein cholesterol concentration in the human.

53. The method of claim 17, further comprising decreasing the ratio of total plasma cholesterol concentration to plasma high-density lipoprotein cholesterol concentration in the human.

54. The method of claim 17, further comprising decreasing the total plasma cholesterol concentration in the human.

* * * * *